(12) United States Patent
Mukhopadhyay et al.

(10) Patent No.: US 9,163,063 B2
(45) Date of Patent: Oct. 20, 2015

(54) PEPTIDES AND NANOPARTICLES FOR THERAPEUTIC AND DIAGNOSTIC APPLICATIONS

(71) Applicants: Trustees of Dartmouth College, Hanover, NH (US); Mayo Foundation for Medical Education and Research, Rochester, MN (US)

(72) Inventors: Debabrata Mukhopadhyay, Rochester, MN (US); Priyabrata Mukherjee, Rochester, MN (US); Mark Spaller, Hanover, NH (US)

(73) Assignees: Trustees of Darmouth College, Hanover, NH (US); Mayo Foundation for Medical Education and Research, Rochester, MN (US)

( * ) Notice: Subject to any disclaimer, the term of this patent is extended or adjusted under 35 U.S.C. 154(b) by 63 days.

(21) Appl. No.: 14/060,932

(22) Filed: Oct. 23, 2013

(65) Prior Publication Data
US 2014/0329760 A1 Nov. 6, 2014

Related U.S. Application Data

(63) Continuation of application No. 13/195,663, filed on Aug. 1, 2011, now Pat. No. 8,658,601, which is a continuation-in-part of application No. PCT/US2010/022598, filed on Jan. 29, 2010.

(60) Provisional application No. 61/148,868, filed on Jan. 30, 2009.

(51) Int. Cl.
| | |
|---|---|
| *C07K 7/06* | (2006.01) |
| *A61K 47/48* | (2006.01) |
| *B82Y 5/00* | (2011.01) |
| *C07K 14/47* | (2006.01) |

(52) U.S. Cl.
CPC ............. *C07K 7/06* (2013.01); *A61K 47/48861* (2013.01); *B82Y 5/00* (2013.01); *C07K 14/4706* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 6,126,939 A * | 10/2000 | Eisenbach-Schwartz et al. ................ | 424/185.1 |
| 7,060,802 B1 | 6/2006 | Trakht et al. ............. | 530/388.85 |
| 7,514,224 B2 * | 4/2009 | Lu et al. ................... | 435/7.1 |
| 2001/0005581 A1 | 6/2001 | Grant et al. .............. | 435/7.21 |
| 2003/0053983 A1 | 3/2003 | Tamarkin et al. ......... | 424/85.1 |
| 2003/0118657 A1 | 6/2003 | West et al. ............... | 424/489 |
| 2004/0214272 A1 * | 10/2004 | La Rosa et al. .......... | 435/69.1 |
| 2005/0037969 A1 * | 2/2005 | Lu et al. ................... | 514/12 |
| 2006/0022295 A1 | 2/2006 | Takafuji et al. .......... | 257/495 |
| 2006/0123505 A1 * | 6/2006 | Kikuchi et al. ........... | 800/278 |
| 2006/0251726 A1 | 11/2006 | Lin et al. ................. | 424/489 |
| 2008/0227684 A1 | 9/2008 | Belmares et al. ......... | 514/1.1 |
| 2013/0333061 A1 * | 12/2013 | Wu et al. .................. | 800/260 |

FOREIGN PATENT DOCUMENTS

WO    WO 2004/092339 A2 * 10/2004

OTHER PUBLICATIONS

Uniprot F6VSK8 "integrin alpha-6" Jul. 27, 2011.*
Uniprot H3RCI4 "protein phosphatase CheZ" Apr. 18, 2012.*
Awan et al. "5T4 Interacts with TIP-2/GIPC, a PDZ Protein, with Implications for Metastasis" Biochemical and Biophysical Research Communications 2002 290:1030-1036.
Bardeesy, N. and DePinho, R.A. "Pancreatic Cancer Biology and Genetics" Nature Reviews Cancer 2002 2:897-909.
Berge et al. "Pharmaceutical Salts" Journal of Pharmaceutical Sciences 1977 66:1-19.
Booth et al. "GIPC Participates in G Protein Signaling Downstream of Insulin-Like Growth Factor 1 Receptor" Journal of Biological Chemistry 2002 277:6719-6725.
Chen et al. "High-Throughput Screen for Small Molecule Inhibitors of Mint1-PDZ Domains" Assay and Drug Development Technologies 2007 5(6):769-783A.
De Vries et al. "GIPC, a PDZ Domain Containing Protein, Interacts Specifically with the C Terminus of RGS-GAIP" Proceedings of the National Academy of Sciences USA 1998 95:12340-12345.
El Mourabit et al. "The PDZ Domain of TIP-2/GIPC Interacts with the C-Terminus of the Integrin Alpha5 and Alpha6 Subunits" Matrix Biology 2002 21:207-214.
Gao et al. "Synectin, Syndecan-4 Cytoplasmic Domain Binding PDZ Protein, Inhibits Cell Migration" Journal of Cellular Physiology 2000 184:373-379.
Hasson, T. "Myosin VI: Two Distinct Roles in Endocytosis" Journal of Cell Science 2003 116:3453-3461.
Hirakawa et al. "GIPC Binds to the Human Lutropin Receptor (hLHR) Through an Unusual PDZ Domain Binding Motif, and it Regulates the Sorting of the Internalized Human Choriogonadotropin and the Density of Cell Surface hLHR" Journal of Biological Chemistry 2003 278:49348-49357.
Hu et al. "GIPC Interacts with the Beta1-Adrenergic Receptor and Regulates Beta1-Adrenergic Receptor-Mediated ERK Activation" Journal of Biological Chemistry 2003 278:26295-26301.
Jeanneteau et al. "GIPC Recruits GAIP (RGS19) to Attenuate Dopamine D2 Receptor Signaling" Molecular Biology of the Cell 2004 15:4926-4937.

(Continued)

*Primary Examiner* — Christina Bradley
(74) *Attorney, Agent, or Firm* — Licata & Tyrrell P.C.

(57) ABSTRACT

Provided herein are peptides and nanoparticles conjugates thereof useful for the treatment of diseases and disorders mediated by GIPC/synectin, such as cancer.

12 Claims, 37 Drawing Sheets

(56) References Cited

OTHER PUBLICATIONS

Jeanneteau et al. "Interactions of GIPC with Dopamine D2, D3 but Not D4 Receptors Define a Novel Mode of Regulation of G Protein-Coupled Receptors" Molecular Biology of the Cell 2004 15:696-705.
Katoh, M. "GIPC Gene Family (Review)" International Journal of Molecular Medicine 2002 9:585-589.
Kirikoshi, H. and Katoh, M. "Expression of Human GIPC1 in Normal Tissues, Cancer Cell Lines, and Primary Tumors" International Journal of Molecular Medicine 2002 9:509-513.
Ligensa et al. "A PDZ Domain Protein Interacts with the C-Terminal Tail of the Insulin-Like Growth Factor-1 Receptor But Not with the Insulin Receptor" Journal of Biological Chemistry 2001 276:33419-33427.
Liu et al. "PDZ Domain in Protein GIPC Interacts with the Cytoplasmic Tail of Melanosomal Membrane Protein gp75(Tyrosinase-Related Protein-1)" Journal of Biological Chemistry 2001 276(38):35768-35777.
Lou et al. "GIPC and GAIP Form a Complex with TrkA: a Putative Link Between G Protein and Receptor Tyrosine Kinase Pathways" Molecular Biology of the Cell 2001 12:615-627.
Muders et al. "Expression and Regulatory Role of GAIP-Interacting Protein GIPC in Pancreatic Adenocarcinoma" Cancer Research 2006 66(21):10264-10268.
Muders et al. "Is GIPC a New Target for the Treatment of Pancreatic Adenocarcinoma?" Proceedings of the Deutsche Gesellschaft für Pathologie [German Pathology Society] 91st Conference May 30-Jun. 2, 2007 p. 286-293.
Muders et al. "Targeting GIPC/Synectin in Pancreatic Cancer Inhibits Tumor Growth" Clinical Cancer Research 2009 15(12):4095-4103.
Prahst et al. "Neuropilin-1-VEGFR-2 Complexing Requires the PDZ-Binding Domain of Neuropilin-1" Journal of Biological Chemistry 2008 283:25110-25114.
Rudchenko et al. "A Human Monoclonal Autoantibody to Breast Cancer Identifies the PDZ Domain Containing Protein GIPC1 as a Novel Breast Cancer-Associated Antigen" BMC Cancer 2008 8:248.
Saro et al. "A Thermodynamic Ligand Binding Study of the Third PDZ Domain (PDZ3) from the Mammalian Neuronal Protein PSD-95" Biochemistry 2007 46:6340-6352.
Schenck et al. "The Endosomal Protein App11 Mediates Akt Substrate Specificity and Cell Survival in Vertebrate Development" Cell 2008 133:486-497.
Sehat et al. "Role of Ubiquitination in IGF-1 Receptor Signaling and Degradation" PLoS ONE 2007 2:e340.
Tani, T.T. and Mercurio, A.M. "PDZ Interaction Sites in Integrin Alpha Subunits. T14853, TIP/GIPC Binds to a Type I Recognition Sequence in Alpha 6A/Alpha 5 and a Novel Sequence in Alpha 6B" Journal of Biological Chemistry 2001 276:36535-36542.
Varsano et al. "GIPC Is Recruited by APPL to Peripheral TrkA Endosomes and Regulates TrkA Trafficking and Signaling" Molecular and Cellular Biology 2006 26:8942-8952.
Wang et al. "A PDZ Protein Regulates the Distribution of the Transmembrane Semaphorin, M-SemF" Journal of Biological Chemistry 1999 274:14137-14146.
Wang et al. "C Terminus of RGS-GAIP-Interacting Protein Conveys Neuropilin-1-Mediated Signaling During Angiogenesis" The Faseb Journal 2006 20(9):1513-1515.
Wen et al. "Targeting PDZ Domain Proteins for Treating NMDA Receptor-Mediated Excitotoxicity" Current Topics in Medicinal Chemistry 2006 6:711-721.
Wu et al. "Kermit 2/XGIPC, an IGF1 Receptor Interacting Protein, Is Required for IGF Signaling in Xenopus Eye Development" Development 2006 133:3651-3660.
Zhu et al. "Nerve Growth Factor Expression Correlates with Perineural Invasion and Pain in Human Pancreatic Cancer" Journal of Clinical Oncology 1999 17:2419-2428.
International Search Report from PCT/US2010/022598, Nov. 11, 2010.
International Preliminary Report on Patentability from PCT/US2010/022598, Aug. 11, 2011.

\* cited by examiner

Day 24 Post Transplant

Empty Vector

GIPC shRNA
Expressing Vector

Day 39 Post Transplant

Empty Vector

GIPC shRNA
Expressing Vector

Integrin expression in PCA cell lines, U87 and 293T are controls.

Downregulation of EGFR expression after siRNA treatment against GIPC and a competitive peptide against int-binding domain of GIPC treatment in MIA PaCa2.

SEQUENCE LISTING

```
<160> NUMBER OF SEQ ID NOS: 35

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Proline, 4-hydroxyproline, 4-oxoproline,
      3,4-dehydroproline, 4-thiaproline, 4-aminoproline, or pipecolic
      acid
<220> FEATURE:
<221> NAME/KEY: MOD_RES
<222> LOCATION: (2)..(2)
```

```
<223> OTHER INFORMATION: Serine, homoserine, cysteine,
      alpha-methylcysteine, penicillamine, threonine, alpha-
      methylthreonine, alanine, allylglycine, benzoyllysine,
      4-bromobenzoyllysine, or norvaline
<220> FEATURE:
<221> NAME/KEY: MOD_RES
<222> LOCATION: (3)..(3)
<223> OTHER INFORMATION: Glutamine, glutamic acid, aspartic acid, or
      asparagine
<220> FEATURE:
<221> NAME/KEY: MOD_RES
<222> LOCATION: (4)..(6)
<223> OTHER INFORMATION: Serine, homoserine, cysteine, alpha-
      methylcysteine, penicillamine, threonine, alpha-methylthreonine,
      alanine, allylglycine, benzoyllysine, 4-bromobenzoyllysine,
      or norvaline
<220> FEATURE:
<221> NAME/KEY: MOD_RES
<222> LOCATION: (7)..(7)
<223> OTHER INFORMATION: Glutamine, glutamic acid, aspartic acid,
      benzoyllysine, 4-bromobenzoyllysine, or asparagine
<220> FEATURE:
<221> NAME/KEY: MOD_RES
<222> LOCATION: (8)..(8)
<223> OTHER INFORMATION: Glycine, alanine, alpha-aminoisobutyric acid,
      allylglycine, valine, or norvaline
<220> FEATURE:
<223> OTHER INFORMATION: see specification as filed for detailed
      description of substitutions and preferred embodiments

<400> SEQUENCE: 1

Xaa Xaa Xaa Xaa Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine, 4-aminoproline, lysine, or arginine
<220> FEATURE:
<221> NAME/KEY: MOD_RES
<222> LOCATION: (2)..(2)
<223> OTHER INFORMATION: Glutamine, glutamic acid, aspartic acid, or
      asparagine
<220> FEATURE:
<221> NAME/KEY: MOD_RES
<222> LOCATION: (3)..(3)
<223> OTHER INFORMATION: Ornithine, lysine, arginine, or
      4-aminomethylphenylalanine
<220> FEATURE:
<221> NAME/KEY: MOD_RES
<222> LOCATION: (4)..(4)
<223> OTHER INFORMATION: Valine, leucine, tert-leucine, alanine,
      allylglycine, norvaline, 2-indanylglycine, phenylglycine,
      propargylglycine, cyclohexylalanine, cyclohexylglycine, or
      threonine
<220> FEATURE:
<221> NAME/KEY: MOD_RES
<222> LOCATION: (5)..(5)
<223> OTHER INFORMATION: Valine, serine, threonine, L-allo-threonine,
      tert-leucine, penicillamine, leucine, or homoserine
<220> FEATURE:
<221> NAME/KEY: MOD_RES
<222> LOCATION: (6)..(6)
<223> OTHER INFORMATION: Serine, homoserine, cysteine, alpha-
      methylcysteine, penicillamine, threonine, alpha-methylthreonine,
      alanine, allylglycine, or norvaline
<220> FEATURE:
<221> NAME/KEY: MOD_RES
<222> LOCATION: (7)..(7)
<223> OTHER INFORMATION: Aspartic acid, glutamic acid, asparagine,
```

```
       glutamine, or sulphouralanine
<220>  FEATURE:
<221>  NAME/KEY: MOD_RES
<222>  LOCATION: (8)..(8)
<223>  OTHER INFORMATION: Glycine, alanine, alpha-aminoisobutyric acid,
       allylglycine, valine, or norvaline
<220>  FEATURE:
<223>  OTHER INFORMATION: see specification as filed for detailed
       description of substitutions and preferred embodiments

<400>  SEQUENCE: 2

Xaa Xaa Xaa Xaa Xaa Xaa Xaa Xaa
1               5

<210>  SEQ ID NO 3
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide

<400>  SEQUENCE: 3

Pro Ser Gln Ser Ser Ser Glu Ala
1               5

<210>  SEQ ID NO 4
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide

<400>  SEQUENCE: 4

Pro Cys Gln Ser Ser Ser Glu Ala
1               5

<210>  SEQ ID NO 5
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide

<400>  SEQUENCE: 5

Pro Ser Gln Cys Ser Ser Glu Ala
1               5

<210>  SEQ ID NO 6
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide

<400>  SEQUENCE: 6

Pro Ser Gln Ser Cys Ser Glu Ala
1               5

<210>  SEQ ID NO 7
<211>  LENGTH: 8
<212>  TYPE: PRT
<213>  ORGANISM: Artificial Sequence
<220>  FEATURE:
<223>  OTHER INFORMATION: Description of Artificial Sequence: Synthetic
       peptide
```

```
<400> SEQUENCE: 7

Pro Ser Gln Ser Ser Cys Glu Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Glu Arg Leu Thr Ser Asp Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Glu Arg Leu Thr Cys Asp Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu Arg Leu Thr Ser Asp Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Glu Arg Leu Thr Cys Asp Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Glu Thr Glu Val
1               5

<210> SEQ ID NO 13
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Glu Thr Ala Val
1               5

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccgggcaaat gcaataatgc cctcactcga gtgagggcat tattgcattt gcttttg        58

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Asp Ser Thr Leu Arg Glu Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group

<400> SEQUENCE: 16

Pro Ser Gln Ser Ser Ser Glu Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (7)..(7)
<223> OTHER INFORMATION: Benzoyllysine

<400> SEQUENCE: 17

Pro Ser Gln Ser Ser Ser Lys Ala
1               5

<210> SEQ ID NO 18
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (7)..(7)
<223> OTHER INFORMATION: 4-bromobenzoyllysine

<400> SEQUENCE: 18

Pro Ser Gln Ser Ser Ser Lys Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (5)..(5)
<223> OTHER INFORMATION: Benzoyllysine
<220> FEATURE:
<221> NAME/KEY: MOD_RES
<222> LOCATION: (7)..(7)
<223> OTHER INFORMATION: Benzoyllysine

<400> SEQUENCE: 19

Pro Ser Gln Ser Lys Ser Lys Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (5)..(5)
<223> OTHER INFORMATION: 4-bromobenzoyllysine
<220> FEATURE:
<221> NAME/KEY: MOD_RES
<222> LOCATION: (7)..(7)
<223> OTHER INFORMATION: 4-bromobenzoyllysine

<400> SEQUENCE: 20

Pro Ser Gln Ser Lys Ser Lys Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (5)..(5)
<223> OTHER INFORMATION: Benzoyllysine

<400> SEQUENCE: 21
```

```
Pro Ser Gln Ser Lys Ser Glu Ala
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group

<400> SEQUENCE: 22

Leu Leu Gln Gly Pro Ser Gln Ser Ser Ser Glu Ala
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group

<400> SEQUENCE: 23

Ser Glu Ser Pro Ser Ala Ser Gln
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (6)..(6)
<223> OTHER INFORMATION: 4-bromobenzoyllysine

<400> SEQUENCE: 24

Ser Pro Ser Ala Ser Lys Ser Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (1)..(1)
<223> OTHER INFORMATION: Lys(FITC)

<400> SEQUENCE: 25

Lys Pro Ser Gln Ser Ser Ser Glu Ala
1               5

<210> SEQ ID NO 26
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (1)..(1)
<223> OTHER INFORMATION: Lys(FITC)
<220> FEATURE:
<221> NAME/KEY: MOD_RES
<222> LOCATION: (6)..(6)
<223> OTHER INFORMATION: Benzoyllysine
<220> FEATURE:
<221> NAME/KEY: MOD_RES
<222> LOCATION: (8)..(8)
<223> OTHER INFORMATION: Benzoyllysine

<400> SEQUENCE: 26

Lys Pro Ser Gln Ser Lys Ser Lys Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (1)..(1)
<223> OTHER INFORMATION: Lys(FITC)
<220> FEATURE:
<221> NAME/KEY: MOD_RES
<222> LOCATION: (6)..(6)
<223> OTHER INFORMATION: 4-bromobenzoyllysine
<220> FEATURE:
<221> NAME/KEY: MOD_RES
<222> LOCATION: (8)..(8)
<223> OTHER INFORMATION: 4-bromobenzoyllysine

<400> SEQUENCE: 27

Lys Pro Ser Gln Ser Lys Ser Lys Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Benzoyllysine

<400> SEQUENCE: 28

Pro Ser Gln Ser Ser Ser Lys Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(7)
<223> OTHER INFORMATION: 4-bromobenzoyllysine

<400> SEQUENCE: 29

Pro Ser Gln Ser Ser Ser Lys Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Benzoyllysine
<220> FEATURE:
<221> NAME/KEY: MOD_RES
<222> LOCATION: (7)..(7)
<223> OTHER INFORMATION: Benzoyllysine

<400> SEQUENCE: 30

Pro Ser Gln Ser Lys Ser Lys Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-bromobenzoyllysine
<220> FEATURE:
<221> NAME/KEY: MOD_RES
<222> LOCATION: (7)..(7)
<223> OTHER INFORMATION: 4-bromobenzoyllysine

<400> SEQUENCE: 31

Pro Ser Gln Ser Lys Ser Lys Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Benzoyllysine

<400> SEQUENCE: 32

Pro Ser Gln Ser Lys Ser Glu Ala
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 33

Leu Leu Gln Gly Pro Ser Gln Ser Ser Ser Glu Ala
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristoyl group
<220> FEATURE:
<221> NAME/KEY: MOD_RES
<222> LOCATION: (5)..(5)
<223> OTHER INFORMATION: 4-bromobenzoyllysine

<400> SEQUENCE: 34

Pro Ser Gln Ser Lys Ser Glu Ala
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-bromobenzoyllysine

<400> SEQUENCE: 35

Pro Ser Gln Ser Lys Ser Glu Ala
1               5
```

PEPTIDES AND NANOPARTICLES FOR THERAPEUTIC AND DIAGNOSTIC APPLICATIONS

CROSS-REFERENCE TO RELATED APPLICATIONS

This application is a continuation of U.S. patent application Ser. No. 13/195,663 filed Aug. 1, 2011, which is a continuation-in-part National Stage application under 35 U.S.C. §371 of International Application No. PCT/US2010/022598, having an International Filing Date of Jan. 29, 2010, which claims priority to U.S. Provisional Application Ser. No. 61/148,868, filed on Jan. 30, 2009, both of which are incorporated in their entirety by reference herein.

STATEMENT AS TO FEDERALLY FUNDED RESEARCH

This invention was made with government support under Grant Nos. CA78383, HL072178, HL70567, and GM63021 awarded by National Institutes of Health. The government has certain rights in the invention.

TECHNICAL FIELD

This disclosure generally relates to peptides and peptide modified metal nanoparticle bioconjugates useful in therapeutic and diagnostic applications, such as the treatment of cancer.

BACKGROUND

RGS-GAIP-interacting protein C terminus (GIPC) is involved in protein trafficking, endocytosis, and receptor clustering and has been shown to be associated with IGF-1R and EGFR, receptors important for proliferation and anchorage-independent growth of cancerous cells. Knockdown of the GAIP interacting protein (GIPC) has been shown to reduce IGF-1R and EGFR levels in certain cancer cell lines and inhibits proliferation. Although drugs for the treatment of cancer are known, therapeutics that inhibit the function of GIPC would provide additional treatment options to patients.

SUMMARY

Provided herein are compositions and methods useful for treating and diagnosing a variety of diseases, such as cancer. The compositions described herein include peptides having an affinity to the PDZ domain of GIPC/synectin and are useful for treating disease states or conditions that are mediated by GIPC/synectin, such as cancer. In certain embodiments, the peptides are attached, either directly or indirectly via a linker, to a metal nanoparticle to give a bioconjugate. Such bioconjugates can further comprise one or more of a targeting agent (e.g., antibodies or antibody fragment), a masking agent (e.g., PEG or a PEG derivative), or an imaging agent. The peptides and bioconjugates described herein can be used in the treatment and diagnosis of disease, e.g., cancer.

In certain embodiments, provided is a bioconjugate comprising, a metal nanoparticle bound to at least one peptide having a length from 8 to about 30 amino acids, the peptide comprising an amino acid sequence according to Formula I:

$$\text{I} \quad X^1\text{-}X^2\text{-}X^3\text{-}X^4\text{-}X^5\text{-}X^6\text{-}X^7\text{-}X^8 \quad (\text{SEQ ID NO: 1})$$

where:
$X^1$ is proline, 4-hydroxyproline, 4-oxoproline, 3,4-dehydroproline, 4-thiaproline, 4-aminoproline, or pipecolic acid;
each of $X^2$, $X^4$, $X^5$, and $X^6$ independently for each occurrence is serine, homoserine, cysteine, α-methylcysteine, penicillamine, threonine, α-methylthreonine, alanine, allylglycine, benzoyllysine, 4-bromobenzoyllysine, or norvaline;
$X^3$ is glutamine, glutamic acid, aspartic acid, or asparagine;
$X^7$ is glutamine, glutamic acid, aspartic acid, benzoyllysine, 4-bromobenzoyllysine, or asparagine; and
$X^8$ is glycine, alanine, α-aminoisobutyric acid, allylglycine, valine, or norvaline;
or the peptide comprising an amino acid sequence according to Formula II:

$$\text{II} \quad X^1\text{-}X^2\text{-}X^3\text{-}X^4\text{-}X^5\text{-}X^6\text{-}X^7\text{-}X^8 \quad (\text{SEQ ID NO: 2})$$

where:
$X^1$ is ornithine, 4-aminoproline, lysine, or arginine;
$X^2$ is glutamine, glutamic acid, aspartic acid, or asparagine;
$X^3$ is ornithine, lysine, arginine, or 4-aminomethylphenylalanine;
$X^4$ is valine, leucine, tert-leucine, alanine, allylglycine, norvaline, 2-indanylglycine, phenylglycine, propargylglycine, cyclohexylalanine, cyclohexylglycine, or threonine;
$X^5$ is valine, serine, threonine, L-allo-threonine, tert-leucine, penicillamine, leucine, or homoserine;
$X^6$ is serine, homoserine, cysteine, α-methylcysteine, penicillamine, threonine, α-methylthreonine, alanine, allylglycine, or norvaline;
$X^7$ is aspartic acid, glutamic acid, asparagine, glutamine, or sulphouralanine; and
$X^8$ is glycine, alanine, α-aminoisobutyric acid, allylglycine, valine, or norvaline;
where the peptide is optionally modified at its N-terminus or on a side chain with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain embodiments, the metal nanoparticle is a gold, silver, copper, nickel, aluminum, zinc, calcium, platinum, palladium, or iron nanoparticle. In certain embodiments, the metal nanoparticle is a gold nanoparticle.

In certain embodiments, the metal nanoparticle is less than about 70 nanometers, less than about 50 nanometers, less than about 30 nanometers, less than about 10 nanometers, or less than about 5 nanometers in size.

In certain embodiments, the metal nanoparticle is attached directly to the peptide by one or more bonds to the N-terminus of the peptide or to a side chain of the peptide.

In certain embodiments, the nanoparticle is attached to a linker to the peptide, wherein the linker is linked to the N-terminus of the peptide or to a side chain of the peptide. In certain embodiments, the one or more bonds is selected from a covalent bond and a coordinate bond.

In certain embodiments, the linker is attached to the nanoparticle by a covalent bond or a coordinate bond.

In certain embodiments, the linker can be cleaved enzymatically or chemically under physiological conditions.

In certain embodiments, the bioconjugate comprises a peptide modified at its N-terminus or on a side chain with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain embodiments, the bioconjugate comprises a peptide that is modified at its N-terminus or on a side chain with a myristoyl group.

In certain embodiments, the bioconjugate comprises a peptide that is modified at its N-terminus with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain embodiments, the bioconjugate comprises a peptide that is is modified at its N-terminus with a myristoyl group.

In certain embodiments, the peptide comprises an amino acid sequence selected from the group consisting of:

```
                                       (SEQ ID NO: 16)
My-PSQSSSEA, (SEQ ID NO: 17)
My-PSQSSSK(ben)A, (SEQ ID NO: 18)
My-PSQSSSK(4-Br-ben)A, (SEQ ID NO: 19)
My-PSQSK(ben)SK(ben)A, (SEQ ID NO: 20)
My-PSQSK(4-Br-ben)SK(4-Br-ben)A, (SEQ ID NO: 21)
My-PSQSK(ben)SEA, (SEQ ID NO: 34)
My-PSQSK(4-Br-ben)SEA, (SEQ ID NO: 22)
My-LLQGPSQSSSEA, (SEQ ID NO: 23)
My-SESPSASQ, (SEQ ID NO: 24)
My-SPSASK(4-Br-ben)SQ, (SEQ ID NO: 25)
My-K(Fl)PSQSSSEA, (SEQ ID NO: 26)
My-K(Fl)PSQSK(ben)SK(ben)A,
and (SEQ ID NO: 27)
My-K(Fl)PSQSK(4-Br-ben)SK(4-Br-ben)A,
``` wherein K(ben) represents benzoyllysine, K(4-Br-ben) represents 4-bromobenzoyllysine, and My represents a myristoyl group.

In certain embodiments, the peptide comprises an amino acid sequence according to Formula I, wherein $X^1$ is proline, 4-hydroxyproline, 4-oxoproline, 3,4-dehydroproline, or 4-thiaproline; each of $X^2$, $X^4$, $X^5$, and $X^6$ independently for each occurrence is serine, homoserine, cysteine, α-methylcysteine, penicillamine, threonine, or α-methylthreonine; $X^3$ is glutamine or asparagine; $X^7$ is glutamic acid or aspartic acid; and $X^8$ is glycine, alanine, or α-aminoisobutyric acid.

In certain embodiments, the peptide comprises an amino acid sequence according to Formula I, wherein $X^1$ is proline or 3,4-dehydroproline; each of $X^2$, $X^4$, $X^5$, and $X^6$ independently for each occurrence is serine or cysteine; $X^3$ is glutamine; $X^7$ is glutamic acid; and $X^8$ is glycine or alanine.

In certain embodiments, the peptide comprises an amino acid sequence selected from the group consisting of:

```
                                       (SEQ ID NO: 3)
P-S-Q-S-S-S-E-A, (SEQ ID NO: 4)
P-C-Q-S-S-S-E-A, (SEQ ID NO: 5)
P-S-Q-C-S-S-E-A, (SEQ ID NO: 6)
P-S-Q-S-C-S-E-A, (SEQ ID NO: 7)
P-S-Q-S-S-C-E-A, (SEQ ID NO: 8)
K-E-R-L-T-S-D-A, (SEQ ID NO: 9)
K-E-R-L-T-C-D-A, (SEQ ID NO: 10)
K-E-R-L-T-S-D-G, (SEQ ID NO: 11)
K-E-R-L-T-C-D-G, (SEQ ID NO: 28)
P-S-Q-S-S-S-K(ben)-A, (SEQ ID NO: 29)
P-S-Q-S-S-S-K(4-Br-ben)-A, (SEQ ID NO: 30)
P-S-Q-S-K(ben)-S-K(ben)-A, (SEQ ID NO: 31)
P-S-Q-S-K(4-Br-ben)-S-K(4-Br-ben)-A, (SEQ ID NO: 32)
P-S-Q-S-K(ben)-S-E-A, (SEQ ID NO: 33)
L-L-Q-G-P-S-Q-S-S-E-A,
and (SEQ ID NO: 34)
P-S-Q-S-K(4-Br-ben)-S-E-A,
``` wherein K(ben) represents benzoyllysine and K(4-Br-ben) represents 4-bromobenzoyllysine.

Certain embodiments relate to any of the aforementioned embodiments, where the peptide has a length from 8 to about 20 amino acids. Certain embodiments relate to any of the aforementioned embodiments, where the peptide has a length from 8 to about 15 amino acids. Certain embodiments relate to any of the aforementioned embodiments, where the peptide has a length from 8 to about 10 amino acids. Certain embodiments relate to any of the aforementioned embodiments, where the peptide is 8 amino acids in length.

In certain embodiments, the peptide comprises an amino acid sequence according to Formula II, wherein $X^1$ is ornithine, lysine, or arginine; $X^2$ is glutamic acid, aspartic acid; $X^3$ is ornithine, lysine, or arginine; $X^4$ is valine, leucine, tert-leucine, alanine, allylglycine, or norvaline; $X^5$ is serine, threonine, or L-allo-threonine; $X^6$ is serine, homoserine, cysteine, α-methylcysteine, penicillamine, threonine, or α-methylthreonine; $X^7$ is aspartic acid or glutamic acid; and $X^8$ is glycine or alanine.

In certain embodiments, the peptide comprises an amino acid sequence according to Formula II, wherein $X^1$ is lysine or arginine; $X^2$ is glutamic acid or aspartic acid; $X^3$ is lysine or arginine; $X^4$ is leucine; $X^5$ is threonine; $X^6$ is cysteine or serine; $X^7$ is aspartic acid or glutamic acid; and $X^8$ is glycine or alanine.

Certain embodiments relate to any of the aforementioned embodiments, where the peptide has a length from 8 to about 20 amino acids. Certain embodiments relate to any of the aforementioned embodiments, where the the peptide has a length from 8 to about 15 amino acids. Certain embodiments relate to any of the aforementioned embodiments, where the peptide has a length from 8 to about 10 amino acids. Certain embodiments relate to any of the aforementioned embodiments, where the peptide is 8 amino acids in length.

In certain embodiments, the bioconjugate further comprises one or more targeting agents attached to the metal nanoparticle. In certain embodiments, the targeting agent comprises an antibody or fragment thereof. In certain embodiments, the antibody is an anti-EGFR antibody or anti-VEGF antibody.

In certain embodiments, the bioconjugate further comprises one or more masking agents attached to the metal nanoparticle. In certain embodiments, the masking agent is PEG or a PEG derivative.

In certain embodiments, the bioconjugate further comprises a second therapeutic agent attached to the nanoparticle. In certain embodiments, the second therapeutic agent is selected from the group consisting of gemcitabine, rapamycin, capecitabine, 5-fluorouracil, floxuridine, doxifluridine, ratitrexed, methotrexate, trimetrexate, thapsigargin, taxol, paclitaxel, docetaxel, actinomycin D, dactinomycin, mercaptopurine, thioguanine, lovastatin, cytosine arabinoside, fludarabine, hydroxyurea, cytarabine, cytarabine, teniposide, topotecan, 9-aminocamptothecin, camptoirinotecan, crisnatol, busulfan, mytomycin C, treosulfan, staurosporine, 1-methyl-4-phenylpyridinium, mercaptopurine, thioguanine, cyclophosphamide, ifosfamide, EB 1089, CB 1093, KH 1060, carmustine, lomustine, mycophenolic acid, tiazofurin, ribavirin, EICAR, cisplatin, carboplatin, oxaliplatin, bevacizumab, mitomycin, dacarbazine, procarbizine, etoposides, prednisolone, trofosfamide, chlorambucil, melphalan, estramustine, dexamethasone, cytarbine, campathecins, bleomycin, doxorubicin, idarubicin, daunorubicin, doxorubicin, epirubicin, pirarubicin, zorubicin, verapamil, mitoxantrone, temozolomide, dactinomycin, plicamycin, bleomycin A2, bleomycin B2, peplomycin, asparaginase, vinblastine, vincristine, vindesine, vinorelbine, imatinib, thalidomide, leucovirin, deferoxamine, lenalidomide, bortezomib, erlotinib, gefitinib, sorafenib, erbitux, and sutinib.

In certain embodiments, the bioconjugate further comprises an imaging agent selected from the group consisting of an MR imaging agent, a radio-imaging agent, an X-ray imaging agent, and a near-IR imaging agent attached to the metal nanoparticle.

In certain embodiments, the imaging agent is selected from the group consisting of a chelating ligand selected from the group consisting of DTPA, DOTA, DOTMA, DTPA-BMA, DOTAGA, and HP-DO3A.

Also provided herein is a method for imaging a tumor in a patient, the method comprising:
a) administering to the patient a pharmaceutically acceptable composition comprising a bioconjugate having an imaging agent; and
b) imaging the patient.

In certain embodiments, the tumor expresses GIPC.

Certain embodiments provide a peptide having a length from 8 to about 30 amino acids, the peptide comprising an amino acid sequence according to Formula I:

$$\text{I} \quad\quad\quad (\text{SEQ ID NO: 1})$$
$$X^1\text{-}X^2\text{-}X^3\text{-}X^4\text{-}X^5\text{-}X^6\text{-}X^7\text{-}X^8$$

where:
$X^1$ is proline, 4-hydroxyproline, 4-oxoproline, 3,4-dehydroproline, 4-thiaproline, 4-aminoproline, or pipecolic acid;
each of $X^2$, $X^4$, $X^5$, and $X^6$ independently for each occurrence is serine, homoserine, cysteine, α-methylcysteine, penicillamine, threonine, α-methylthreonine, alanine, allylglycine, benzoyllysine, 4-bromobenzoyllysine, or norvaline;
$X^3$ is glutamine, glutamic acid, aspartic acid, or asparagine;
$X^7$ is glutamine, glutamic acid, aspartic acid, benzoyllysine, 4-bromobenzoyllysine, or asparagine; and
$X^8$ is glycine, alanine, α-aminoisobutyric acid, allylglycine, valine, or norvaline;

or the peptide comprising an amino acid sequence according to Formula II:

$$\text{II} \quad\quad\quad (\text{SEQ ID NO: 2})$$
$$X^1\text{-}X^2\text{-}X^3\text{-}X^4\text{-}X^5\text{-}X^6\text{-}X^7\text{-}X^8$$

where:
$X^1$ is ornithine, 4-aminoproline, lysine, or arginine;
$X^2$ is glutamine, glutamic acid, aspartic acid, or asparagine;
$X^3$ is ornithine, lysine, arginine, or 4-aminomethylphenylalanine;
$X^4$ is valine, leucine, tert-leucine, alanine, allylglycine, norvaline, 2-indanylglycine, phenylglycine, propargylglycine, cyclohexylalanine, cyclohexylglycine, or threonine;
$X^5$ is valine, serine, threonine, L-allo-threonine, tert-leucine, penicillamine, leucine, or homoserine;
$X^6$ is serine, homoserine, cysteine, α-methylcysteine, penicillamine, threonine, α-methylthreonine, alanine, allylglycine, or norvaline
$X^7$ is aspartic acid, glutamic acid, asparagine, glutamine, or sulphouralanine; and
$X^8$ is glycine, alanine, α-aminoisobutyric acid, allylglycine, valine, or norvaline.

In certain embodiments, the peptide comprises an amino acid sequence according to Formula I, wherein
$X^1$ is proline, 4-hydroxyproline, 4-oxoproline, 3,4-dehydroproline, 4-thiaproline, 4-aminoproline, or pipecolic acid;

each of $X^2$, $X^4$, $X^5$, and $X^6$ independently for each occurrence is serine, homoserine, cysteine, α-methylcysteine, penicillamine, threonine, α-methylthreonine, alanine, allylglycine, or norvaline;

$X^3$ is glutamine, glutamic acid, aspartic acid, or asparagine;

$X^7$ is glutamine, glutamic acid, aspartic acid, or asparagine; and $X^8$ is glycine, alanine, α-aminoisobutyric acid, allylglycine, valine, or norvaline;

provided that when $X^1$ is proline; each of $X^2$, $X^4$, $X^5$, and $X^6$ is serine; and $X^7$ is glutamic acid; then $X^8$ is not glycine.

In certain embodiments, the peptide comprises a peptide that is modified at its N-terminus or on a side chain with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain embodiments, the peptide comprises a peptide that is modified at its N-terminus or on a side chain with a myristoyl group.

In some embodiments, the peptide comprises a peptide that is modified at its N-terminus with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain embodiments, the peptide comprises a peptide that is modified at its N-terminus with a myristoyl group.

In certain embodiments, the peptide comprises an amino acid sequence selected from the group consisting of:

```
                                          (SEQ ID NO: 16)
My-PSQSSSEA, (SEQ ID NO: 17)
My-PSQSSSK(ben)A, (SEQ ID NO: 18)
My-PSQSSSK(4-Br-ben)A, (SEQ ID NO: 19)
My-PSQSK(ben)SK(ben)A, (SEQ ID NO: 20)
My-PSQSK(4-Br-ben)SK(4-Br-ben)A, (SEQ ID NO: 21)
My-PSQSK(ben)SEA, (SEQ ID NO: 34)
My-PSQSK(4-Br-ben)SEA, (SEQ ID NO: 22)
My-LLQGPSQSSSEA, (SEQ ID NO: 23)
My-SESPSASQ, (SEQ ID NO: 24)
My-SPSASK(4-Br-ben)SQ, (SEQ ID NO: 25)
My-K(Fl)PSQSSSEA, (SEQ ID NO: 26)
My-K(Fl)PSQSK(ben)SK(ben)A,
and
```

```
                                          (SEQ ID NO: 27)
My-K(Fl)PSQSK(4-Br-ben)SK(4-Br-ben)A,
``` wherein K(ben) represents benzoyllysine, K(4-Br-ben) represents 4-bromobenzoyllysine, and My represents a myristoyl group.

In certain embodiments, $X^1$ is proline, 4-hydroxyproline, 4-oxoproline, 3,4-dehydroproline, or 4-thiaproline; each of $X^2$, $X^4$, $X^5$, and $X^6$ independently for each occurrence is serine, homoserine, cysteine, α-methylcysteine, penicillamine, threonine, or α-methylthreonine; $X^3$ is glutamine or asparagine; $X^7$ is glutamic acid or aspartic acid; and $X^8$ is glycine, alanine, or α-aminoisobutyric acid.

In certain embodiments, $X^1$ is proline or 3,4-dehydroproline; each of $X^2$, $X^4$, $X^5$, and $X^6$ independently for each occurrence is serine or cysteine; $X^3$ is glutamine; $X^7$ is glutamic acid; and $X^8$ is glycine or alanine.

In certain embodiments, the peptide comprises an amino acid sequence selected from the group consisting of:

```
                                          (SEQ ID NO: 3)
P-S-Q-S-S-S-E-A, (SEQ ID NO: 4)
P-C-Q-S-S-S-E-A, (SEQ ID NO: 5)
P-S-Q-C-S-S-E-A, (SEQ ID NO: 6)
P-S-Q-S-C-S-E-A, (SEQ ID NO: 7)
P-S-Q-S-S-C-E-A, (SEQ ID NO: 8)
K-E-R-L-T-S-D-A, (SEQ ID NO: 9)
K-E-R-L-T-C-D-A, (SEQ ID NO: 10)
K-E-R-L-T-S-D-G, (SEQ ID NO: 11)
K-E-R-L-T-C-D-G, (SEQ ID NO: 28)
P-S-Q-S-S-S-K(ben)-A, (SEQ ID NO: 29)
P-S-Q-S-S-S-K(4-Br-ben)-A, (SEQ ID NO: 30)
P-S-Q-S-K(ben)-S-K(ben)-A, (SEQ ID NO: 31)
P-S-Q-S-K(4-Br-ben)-S-K(4-Br-ben)-A, (SEQ ID NO: 32)
P-S-Q-S-K(ben)-S-E-A, (SEQ ID NO: 33)
L-L-Q-G-P-S-Q-S-S-E-A,
and (SEQ ID NO: 34)
P-S-Q-S-K(4-Br-ben)-S-E-A,
``` wherein K(ben) represents benzoyllysine and K(4-Br-ben) represents 4-bromobenzoyllysine.

In certain embodiments, the peptide comprises an amino acid sequence according to Formula II, where $X^1$ is ornithine, lysine, or arginine; $X^2$ is glutamic acid, aspartic acid; $X^3$ is ornithine, lysine, or arginine; $X^4$ is valine, leucine, tert-leucine, alanine, allylglycine, or norvaline; $X^5$ is serine, threonine, or L-allo-threonine; $X^6$ is serine, homoserine, cysteine, α-methylcysteine, penicillamine, threonine, or α-methylthreonine; $X^7$ is aspartic acid or glutamic acid; and $X^8$ is glycine or alanine.

In certain embodiments, the peptide comprises an amino acid sequence according to Formula II, wherein $X^1$ is lysine or arginine; $X^2$ is glutamic acid or aspartic acid; $X^3$ is lysine or arginine; $X^4$ is leucine; $X^5$ is threonine; $X^6$ is cysteine or serine; $X^7$ is aspartic acid or glutamic acid; and $X^8$ is glycine or alanine.

Certain embodiments relate to any of the aforementioned peptides, where the peptide has a length from 8 to about 20 amino acids. Certain embodiments relate to any of the aforementioned peptides, where the the peptide has a length from 8 to about 15 amino acids. Certain embodiments relate to any of the aforementioned peptides, where the peptide has a length from 8 to about 10 amino acids. Certain embodiments relate to any of the aforementioned peptides, where the peptide is 8 amino acids in length.

Certain embodiments provide a pharmaceutical composition comprising the bioconjugate of claim 1 and at least one pharmaceutically acceptable excipient.

In certain embodiments, the pharmaceutical composition comprises any of the aforementioned peptides of and at least one pharmaceutically acceptable excipient.

Certain embodiments provide a method for treating or ameliorating one or more symptoms of cancer comprising administering to a patient in need thereof a therapeutically effective amount of any of the aforementioned bioconjugates or any of the aforementioned peptides.

In certain embodiments, the cancer over-expresses GIPC. In certain embodiments, the cancer is a pancreatic cancer, a gastric cancer, or a breast cancer.

In certain embodiments, the method of treating or ameliorating one or more symptoms of cancer further comprises co-administering a second chemotherapeutic agent. In certain embodiments, the second chemotherapeutic agent is selected from the group consisting of gemcitabine, rapamycin, capecitabine, 5-fluorouracil, floxuridine, doxifluridine, ratitrexed, methotrexate, trimetrexate, thapsigargin, taxol, paclitaxel, docetaxel, actinomycin D, dactinomycin, mercaptopurine, thioguanine, lovastatin, cytosine arabinoside, fludarabine, hydroxyurea, cytarabine, cytarabine, teniposide, topotecan, 9-aminocamptothecin, camptoirinotecan, crisnatol, busulfan, mytomycin C, treosulfan, staurosporine, 1-methyl-4-phenylpyridinium, mercaptopurine, thioguanine, cyclophosphamide, ifosfamide, EB 1089, CB 1093, KH 1060, carmustine, lomustine, mycophenolic acid, tiazofurin, ribavirin, EICAR, cisplatin, carboplatin, oxaliplatin, bevacizumab, mitomycin, dacarbazine, procarbizine, etoposides, prednisolone, trofosfamide, chlorambucil, melphalan, estramustine, dexamethasone, cytarbine, campathecins, bleomycin, doxorubicin, idarubicin, daunorubicin, doxorubicin, epirubicin, pirarubicin, zorubicin, verapamil, mitoxantrone, temozolomide, dactinomycin, plicamycin, bleomycin A2, bleomycin B2, peplomycin, asparaginase, vinblastine, vincristine, vindesine, vinorelbine, imatinib, thalidomide, leucovirin, deferoxamine, lenalidomide, bortezomib, erlotinib, gefitinib, sorafenib, erbitux, and sutinib.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 (A) shows bioluminescence images after n-Luciferin application. GIPC/synectin expression was reduced by lentiviral shRNA, in the control group an empty Luc vector was used. FIG. 1 (B) is a Kaplan Meyer diagram showing the percentage of tumor free mice in relation to the time after orthotopic tumor transplantation. 10 nude mice were transplanted orthotopically with GIPC deficient MIAPaCa2 cells, the other 10 nude mice were transplanted with MIAPaCa2 which are transduced with an empty luciferase vector. The difference is significant (p=0.04; univariate log rank test). Tumor take rates: day 19 post transplantation: control 5 out of 10; GIPC shRNA 0 out of 10; day 24 post transplantation: control 6 out of 10; GIPC shRNA 3 out of 10; day 39 post transplantation (end of experiment): control 8 out of 10; GIPC shRNA 4 out of 10. FIG. 1 (C) is box plots of the tumor volume after implantation of AsPC1 cells in the pancreas of 20 nude mice. 10 mice received AsPC1 cells that were treated with shRNA (t) and 10 mice were transplanted with AsPC1 cells that were transduced with an empty Luc vector (c). After 14 days mice were sacrificed and tumor volume was measured. The group which received GIPC deficient AsPC1 cells has a significantly smaller tumor volume than the control group. Mean in the tgroup (GIPC shRNA): 402 mm3; 95% CI=137 mm3-360 mm3; Mean in the c-group (control): 498 mm3; 95% CI=302 mm3-501 mm3; P=0.03 (t vs c; Mann-Whitney test)

FIG. 2 (C) shows a fluorescent microscopy image after excitation of MIAPaCa2 pancreatic cancer cells treated with FITC labeled blocking peptide. The image (100× magnification) demonstrates the entry of the blocking peptide into the cancer cells. FIG. 2(D) shows a MTS viability assay after 24 h treatment with PSQSSSEA (SEQ ID NO: 3) in different concentrations. The assay shows a clear reduction of viability at a dose of 100 μM in MIAPaCa2 and AsPC1 cells, in PANC1 cells the viability was clearly reduced at a dose of 150 μM. FIG. 2(E) shows thymidine incorporation assay after 24 h of peptide treatment. FIG. 2(F) shows a MTS colorimetric viability assay after treatment of peptide (200 μM, 100 μM, control peptide). The assay showed a dose dependent inhibition of viability after peptide treatment.

FIG. 3(C) shows evaluation of the proliferation rate in the paraffin embedded tumor tissue by staining for Ki67. Nuclear staining per 1000 cells was counted in representative tumors. The difference between treated tumors (n=6) and control tumors (n=7) is significant (p=0.0129; t-test). FIG. 3(D) shows immunohistochemistry of selected tumors for the proliferation marker Ki67 after peptide treatment and after control PBS treatment. (Oil immersion with magnification ×100; Zeiss Axioplan 2).

FIG. 4(A) shows an immunoblot against IGF-1R after immunoprecipitation for FLAG (IP:Flag IB:IGF-1R). 48 h before harvesting protein MIA-PaCa2 cells were transiently transfected with FLAG tagged wild type GIPC/Synectin. Cells were treated with 100 µM of PSQSSSEA (SEQ ID NO: 3) or the control peptide dissolved in DMSO. Proteasome inhibitor was used to sustain IGF-1R expression by inhibiting octapeptide-induced degradation. This immunoblot demonstrated that the blocking peptide is effective in reducing the association between GIPC/synectin and IGF-1R. The Western Blot for FLAG showed equal transfection efficiency. FIG. 4(B) shows Western Blot analysis of cells treated with PSQSSSEA (SEQ ID NO: 3) (200 µM, 100 µM, control peptide) overnight after incubation with 50 ng/ml rhIGF-1. The analysis showed a downregulation of IGF-1R. FIG. 4(C) shows evaluation of IGF-1R protein levels by immunoblot after treatment with PSQSSSEA (SEQ ID NO: 3) and rhIGF-1. Before harvesting of the protein 25 µM proteasome inhibitor was added for 2 hours.

FIG. 5(A) shows immunoblot analysis of tumor samples with and without GIPC/synectin knockdown. Protein lysates were prepared from tumor tissue and evaluated for IGF-1R, GIPC and actin expression. FIG. 5(B) shows box plots of the densitometry evaluation of an anti-IGF-1R immunoblot (see FIG. 5c) of tissue lysates after peptide and control treatment. The treated tumors show significantly lower amount of IGF-1R as compared to the controls (p=0.02 student's t-test). FIG. 5(C) shows a Western Blot of the tumor tissues for IGF-1R with and without peptide treatment. Actin serves as a loading control.

DETAILED DESCRIPTION

Figure 1A:
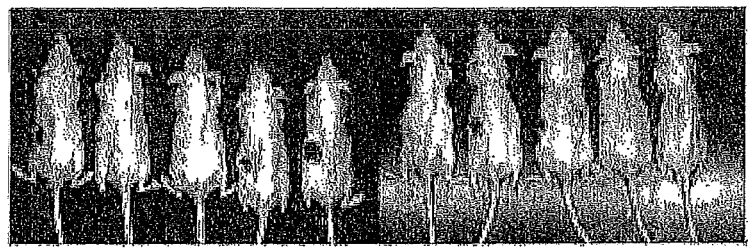
FIGS. 1(A) through 1(C) show lentiviral GIPC/synectin shRNA transduction inhibiting tumor cell growth in vivo.
Figure 1A:
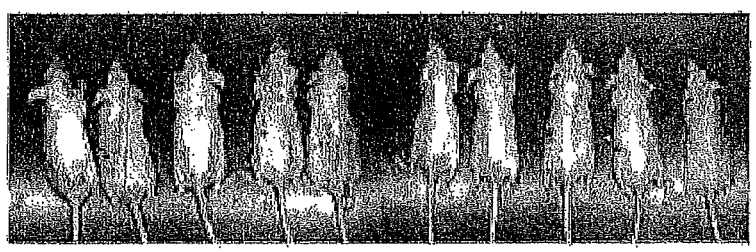
Figure 1A:
Figure 1A:
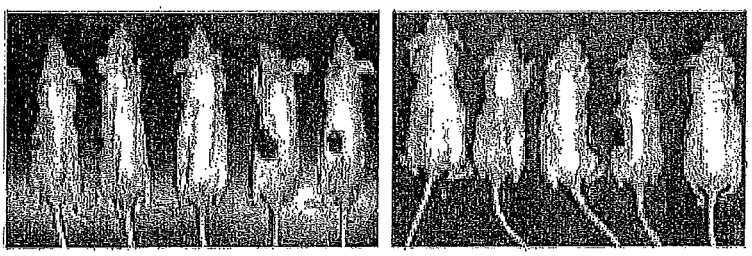

The inventors have discovered that peptides comprising an amino acid sequence according to Formula I and Formula II can inhibit the function of GIPC/synectin and are useful in the treatment and diagnosis of various diseases that are mediated by GIPC/synectin, such as cancer.

In certain instances, the peptide can comprise an amino acid sequence according to Formula I:

$$\text{I}$$
$$X^1\text{-}X^2\text{-}X^3\text{-}X^4\text{-}X^5\text{-}X^6\text{-}X^7\text{-}X^8 \quad \text{(SEQ ID NO: 1)}$$

where $X^1$ is proline, 4-hydroxyproline, 4-oxoproline, 3,4-dehydroproline, 4-thiaproline, 4-aminoproline, or pipecolic acid; each of $X^2$, $X^4$, $X^5$, and $X^6$ independently for each occurrence is serine, homoserine, cysteine, α-methylcysteine, penicillamine, threonine, α-methylthreonine, alanine, allylglycine, benzoyllysine, 4-bromobenzoyllysine, or norvaline; $X^3$ is glutamine, glutamic acid, aspartic acid, or asparagine; $X^7$ is glutamine, glutamic acid, aspartic acid, benzoyllysine, 4-bromobenzoyllysine, or asparagine; and $X^8$ is glycine, alanine, α-aminoisobutyric acid, allylglycine, valine, or norvaline.

In certain instances, the peptide comprises an amino acid sequence according to Formula I, wherein $X^1$ is proline, 4-hydroxyproline, 4-oxoproline, 3,4-dehydroproline, or 4-thiaproline; each of $X^2$, $X^4$, $X^5$, and $X^6$ independently for each occurrence is serine, homoserine, cysteine, α-methylcysteine, penicillamine, threonine, or α-methylthreonine; $X^3$ is glutamine or asparagine; $X^7$ is glutamic acid or aspartic acid; and $X^8$ is glycine, alanine, or α-aminoisobutyric acid.

In certain instances, the peptide comprises an amino acid sequence according to Formula I, wherein $X^1$ is proline or 3,4-dehydroproline; each of $X^2$, $X^4$, $X^5$, and $X^6$ independently for each occurrence is serine or cysteine; $X^3$ is glutamine; $X^7$ is glutamic acid; and $X^8$ is glycine or alanine.

In certain instances, the amino acid sequence is selected from the group consisting of:

|  |  |
|---|---|
| P-S-Q-S-S-S-E-A, | (SEQ ID NO: 3) |
| P-C-Q-S-S-S-E-A, | (SEQ ID NO: 4) |
| P-S-Q-C-S-S-E-A, | (SEQ ID NO: 5) |
| P-S-Q-S-C-S-E-A, | (SEQ ID NO: 6) |
| P-S-Q-S-S-C-E-A, | (SEQ ID NO: 7) |
| K-E-R-L-T-S-D-A, | (SEQ ID NO: 8) |
| K-E-R-L-T-C-D-A, | (SEQ ID NO: 9) |
| K-E-R-L-T-S-D-G, | (SEQ ID NO: 10) |
| K-E-R-L-T-C-D-G, | (SEQ ID NO: 11) |
| P-S-Q-S-S-S-K(ben)-A, | (SEQ ID NO: 28) |
| P-S-Q-S-S-S-K(4-Br-ben)-A, | (SEQ ID NO: 29) |
| P-S-Q-S-K(ben)-S-K(ben)-A, | (SEQ ID NO: 30) |
| P-S-Q-S-K(4-Br-ben)-S-K(4-Br-ben)-A, | (SEQ ID NO: 31) |
| P-S-Q-S-K(ben)-S-E-A, | (SEQ ID NO: 32) |
| L-L-Q-G-P-S-Q-S-S-E-A, and | (SEQ ID NO: 33) |
| P-S-Q-S-K(4-Br-ben)-S-E-A, | (SEQ ID NO: 34) | wherein K(ben) represents benzoyllysine and K(4-Br-ben) represents 4-bromobenzoyllysine.

In certain instances, the peptide can comprise an amino acid sequence according to Formula II:

$$X^1\text{-}X^2\text{-}X^3\text{-}X^4\text{-}X^5\text{-}X^6\text{-}X^7\text{-}X^8 \quad \text{II}$$
(SEQ ID NO: 2)

where $X^1$ is ornithine, 4-aminoproline, lysine, or arginine; $X^2$ is glutamine, glutamic acid, aspartic acid, or asparagine; $X^3$ is ornithine, lysine, arginine, or 4-aminomethylphenylalanine; $X^4$ is valine, leucine, tert-leucine, alanine, allylglycine, norvaline, 2-indanyiglycine, phenylglycine, propargylglycine, cyclohexylalanine, cyclohexylglycine, or threonine; $X^5$ is valine, serine, threonine, L-allo-threonine, tert-leucine, penicillamine, leucine, or homoserine; $X^6$ is serine, homoserine, cysteine, α-methylcysteine, penicillamine, threonine, α-methylthreonine, alanine, allylglycine, or norvaline; $X^7$ is aspartic acid, glutamic acid, asparagine, glutamine, or sulphouralanine; and $X^8$ is glycine, alanine, α-aminoisobutyric acid, allylglycine, valine, or norvaline.

In certain instances, the peptide comprises an amino acid sequence that is modified at its N-terminus or on a side chain with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain instances, the peptide comprises an amino acid sequence that is modified at its N-terminus or on a side chain with a myristoyl group.

In some instances, the peptide comprises an amino acid sequence that is modified at its N-terminus with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

In certain instances, the peptide comprises an amino acid sequence that is modified at its N-terminus with a myristoyl group.

In certain instances, the peptide comprises an amino acid sequence selected from the group consisting of:

My-PSQSSSEA, (SEQ ID NO: 16)

My-PSQSSSK(ben)A, (SEQ ID NO: 17)

My-PSQSSSK(4-Br-ben)A, (SEQ ID NO: 18)

My-PSQSK(ben)SK(ben)A, (SEQ ID NO: 19)

My-PSQSK(4-Br-ben)SK(4-Br-ben)A, (SEQ ID NO: 20)

My-PSQSK(ben)SEA, (SEQ ID NO: 21)

My-PSQSK(4-Br-ben)SEA, (SEQ ID NO: 34)

My-LLQGPSQSSSEA, (SEQ ID NO: 22)

My-SESPSASQ, (SEQ ID NO: 23)

My-SPSASK(4-Br-ben)SQ, (SEQ ID NO: 24)

My-K(FI)PSQSSSEA, (SEQ ID NO: 25)

My-K(FI)PSQSK(ben)SK(ben)A, and (SEQ ID NO: 26)

My-K(FI)PSQSK(4-Br-ben)SK(4-Br-ben)A, (SEQ ID NO: 27)

wherein K(ben) represents benzoyllysine, K(4-Br-ben) represents 4-bromobenzoyllysine, and My represents a myristoyl group.

In certain instances, the peptide comprises an amino acid sequence according to Formula II, where $X^1$ is ornithine, lysine, or arginine; $X^2$ is glutamic acid or aspartic acid; $X^3$ is ornithine, lysine, or arginine; $X^4$ is valine, leucine, tert-leucine, alanine, allylglycine, or norvaline; $X^5$ is serine, threonine, or L-allo-threonine; $X^6$ is serine, homoserine, cysteine, α-methylcysteine, penicillamine, threonine, or α-methylthreonine; $X^7$ is aspartic acid or glutamic acid; and $X^8$ is glycine or alanine.

In certain instances, the peptide comprises an amino acid sequence according to Formula II, wherein $X^1$ is lysine or arginine; $X^2$ is glutamic acid or aspartic acid; $X^3$ is lysine or arginine; $X^4$ is leucine; $X^5$ is threonine; $X^6$ is cysteine or serine; $X^7$ is aspartic acid or glutamic acid; and $X^8$ is glycine or alanine.

In instances where the amino acid sequence according to Formula I and II includes amino acid(s) containing one or more stereocenters, the amino acid(s) can be the naturally occurring enantiomer (generally, the levorotatory enantiomer) or the unnatural enantiometer, and combinations thereof.

The peptide can have a length from 8 to about 50 amino acids. In certain instances, the length of the peptide is from 8 to about 40 amino acids, from 8 to about 30 amino acids, from 8 to about 20 amino acids, from 8 to about 15 amino acids, from 8 to about 10 amino acids, or has a length of 8 amino acids.

In certain instances, the amino acid sequence is selected from the group consisting of:

P-S-Q-S-S-S-E-A, (SEQ ID NO: 3)

P-C-Q-S-S-S-E-A, (SEQ ID NO: 4)

P-S-Q-C-S-S-E-A, (SEQ ID NO: 5)

P-S-Q-S-C-S-E-A, (SEQ ID NO: 6)

P-S-Q-S-S-C-E-A, (SEQ ID NO: 7)

K-E-R-L-T-S-D-A, (SEQ ID NO: 8)

K-E-R-L-T-C-D-A, (SEQ ID NO: 9)

```
                                    (SEQ ID NO: 10)
K-E-R-L-T-S-D-G, (SEQ ID NO: 11)
K-E-R-L-T-C-D-G, (SEQ ID NO: 28)
P-S-Q-S-S-S-K(ben)-A, (SEQ ID NO: 29)
P-S-Q-S-S-S-K(4-Br-ben)-A, (SEQ ID NO: 30)
P-S-Q-S-K(ben)-S-K(ben)-A, (SEQ ID NO: 31)
P-S-Q-S-K(4-Br-ben)-S-K(4-Br-ben)-A, (SEQ ID NO: 32)
P-S-Q-S-K(ben)-S-E-A, (SEQ ID NO: 33)
L-L-Q-G-P-S-Q-S-S-S-E-A,
and (SEQ ID NO: 34)
P-S-Q-S-K(4-Br-ben)-S-E-A,
``` wherein K(ben) represents benzoyllysine and K(4-Br-ben) represents 4-bromobenzoyllysine.

The peptides described herein can be further chemically modified to improve, for example, solubility, permeability, circulation half-life, metabolic stability, absorption, and distribution, using techniques well-known to those of ordinary skill in the art. In certain instances, such modifications can be accomplished by incorporating a chemical moiety capable of modifying one the aforementioned parameters, at one or more positions on the peptide (e.g., the N-terminal amine, the C-terminal carboxylate, or at functionality present on a side chain, such as an alcohol, carboxylic acid, amine, amide, etc).

Chemical groups added to the peptide to modify the peptide can be permanent or can be labile, e.g., can be cleaved, partially or entirely, enzymatically or chemically under physiological conditions.

In certain instances, the peptides described herein are modified at their N-terminus, C-terminus, or a side chain with a chemical moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group.

The peptides described herein may contain a basic functional group, such as amino or alkylamino, and are thus capable of forming pharmaceutically acceptable salts with pharmaceutically acceptable acids. The term "pharmaceutically acceptable salts" in this respect, includes relatively non-toxic, inorganic and organic acid addition salts of the peptides described herein. Representative salts include salts derived from suitable inorganic and organic acids, e.g., hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like (see, for example, Berge et al. (1977) "Pharmaceutical Salts", J. Pharm. Sci. 66:1-19)

The peptides described herein can be synthesized using well known techniques in the art, e.g., using an automated synthesizer.

In certain cases, the peptides described herein may contain one or more acidic functional groups and, thus, are capable of forming pharmaceutically-acceptable salts with pharmaceutically-acceptable bases. The term "pharmaceutically-acceptable salts" in these instances includes relatively non-toxic, inorganic and organic base addition salts of the peptides described herein. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

The efficacy and circulation time of the peptides described herein can be improved by attaching the peptide to a metal nanoparticle to form a bioconjugate. The peptide can be attached directly or indirectly (i.e., via a linker) to the surface of the metal nanoparticle. The metal nanoparticle can be any metal including, but not limited to gold, silver, copper, nickel, aluminum, zinc, calcium, platinum, palladium, or iron.

The metal nanoparticle can be any size and shape. For example, the metal nanoparticle can be substantially sphere-shaped or substantially rod-shaped. In certain instances, the bioconjugate compositions provided herein can include bioconjugates comprising nanoparticles of substantially the same shape and/or size, or mixtures of nanoparticles of different sizes and shapes.

Metal nanoparticles useful in the compositions and methods described herein can be less than 100 nanometers, less than 90 nanometers, less than 80 nanometers, less than 70 nanometers, less than 60 nanometers, less than 50 nanometers, less than 40 nanometers, less than 30 nanometers, less than 10 nanometers, or less than 5 nanometers. In certain instances the metal nanoparticle is about 1 nanometer to about 5 nanometers, 1 nanometer to about 10 nanometers, 1 nanometer to about 15 nanometers, or 1 nanometer to about 20 nanometers.

Methods for making colloidal metal nanoparticles, including gold colloidal nanoparticles from $HAuCl_4$, are known to those having ordinary skill in the art. For example, the methods described herein as well as those described elsewhere (e.g., U.S. Publication Nos. 2001/005581; 2003/0118657; 2003/0053983; and 2006/022295) can be used to make metal nanoparticles.

In certain instances, one or more of the peptides described herein are attached directly to the nanoparticle. In such instances, the nanoparticle can be attached via a covalent bond, a coordinative bond or covalent bond. The metal nanoparticle can be attached to the peptide at one or more positions at any where along the length of the peptide. For example, the nanoparticle can be attached at the N-terminal of the peptide, the C-terminal of the peptide, at functionality present on amino acid side chains (e.g., carboxylic acids, alcohols, thiols, thioethers, amides, amines, guanidines, aromatic rings (e.g., via a cation/metal π interaction), and heteroaryls), and/or one or more functional groups present along the peptide backbone (e.g., amides).

In certain instances, the bioconjugates described herein can comprise a peptide modified at its N-terminus or on a side chain with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group. For example, a bioconjugate can comprise a peptide that is modified at its N-terminus or on a side chain with a myristoyl group.

In other instances, the bioconjugates described herein can comprise a peptide that is modified at its N-terminus with a moiety selected from the group consisting of an acetyl group, a propanoyl group, a butyryl group, a valeroyl group, a hexanoyl group, an octanoyl group, a decanoyl group, a myristoyl group, a palmitoyl group, a heptadecanoyl group, a stearoyl group, an arachidoyl group, a behenoyl group, a lignoceroyl group, biotin, and a fluorescein group. For example, a bioconjugate can comprise a peptide that is modified at its N-terminus with a myristoyl group.

In certain instances, a bioconjugate can comprise a peptide with an amino acid sequence selected from the group consisting of:

My-PSQSSSEA, (SEQ ID NO: 16)

My-PSQSSSK(ben)A, (SEQ ID NO: 17)

My-PSQSSSK(4-Br-ben)A, (SEQ ID NO: 18)

My-PSQSK(ben)SK(ben)A, (SEQ ID NO: 19)

My-PSQSK(4-Br-ben)SK(4-Br-ben)A, (SEQ ID NO: 20)

My-PSQSK(ben)SEA, (SEQ ID NO: 21)

My-PSQSK(4-Br-ben)SEA, (SEQ ID NO: 34)

My-LLQGPSQSSSEA, (SEQ ID NO: 22)

My-SESPSASQ, (SEQ ID NO: 23)

My-SPSASK(4-Br-ben)SQ, (SEQ ID NO: 24)

My-K(Fl)PSQSSSEA, (SEQ ID NO: 25)

My-K(Fl)PSQSK(ben)SK(ben)A, and (SEQ ID NO: 26)

My-K(Fl)PSQSK(4-Br-ben)SK(4-Br-ben)A, (SEQ ID NO: 27)

wherein K(ben) represents benzoyllysine, K(4-Br-ben) represents 4-bromobenzoyllysine, and My represents a myristoyl group.

The peptides described herein can be attached to the metal nanoparticles via a linker. Suitable linkers comprise a first chemical moiety capable of forming a coordinative or covalent bond with a metal nanoparticle, e.g., an amino, thiol, carboxyl or hydroxyl, thio-carboxyl, dithio-carboxyl, thioether, or hydroxylamine, and a second chemical moiety that can be attached to the peptide via a chemical bond.

In certain instances, between the two chemical moieties of the linker there is a bridging molecule of suitable length, e.g., between 1 atom and 100 atoms in length (e.g., 2, 3, 4, 5, 6, 7, 8, 9, or 10 atoms). The bridging molecule can be a linear or a branched alkane chain, alkene chain, alkyne chain, or a polymer, e.g., homopolymers or random copolymers and derivatives thereof selected from the group consisting of alkylene glycol homopolymers, alkylene glycol copolymers, polyvinyl alcohol, polyvinyl pyrrolidone, poly-1,3-dioxolane, poly-1,3,6-trioxane, ethylene/maleic anhydride copolymer, and polyaminoacids. In certain instances, the bridging molecule can be substituted with one or more functional groups including ketone, ether, ester, amide, alcohol, amine, urea, thiourea, sulfoxide, sulfone, sulfonamide, and disulfide functionalities. In certain instances, the bridging molecule is PEG.

The peptides and agents described herein can be attached to the nanoparticle using any method, including those described herein and elsewhere (e.g., U.S. Publication No. 2001/0055581). Typically, a colloidal metal is incubated with the peptide and/or agent at a temperature from about 15 to about 50° C., e.g., about 20 to about 40° C., or about 24 to about 28° C. In some cases, an incubation can be done at about room temperature. An incubation period can range from about 5 minutes to about 24 hours, or any time therebetween, e.g., about 1 hour, 2 hours, 3 hours, 4 hours, 5 hours, 6 hours, 8 hours, 10 hours, 12 hours, 14 hours, 16 hours, 18 hours, 20 hours, 24 hours, or even longer. Additional considerations, such as pH, salt concentration, etc. can vary depending on the peptide and/or agent to be incorporated and the nature of the colloidal metal.

The concentration of peptides and/or agents can be adjusted so as to cover the entire surface or only a portion of the surface of the nanoparticle. If two or more peptides and/or agents are linked, they can be reacted (e.g., incubated), either sequentially or simultaneously, with the surface of the nanoparticle. In some cases, each peptide and/or agent is reacted at a concentration of about 50% or less than the saturation concentration of the agent for the nanoparticle. For purposes of this disclosure, the saturation concentration can be approximated as the concentration of peptide and/or agent at which a maximum of UV-Vis absorbance is obtained. In some cases, the concentration of the peptides and/or agents can be tailored according to the desired surface coverage. The resulting composition includes a nanoparticle having a surface that is linked to one or more peptides and/or agents. The population of the surface with such groups can be random or in a designed fashion.

In certain instances, the bioconjugates provided herein further comprise a diagnostic imaging agent attached to the surface of the metal nanoparticle. An imaging agent can allow the imaging of a bioconjugate in vivo. The imaging agent can be attached directly or via a linker to the surface of the metal nanoparticle. For example, a patient administered a bioconjugate having an imaging agent thereto can be imaged once, e.g., to locate and/or stage a tumor, or at multiple time points, e.g., to monitor the efficacy of the therapeutic agent.

Any type of imaging agent can be linked to a bioconjugate, including, for example, an MR imaging agent, a radio-imaging agent, an X-ray imaging agent, and a near-IR imaging agent. Two or more imaging agents can also be linked to a bioconjugate, such as an MR imaging agent and an X-ray imaging agent, or a near-IR imaging agent and an MR imaging agent. An MR imaging agent can be a metal chelate, e.g., can include a chelating ligand and a paramagnetic metal ion coordinated thereto. Any type of chelating ligand can be used, including cyclic and acyclic chelating ligands such as DTPA, DOTA, DOTMA, DTPA-BMA, DOTAGA, and HP-DO3A. Examples of paramagnetic metal ions include, without limitation, Gd(III), Fe(III), Mn(II), Cr(III), Cu(II), Dy(III), Ho(III), Br(In), Eu(III), Tb(II), Tb(III), and Tb(IV).

The bioconjugates described herein can further comprise a masking group linked to the surface of the metal nanoparticle. A masking group is a moiety that is used to inhibit the uptake of the nanoparticles by clearance mechanisms such as the reticuloendothelial system (RES). Typically, masking groups include PEG, PEG-derivatives (e.g., methyl ester or ether derivatives), and gangliosides.

PEG and derivatized PEG groups have been used to inhibit the uptake of the nanoparticles by clearance mechanisms such as the RES. A PEG derivative can include ether and ester derivatives, such as methyl or ethyl ether or methyl or ethyl ester derivatives. A PEG or PEG derivative can include thiol derivatives for linking the PEG or PEG derivative to the nanoparticle. While not being bound by any theory, it is believed that the small size of the nanoparticles described herein can allow the nanoparticles to exhibit a reduced or minimized clearance by the RES.

In certain instances, the bioconjugates described herein further comprise a targeting agent attached to the surface of the metal nanoparticle. The targeting agent can be attached directly or via a linker to the surface of the metal nanoparticle. A targeting agent having an affinity for, e.g., a cell receptor, a protein, or a polysaccharide, can allow the bioconjugate to accumulate at sites in the organism or cell where the target is present at higher concentrations compared to other tissues. In general, a targeting molecule can be one member of a binding pair that exhibits affinity and specificity for a second member of a binding pair. For example, an antibody or antibody fragment therapeutic agent can target a bioconjugate to a particular region or molecule of the body (e.g., the region or molecule for which the antibody is specific) while also performing a therapeutic function. Exemplary antibodies include an anti-VEGF antibody and an anti-EGFR antibody. Other therapeutic agents such as small molecules can similarly target a bioconjugate to a receptor, protein, or other binding site having affinity for the therapeutic agent.

In certain instances, the bioconjugates described herein further comprise a second therapeutic agent attached to the surface of the metal nanoparticle. The therapeutic agent can be attached directly or via a linker to the surface of the metal nanoparticle. Exemplary therapeutics include, but are not limited to, gemcitabine, rapamycin, capecitabine, 5-fluorouracil, floxuridine, doxifluridine, ratitrexed, methotrexate, trimetrexate, thapsigargin, taxol, paclitaxel, docetaxel, actinomycin D, dactinomycin, mercaptopurine, thioguanine, lovastatin, cytosine arabinoside, fludarabine, hydroxyurea, cytarabine, cytarabine, teniposide, topotecan, 9-aminocamptothecin, camptoirinotecan, crisnatol, busulfan, mytomycin C, treosulfan, staurosporine, 1-methyl-4-phenylpyridinium, mercaptopurine, thioguanine, cyclophosphamide, ifosfamide, EB 1089, CB 1093, KH 1060, carmustine, lomustine, mycophenolic acid, tiazofurin, ribavirin, EICAR, cisplatin, carboplatin, oxaliplatin, bevacizumab, mitomycin, dacarbazine, procarbizine, etoposides, prednisolone, trofosfamide, chlorambucil, melphalan, estramustine, dexamethasone, cytarbine, campathecins, bleomycin, doxorubicin, idarubicin, daunorubicin, doxorubicin, epirubicin, pirarubicin, zorubicin, verapamil, mitoxantrone, temozolomide, dactinomycin, plicamycin, bleomycin A2, bleomycin B2, peplomycin, asparaginase, vinblastine, vincristine, vindesine, vinorelbine, imatinib, thalidomide, leucovirin, deferoxamine, lenalidomide, bortezomib, erlotinib, gefitinib, sorafenib, erbitux, and sutinib.

Any of the compositions provided herein can be formulated to form a pharmaceutically acceptable composition adapted for human or animal patients. Pharmaceutically acceptable means that the composition can be administered to a patient or animal without unacceptable adverse effects. Pharmaceutically acceptable compositions include any pharmaceutically acceptable salt, ester, or other derivative that, upon administration, is capable of providing (directly or indirectly) a composition as described herein. Other derivatives are those that increase the bioavailability of the compositions when administered or which enhance delivery to a particular biological compartment.

Where necessary, the pharmaceutically acceptable compositions can include such ingredients as solubilizing agents, excipients, carriers, adjuvants, vehicles, preservatives, a local anesthetic, salts, flavorings, colorings, and the like. The ingredients may be supplied separately, e.g., in a kit, or mixed together in a unit dosage form. A kit can further include directions for administering the bioconjugate compositions and/or accessory items such as needles or syringes, etc.

The peptides and bioconjugates thereof described herein are useful in the treatment and diagnosis of disease states that are mediated by GIPC/synectin, such as cancer.

Thus, in one instance, provided is a method of treating or ameliorating one or more symptoms of cancer in a patient, the method comprising administering to a patient, in need thereof, a therapeutically effective amount of a peptide or a bioconjugate described herein to the patient.

Any cancer can be treated using the compositions and methods provided herein. Exemplary cancers include, but is not limited to pancreatic cancer, gastric cancer, lung cancer, and breast cancer. In certain instances, the cancer is any cancer that over expresses and/or is dependant on GIPC/synectin for growth and/or survival.

Also provided is a method of treating cancer in a patient, the method comprising co-administering to a patient, in need thereof, a therapeutically effective amount of a peptide or a bioconjugate as described and a therapeutically effective amount of a chemotherapeutic agent.

Examples of chemotherapeutics agents useful in the methods described herein include, but are not limited to, gemcitabine, rapamycin, capecitabine, 5-fluorouracil, floxuridine, doxifluridine, ratitrexed, methotrexate, trimetrexate, thapsigargin, taxol, paclitaxel, docetaxel, actinomycin D, dactinomycin, mercaptopurine, thioguanine, lovastatin, cytosine arabinoside, fludarabine, hydroxyurea, cytarabine, cytarabine, teniposide, topotecan, 9-aminocamptothecin, camptoirinotecan, crisnatol, busulfan, mytomycin C, treosulfan, staurosporine, 1-methyl-4-phenylpyridinium, mercaptopurine, thioguanine, cyclophosphamide, ifosfamide, EB 1089, CB 1093, KH 1060, carmustine, lomustine, mycophenolic acid, tiazofurin, ribavirin, EICAR, cisplatin, carboplatin, oxaliplatin, bevacizumab, mitomycin, dacarbazine, procarbizine, etoposides, prednisolone, trofosfamide, chlorambucil, melphalan, estramustine, dexamethasone, cytarbine, campathecins, bleomycin, doxorubicin, idarubicin, daunorubicin, doxorubicin, epirubicin, pirarubicin, zorubicin, verapamil, mitoxantrone, temozolomide, dactinomycin, plicamycin, bleomycin A2, bleomycin B2, peplomycin, asparaginase, vinblastine, vincristine, vindesine, vinorelbine, imatinib, thalidomide, leucovirin, deferoxamine, lenalidomide, bortezomib, erlotinib, gefitinib, sorafenib, erbitux, and sutinib.

A number of embodiments of the invention have been described. Nevertheless, it will be understood that various modifications may be made without departing from the spirit and scope of the disclosure.

EXAMPLES

Example 1

Preparation of Gold Nanoparticles

In a typical experiment, 50 ml of an aqueous solution containing 4.3 mg of solid sodium borohydride is added to 100 ml of 100 μM aqueous solution of tetracholoroauric acid under vigorous stirring. After overnight stirring, the gold nanoparticles thus formed are filtered through a 0.22 μm filter.

Example 2

In Vivo Knockdown of GIPC/Synectin Experiments

Ductal adenocarcinoma is the most common malignancy of the pancreas and a predominant cause of gastrointestinal cancer-related mortality. Despite even the most aggressive therapies, the five year survival rate for patients diagnosed with pancreatic cancer is less than 4%. This clearly indicates that novel approaches to the management of patients with pancreatic cancer are urgently needed and efficiently targeting the IGF-1 receptor could be one such avenue. IGF-1R activates several growth-promoting and apoptosis-inhibiting pathways including ras/raf/mitogen activated protein kinase (MAPK) 5, phosphatidylinositol-3 kinase (PI3K)/Akt, and janus/signal transducers and activators of transcription (STAT). It has been demonstrated that knockdown of the GAIP interacting protein (GIPC) reduced IGF-1R levels substantially in different pancreatic cancer cell lines and inhibited proliferation. GIPC (GAIP Interacting Protein, C-terminus) was originally identified as a binding partner of the RGS (Regulator of G Protein Signaling) protein GAIP (RGS 19), a GAP (GTPase activating protein) for heterotrimeric G proteins. The highly homologous protein synectin, which binds to the FGF-receptor syndecan-4, has been shown to be involved in cell migration and VEGF as well as FGF signaling. Responsible for the interaction of GIPC with IGF-1R is the PDZ domain 1, a protein domain family that is becoming increasingly recognized as a key mediator of numerous protein-protein interactions.

Knockdown of GIPC/synectin and subsequent reduction in IGF-1R expression and tumor growth in vivo is demonstrated herein. Based on these results, a small peptide ligand that inhibits the association between GIPC and IGF-1R by blocking the PDZ domain was developed. This led to decreased tumor growth in vitro and in vivo by reducing the protein levels of IGF-1R.

Results

Lentiviral GIPC/synectin shRNA transduction inhibits tumor cell growth in vivo. To evaluate the effect of GIPC/synectin in the in vivo tumor growth of pancreatic cancer, 1×10$^6$ MIA-PaCa2 tumor cells were transplanted subcutaneously into mice. The viability of these cells were carefully checked prior to transplant. GIPC/synectin was knocked down in these MIA-PaCa2 cells by transduction with lentiviral shRNA. To verify the effectiveness of the lentiviral transduction, a GFP-tagged lentivirus was used which exhibited a nearly 100% transduction efficiency. Furthermore, GIPC/synectin and IGF-1R levels were evaluated by immunoblot, demonstrating a clear reduction of GIPC/synectin and subsequent IGF-1R protein levels. A significant suppression in primary tumor growth after GIPC/synectin knockdown was found. By day 55, only 2 out of 5 mice were tumor-bearing in the GIPC/synectin knockout group, while all 5 mice had tumors in the control group. The average tumor size was 1317 mm$^3$ in the control group and 486 mm$^3$ in the GIPC/synectin knockout group. Tumor tissue lysate was tested for GIPC/synectin and IGF-1R expression by immunoblot. The IGF-1R level in the GIPC/synectin knockout group was significantly lower than that in the control group.

Orthotopic carcinoma development was simulated by injecting MIA-PaCa2 tumor cells with and without GIPC/synectin expression directly into the pancreas of 26 nude mice. In order to monitor tumor growth by bioluminiscence, the carcinoma cells were transfected with a GFPtagged luciferase (Luc) vector. Control cells were transduced with an empty GFP vector. Tumor development was monitored at different time points after application of n-luciferin. Throughout the entire time course and by day 39 post-tumor cell injection, suppressed primary tumor growth in mice with knocked down GIPC/synectin expression was found. By day 39, only 4 out of 13 animals were tumor-bearing in the GIPC knockout group compared to 10 out of 13 animals in the control group. No metastasis was found in either group.

PSQSSSEA (SEQ ID NO: 3) peptide blocks the PDZ domain of GIPC/synectin and prevents GIPC/synectin from binding to IGF-1R. It has been previously shown that GIPC/synectin and IGF-1R are associated with each other and that this association is important for the stability of IGF-1R. It has already been demonstrated that demonstrated that GIPC/synectin knockdown led to the degradation of IGF-1R and that the PDZ domain of GIPC/synectin is responsible for this interaction. To illustrate the use of GIPC/synectin as a therapeutic target, a peptide that binds to the PDZ domain and blocks the association between GIPC/synectin and IGF-1R was developed.

To initiate the development of this GIPC-targeting compound, peptide sequences derived from different proteins known to bind the PDZ domain of GIPC/synectin were analyzed. A GAIP, a regulator of G-protein signaling (RGS) was finally selected. A short stretch of the C-terminal sequence has been identified as the specific functional binding site for the PDZ domain of GIPC/Synectin.

The peptides were prepared utilizing standard Fmoc-based solid-phase peptide synthesis techniques, with at least eight residues of the GAIP sequence. Analysis of this peptide sequence in a phage ELISA showed significantly enhanced binding to the PDZ domain of GIPC/synectin over that of other PDZ domain motifs and a negative control. The GAIP octapeptide was tagged with FITC to visualize its localization by confocal microscopy and myristoylated to ensure that the peptide entered the cells, as demonstrated in.

To test whether there was decreased binding between IGF-1R and GIPC/Synectin, MIA-PaCa2 cells were transfected with a FLAG-tagged wild type GIPC/synectin plasmid and blotted against IGF-1R after immunoprecipitation for FLAG. After treatment with the peptide and blockage of the proteasomal degradation of IGF-1R to ensure similar IGF-1R protein levels, the association between IGF-1R and GIPC/synectin was significantly reduced. These results indicated that the small peptide was effective in inhibiting the association between IGF-1R and GIPC/Synectin. PSQSSSEA (SEQ ID NO: 3) peptide inhibits expression of IGF-1R and influences proliferation pathways in vitro and in vivo.

To determine whether the GAIP peptide influences IGF-1R protein levels, IGF-1R expression was examined by Western blot. The experiments clearly showed a downregulation of IGF-1R. Accordingly, proliferation was inhibited at a dose of 200 μM as tested with a MTS assay. To evaluate the in vivo efficiency of the peptide, 1×10$^7$ MIA-PaCa2 cells were subcutaneously injected into mice. These mice received daily injections into the developing tumor of either 10 mM of the peptide (treatment group) or DMSO (control group). After 25 days of injections, the mice were sacrificed and compared tumor growth between peptide-treated mice and the control group that received DMSO alone. On day 22, the peptide-treated mice had, on average, a smaller tumor than the control group. The average tumor size in the control group was 620 mm$^3$ (95% confidence interval: 515-724 mm$^3$) while the treatment group had an average tumor size of 268 mm$^3$ (95% confidence interval: 53-484 mm$^3$). On day 25, the average tumor size in the control group was 851 mm$^3$ (95% confidence interval: 619-1084 mm$^3$) and 480 mm$^3$ (95% confidence interval: 230-729 mm$^3$) in the treatment group.

Example 3

Human pancreatic cancer cells are known to over express a number of important growth factors and their receptor tyrosine kinases. These include epidermal growth factor (EGF) and its receptor (EGFR), different fibroblast growth factors (FGFs) and their receptors (FGFR), insulin like growth factor-1 (IGF-1) and its receptor (IGF-1R), and VPF/VEGF. Over expression of growth factors and their receptors lead to tumor cell proliferation, an effect further enhanced by mutations of the k-ras oncogene. Recently, it was demonstrated that over expression and activation of IGF-1R is mostly mediated by auto-regulation and mTOR plays a significant role in this activation. Therefore, it was postulated that because IGF-1R is a key regulatory molecule of pancreatic cancer growth and metastasis, utilizing rapamycin should have a significant effect on PCA. Earlier results suggest, VPF/VEGF plays a key role in tumor angiogenesis and an anti-VPF/VEGF therapy in combination with a rapamycin blockade against IGF-1R should be an effective therapy against pancreatic cancer growth and metastasis. Furthermore, results indicated that anti-VEGF antibody in combination with rapamycin showed a significant effect on primary tumor growth and metastasis of pancreatic adenocarcinoma in a xenograft mouse model.

RGS-GAIP-interacting protein C terminus (GIPC) is involved in protein trafficking, endocytosis, and receptor clustering and has been shown to be associated with IGF-1R, a receptor important for proliferation and anchorage-independent growth. Examination of the role of GIPC in the regulation of IGF-1R protein levels in expression by RNA interference showed reduced IGF-1R protein levels and a subsequent decrease in proliferation of PCA cells. It was also determined that the PDZ domain of GIPC is essential for the post-translational regulation of IGF-1R. The importance of GIPC in pancreatic cancer development and progression is supported by tissue microarray data of 300 pancreatic cancer specimens where GIPC is highly expressed in PCA. Kaplan-Meier survival analysis showed the tendency of a shorter overall survival in patients with adenocarcinomas expressing a high level of GIPC (p=0.19 univariate analysis; median survival with low expression 19 months median survival with high expression 16 months). Taken together, data suggested that GIPC is a central molecule for the stability of IGF-1R.

In addition, with its PDZ domain, GIPC is associated with a vast list of transmembrane receptors, including integrin α6 and α 5 that are expressed in several pancreatic cancer cell lines. To investigate the possible function of GIPC in EGFR expression in pancreatic cancer, it was found that knocking down GIPC with RNA interference led to a down regulation of EGFR. EGFR is a receptor tyrosine kinase highly expressed in pancreatic cancer cells and is a prognostic factor for overall survival. Because GIPC associates with integrin α 5 and α 6 through its PDZ domain, the possible role of this interaction in the down regulation of EGFR in AsPC1 pancreatic adenocarcinoma cells was studied. A peptide designed to disrupt the interaction between the PDZ domain and the cytoplasmic tail of integrin α 5 and α 6 (KERLTSDA, SEQ ID NO. 8) was utilized. The disruption of the protein-protein interaction led to a down regulation of EGFR in concordance with the RNA interference data. This data suggested that integrins may have some regulatory function on EGFR expression via GIPC.

Attachment of GIPC Peptide with gold nanoparticles increased the anti-proliferation efficacy against the cancer cells. The GAIP peptide (SEQ ID NO.3) can efficiently block AsPC1 pancreatic cancer cell proliferation in the range of 100-200 μm in vitro. However, when the peptide was attached to gold nanoparticles the efficiency of the peptide increased at least 25 to 50 fold.

Example 4

Various studies have demonstrated the importance of GAIP interacting protein, C terminus (GIPC, also known as Synectin) as a central adaptor molecule in different signaling pathways and as an important mediator of receptor stability. Accordingly, GIPC/synectin is associated with different growth promoting receptors like IGF-1R and integrins. These functions were mediated through its PDZ domain. Furthermore, GIPC/synectin has been shown to be overexpressed in pancreatic and breast cancer. The goal of this study was to demonstrate the importance of GIPC/synectin in pancreatic cancer growth and to evaluate a possible therapeutic strategy by using a GIPC-PDZ domain inhibitor. In vivo effects of GIPC/synectin knockout were studied after lentiviral transduction of luciferase-expressing pancreatic cancer cells with shRNA against GIPC/Synectin. Knockdown of GIPC/synectin led to a significant inhibition of pancreatic adenocarcinoma growth in an orthotopic mouse model. To prove that GIPC/synectin can serve as a therapeutic target for pancreatic cancer therapy, a GIPC-PDZ-targeting peptide was designed. This cell-permeable PDZ inhibitor was able to block tumor growth significantly without showing toxicity in a mouse model. These findings demonstrate that targeting GIPC/synectin and its PDZ domain is an effective strategy for therapeutic intervention of pancreatic cancer. Furthermore, the effect of targeting the PDZ domain of GIPC on the stability of one of its associated growth factor receptors, IGF-1R, was studied. Targeting the PDZ domain of GIPC/synectin with an octapeptide was able to block the interaction of IGF-1R and GIPC which led to reduced IGF-1R levels in the pancreatic cancer cells.

Example 5

Ductal adenocarcinoma is the most common malignancy of the pancreas. Despite even the most aggressive therapies, the five year survival rate for patients diagnosed with pancreatic cancer is less than 4%. This clearly indicates that novel approaches to the management of patients with pancreatic cancer are urgently needed. The establishment of new targets in pancreatic cancer treatment is an important step toward longer survival and better prognosis. One of these new targets could be GAIP interacting protein, C-terminus (GIPC), a protein shown to be overexpressed in pancreatic and breast cancer.

GIPC is highly expressed in pancreatic cancer. GIPC/synectin was originally identified as a binding partner of the RGS (Regulator of G Protein Signaling) protein GAIP (RGS 19), a GAP (GTPase activating protein) for heterotrimeric G proteins. Recently, different studies suggest an important role of GIPC/synectin in the biology of normal and malignant cells. Interestingly, it was also demonstrated that GIPC/synectin is important for IGF-1R stability in pancreatic cancer cell lines.

In this study, it is demonstrated that knockdown of GIPC/synectin reduces tumor growth after orthotopic transplantation of different pancreatic cancer cell lines in nude mice. In conjunction with these efforts, a small peptide was developed that blocks the PDZ domain of GIPC. This led to decreased tumor growth of different pancreatic cancer cell lines in vitro. In vivo this GIPC-PDZ targeting peptide suppressed pancreatic cancer growth in a mouse model. Furthermore, the influence of targeting GIPC/synectin on one of its associated growth factor receptors, IGF-1R, was tested. As expected, the octapeptide led to decreased association between IGF-1R and GIPC/synectin in different pancreatic cancer cell lines. This, in turn, reduced IGF-1R protein levels in the cells. In essence, this study represents a first step towards developing a novel therapeutic for pancreatic adenocarcinoma treatment using a PDZ-inhibitor.

Materials and Methods

Cell culture, cell infection and immunofluorescence. MIA-PaCa2, PANC1 and AsPC1 were purchased from the American Type Culture Collection (Manassas, Va.). To generate the lentivectors, 293T cells were co-transfected with gag-pol expression plasmid pCMV 8.91, VSV.G envelope expression plasmid pMD-G, and vector plasmid pLKO.1 encoding cDNAs for expression of GIPC/synectin shRNA (5'-CCGGGCAAATGCAATAATGCCCTCACTCGAGTGAG-GGCATTATTGCATTTGCTTTTTG-3' (SEQ ID NO: 14)) and firefly luciferase (Fluc). GIPC/synectin shRNA in pLKO.1 was purchased from Open Biosystems. Supernatant was collected 48 hours later and frozen at −80° C. MIA PaCa2 or AsPC1 cells were then infected with a multiplicity of infection of eight overnight at 37° C., and they were injected after overnight infection. To ensure efficiency of GIPC/synectin knockout cells, protein lysates were analysed by immunoblot for GIPC/synectin and IGF-1R. Control cells were transduced with an empty GFP vector. RNAi in cell culture was performed as described. The localization of FITC labeled octapeptides was analyzed by fluorescence microscopy using a microscope (Zeiss Axiovert 100M, Carl Zeiss Inc., Germany). After excitation by 488 nm light, the 520 nm emission was measured using special filters. In vivo GIPC/synectin knock out experiments and non-invasive imaging of tumor burden. All procedures involving animals were approved by and conducted according to guidelines of the Institutional Animal Care and Use Committee of the Mayo Foundation. $10 \times 10^6$ control and GIPC/synectin negative MIAPaCa2 (n=10 treatment, n=10 control), resuspended in 50 μL of sterile PBS, were injected directly into the pancreas. To monitor tumor burden, mice were imaged using the IVIS 200 Bioluminescence Imaging System (Xenogen Corp., Alameda, Calif.). For imaging, 150 mg/kg D-luciferin (Xenogen) was applied intraperitoneally ten minutes before scanning. Thirty-nine days after injection, the mice were euthanized. The final tumor volume was measured and calculated using the formula ½a×b2, where a is the longest tumor axis, and b is the shortest tumor axis. Procedures were adapted accordingly for the treatment of GIPC expressing (n=10) and GIPC shRNA expressing AsPC1 (n=10) pancreatic cancer cells. Not all tumors in this group were monitored by bioluminescence. This experiment was stopped 14 days post implantation. For another group of mice, GIPC/synectin negative (n=5) and control MIAPaCa2 cells (n=5) were implanted s.c. into the right flank of nude mice for detection of IGF-1R using immunoblot. After 55 days the mice were euthanized, and tumor tissue was evaluated for IGF-1R and GIPC/synectin expression by immunoblot analysis. Selected tumors were evaluated with histology, HE staining, Ki67 staining.

Peptide Design

GIPC (GAIP interacting protein, C terminus) is a PDZ domaincontaining protein that interacts specifically with the C-terminus of RGS-GAIP, a GTPase-activating protein (GAP) for $G_{\alpha i}$ subunits located on clathrin-coated vesicles. The last eight residues (PSQSSSEA (SEQ ID NO: 3)) of the C-terminal sequence of GAIP were selected for preparation of linear peptide ligands. In order to enhance cell permeability, myristolation was performed on the N-terminus, where it would not interfere with the critical C terminal binding epitope. An analog in which FITC was incorporated was prepared for visualization experiments. A third peptide ligand with a corresponding sequence, prepared with N-terminal biotinylation, was used to conduct pull-down assays to prove the in vitro binding of this peptide to GIPC/synectin via its single PDZ domain. As a control peptide, an octapeptide with the following sequence was used: Myr-ADSTLREK (SEQ ID NO: 15).

Preparation of T7 Phage Displaying GIPC-PDZ dsDNA encoding the PDZ domain of GIPC/synectin was double-digested with EcoRI and HindIII, and the DNA (0.8 μL of a 45 nM (7.7 ng/μL) solution) was used in the ligation reaction with the T7 Select 10-3 vector arms (Novagen, 0.5 μL), along with 10× ligase buffer (0.25 μL); ATP (10 mM, 0.25 μL, final concentration 1 mM); DTT (100 mM, 0.25 μL); and T4 DNA ligase (0.5 μL, 1 unit/μL). The sample was incubated at 16° C. for 16 h. The T7 phage packaging reaction was performed by adding packaging extract (Novagen, 12.5 μL, or half the manufacturer's recommended amount) to the ligation reaction sample (2.5 μL) and allowing it to incubate for 2 h at room temperature. The reaction was stopped by the addition of a sterile LB medium (135 μL). A plaque assay was performed to determine the number of recombinant phage generated. E. coli BTL5403 was grown at 37° C. with shaking in LB/Amp50 medium (10 mL) until OD~1.0 was reached. Top agarose (10 mL) was melted and equilibrated to this temperature. A series of dilutions was prepared prior to plating the phage. The first dilution was generated by adding packaged phage (10 μL) to LB/Amp50 (990 μL) for a total of 100-fold dilution ($10^2$). Subsequent dilutions were prepared by adding the previous dilution (100 μL) to fresh LB/Amp50 (900 μL); generally, $10^3$-$10^5$ dilutions were plated. In this case, the $10^3$ and $10^4$ dilutions were plated by adding 400 μL of E. coli stock with the phage dilution sample (100 μL) and melted top agarose (3 mL) to a pre-warmed LB or LB/Amp50 agar plate. The plates were inverted upon hardening and allowed to incubate at 37° C. for 3-4 h (or at room temperature if incubated overnight). Plaques generated were counted to determine the titer and the number of recombinants generated. Eight plaques from the 104 dilution sample were selected and used to infect fresh E. coli stock (1 mL) as above. The samples were incubated at 37° C. with shaking until lysis was observed. A phage lysis sample (1.5 μL) for each was subjected to PCR amplification (using the Novagen primers), purified (Qiagen PCR Removal Kit), and the DNA submitted for sequencing; the presence of the inserted sequence for the GIPC/Synectin-PDZ domain was confirmed for all samples.

ELISA Protocol

Neutravidin plates (Pierce) were coated in duplicate with 100 µL of 10 µg/mL solutions of N-terminal biotinylated peptides (PSQSSSEA (SEQ ID NO: 3) (from GAIP), KKETEV (SEQ ID NO: 12) and KKETAV (SEQ ID NO: 13) (two sequences that bind PDZ3 of PSD-95 (21), and allowed to incubate 1-2 h at 37° C. (or overnight at 4° C.) with mild shaking. The unbound peptides were washed away three times with TBS (0.5% Tween-20)-TBST buffer. Blocking buffer was prepared by diluting BSA (10 mg/mL) in TBS stock two-fold in dH2O (for a 5% BSA final concentration) and free biotin (1 mM). Alternatively, SuperBlock in PBS buffer (Pierce) with free biotin (1 mM) was used. The blocking buffer was added to each well and allowed to incubate 30-60 min at 37° C. with mild shaking. The blocking buffer was washed away with TBST by inverting the plate and tapping off the excess with each of the 4-5 washes. The GIPC/Synectin-PDZ T7 phage to be screened with the biotinylated peptides were prepared by adding phage stock (1 mL, 20 µL) derived from one of the eight plaques (discussed above) to freshly harvested BLT5403 $E.$ $coli$ at OD~1. Once lysis was observed, the cell debris was spun down and phage lysate was used in a plaque assay (as discussed above) to determine the titer (phage titer added to wells $5 \times 10^9$ pfu). GIPC/Synectin-PDZ phage (100 µL) were added to the wells and incubated for 1-2 h at 37° C. (or overnight at 4° C.) with mild shaking. The plates were then washed 3-4 times with TBST buffer to remove unbound phage. Primary monoclonal T7 tail antibody (Novagen) was added to each well at a 1:2000 dilution in blocking buffer without biotin, and allowed to incubate for 1 h at 37° C. with mild shaking. Unbound primary antibody was washed away 3-4 times with TBST buffer. Secondary antibody conjugated with alkaline phosphatase (Pierce; Ab host: rabbit anti-, antigen: mouse IgG (H+L)) was added to each well at a 1:5000 dilution in blocking buffer without biotin; this was incubated at 37° C. for 1 h with mild shaking. Unbound secondary antibody was washed 3-4 times with TBST buffer. Substrate for detection was prepared by adding diethanolamine 5× concentrate to HPLC grade H2O in a 1:4 ratio (5 mL total volume), followed by dissolving a single PNPP tablet (Pierce) with mild shaking. The substrate was added to each well, and the development was measured at 405 nm after 30 min, 1 h and 2 h.

In vivo PSQSSSEA Experiments

When the tumor reached about 5 mm-15 mm in diameter after subcutaneous transplantation of MIAPaCa2 cells (n=10 treatment, n=10 control) into the mouse right flank, mice were treated with 10 mM of peptide for 27 days dissolved in DMSO. The peptide was applied directly into the tumor. The control group was treated with phosphate buffered saline solution alone.

Western Blot, Plasmid Transfection, Immunoprecipitation and Proliferation/Viability Assays Whole cell lysates were prepared as previously described and separated by SDS-PAGE. Goat polyclonal antibodies against the N-terminus of GIPC (clone N19, Santa Cruz Biotechnology, Santa Cruz, Calif.), rabbit polyclonal antibodies against the beta-chain of IGF-1R (clone C20, Santa Cruz Biotechnology), antibodies against Akt (Cell Signaling, #9272) and pAkt-Ser 473 (Cell Signaling, #4051) and antibodies against β-actin and FLAG (Sigma, St. Louis, Mo.) were used for immunodetection, followed with an HRP-conjugated secondary antibody (Santa Cruz Biotechnology), and the SuperSignal West Pico substrate (Pierce Biotechnology, Rockford, Ill.). Immunoprecipitations were performed as previously described (22). Proteasome inhibitor I (Calbiochem, San Diego, Calif.) was used at a concentration of 25 µM. Plasmid transfection was performed using the Effectene Kit (Qiagen, Valencia, Calif.) according to the recommendation of the manufacturer. The procedures and plasmids have been described earlier. Human rIGF-1 has been purchased from RnD Biosystem, Minneapolis, Minn. Viability of the cells was measured using a colorimetric 3-(4-5-dimethylthiazol-2-yl)-5-(3-carboxymethoxyphenyl)-2-(-4-sulfophenyl)-2H-tetrazolium salt (MTS) assay (Promega, Wisconsin, Wis.). For proliferation a thymidine incorporation was used.

Histology and Immunohistochemistry

HE staining and immunostaining for Ki67 (n=6 treatment, n=7 control) was performed as described by the manufacturer. For evaluation the Zeiss Axioplan 2 microscope was used. Photos are made with Zeiss Axiocam. For photos 40× objectives were used. Statistical Analysis. Data are presented as means and differences in means with 95% confidence intervals for the differences. Tests for statistical differences were performed using t-tests and Mann-Whitney tests and Wilcoxon tests. For the in vivo experiments, at least 10 mice were used each group. This number was derived by power analysis to detect a 50% reduction in tumor size, with a beta error of 3%. Because the overall sample size was small and outcome variables could have a non-normal distribution, the non-parametric Mann-Whitney test was used to detect statistical significant differences in each group. P values less than 0.05 were considered to be significant. The significance of the tumor take rates was calculated by using a Wilcoxon-test. Asterixes* in the figures represent statistically significant results (probability p<0.05).

Results

Lentiviral GIPC/Synectin shRNA Transduction Inhibits Tumor Cell Growth in vivo.

Figure 1B:
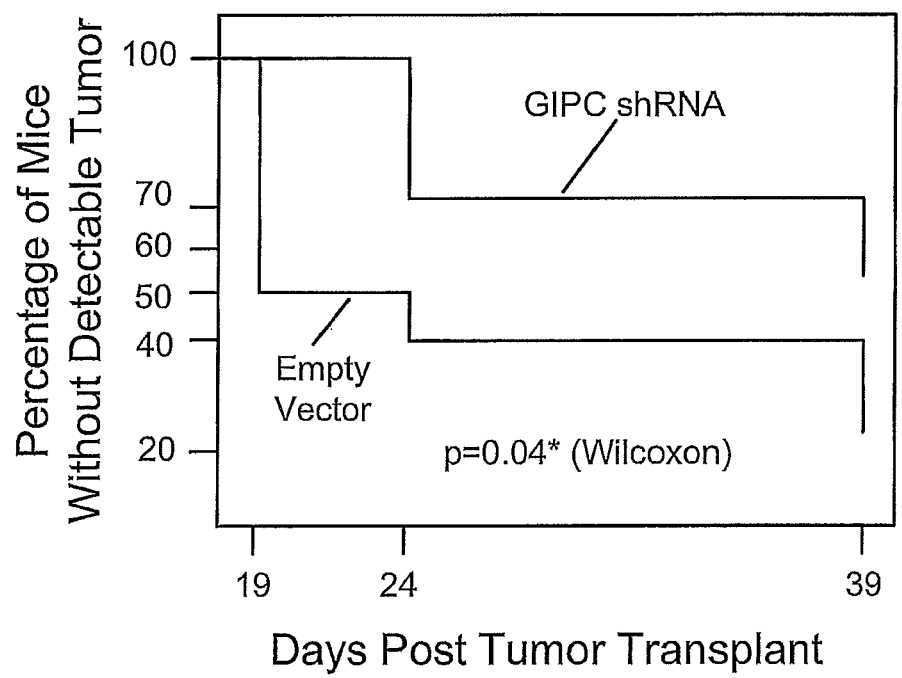
Figure 1C:
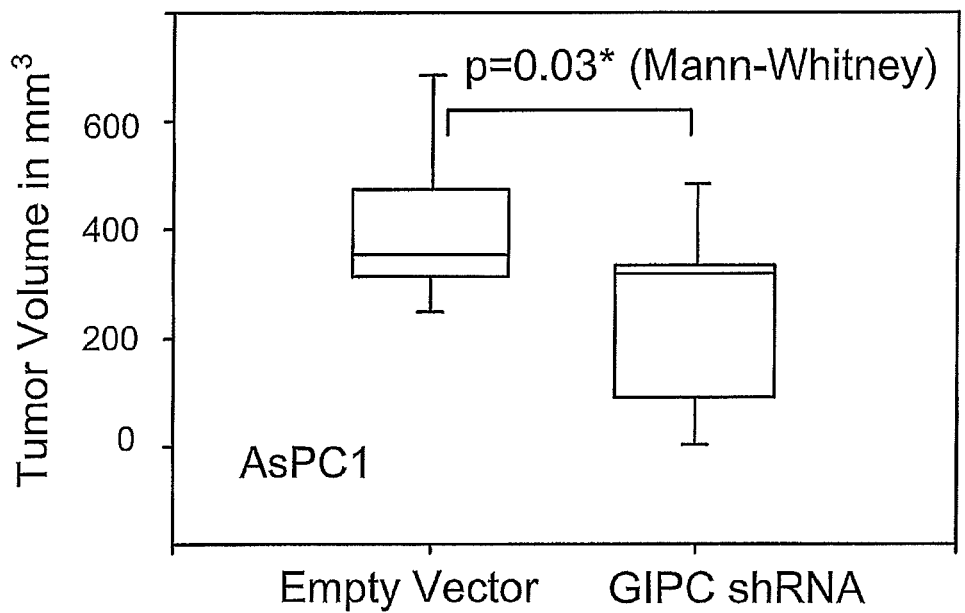

To evaluate the effect of GIPC/synectin in the in vivo tumor growth of pancreatic cancer, GIPC shRNA expressing MIA-PaCa2 tumor cells were injected orthotopically into the pancreas of 20 nude mice. The viability of these cells was carefully checked prior to transplant. GFP tagged vectors were used to ensure a high transduction efficiency (data not shown). GIPC/synectin were evaluated by immunoblot, demonstrating a clear reduction of GIPC/Synectin. In order to monitor tumor growth by bioluminiscence, all carcinoma cells were additionally transfected with a luciferase (Luc) vector. Tumor development was monitored at different time points after application of nluciferin (FIG. 1a). The experiment was stopped 39 days after tumor transplantation. Throughout the entire time course and by the end of the experiment, significantly suppressed primary tumor growth was observed (p=0.04; Wilcoxon test) in mice which received tumor cells expressing GIPC shRNA. At the end of the experiment, only 5 out of 10 animals were tumor-bearing in the GIPC knockout group, compared to 8 out of 10 animals in the control group (FIG. 1b). No metastasis was found in either group (FIG. 1a). To address the heterogeneity of pancreatic cancer $1 \times 10^6$ control and GIPC shRNA expressing AsPC1 pancreatic cancer cells orthotopically were injected into 20 nude mice. As expected, this experiment showed also a significantly reduced tumor growth (p=0.03; Mann-Whitney-test) in the GIPC knockdown group compared to the control group (FIG. 1 c).

A GIPC-PDZ Binding Octapeptide Reduces Cancer Cell Proliferation in vitro.

Figure 2A:
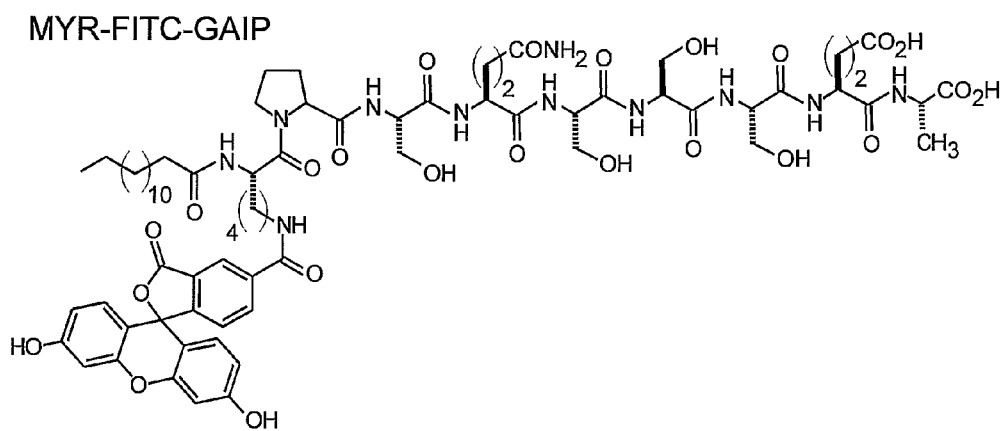
FIGS. 2(A) through 2(F) show a GIPC-PDZ binding octapeptide reducing cancer cell proliferation in vitro. The chemical structure of the N-terminal Lys-FITC modified version of the blocking peptide PSQSSSEA (SEQ ID NO: 3) is depicted in FIG. 2(A)). Results from a phage binding assay with N-terminal biotinylated versions of the blocking peptide PSQSSSEA (SEQ ID NO: 3), the PDZ3 domain-binding peptides KKETEV (SEQ ID NO: 12) and KKETAV (SEQ ID NO: 13), and a negative control are shown in FIG. 2(B)). The blocking peptide showed a strong affinity to the PDZ domain of GIPC/Synectin, the other PDZ domain peptides were not recognized.
Figure 2B:
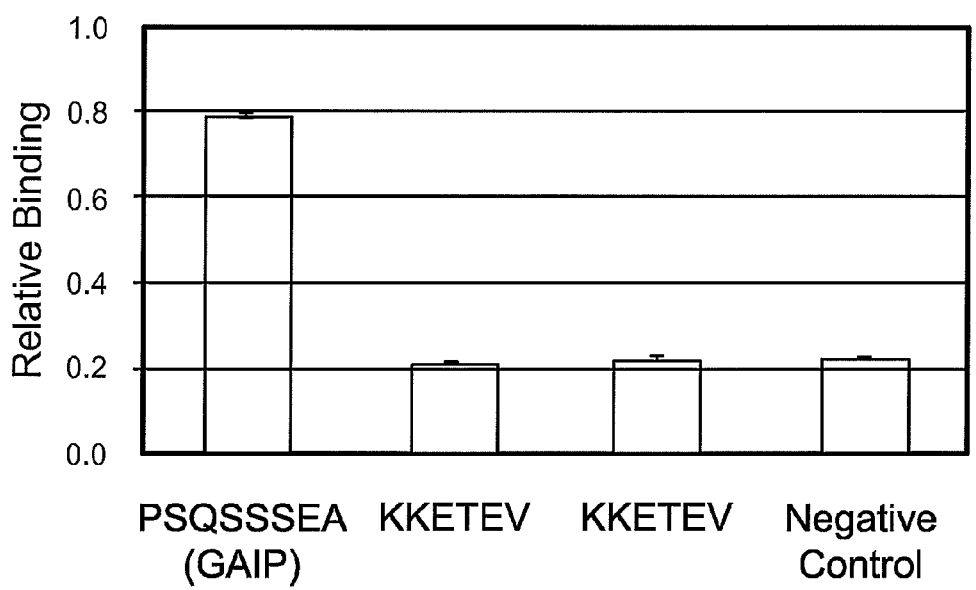
Figure 2C:
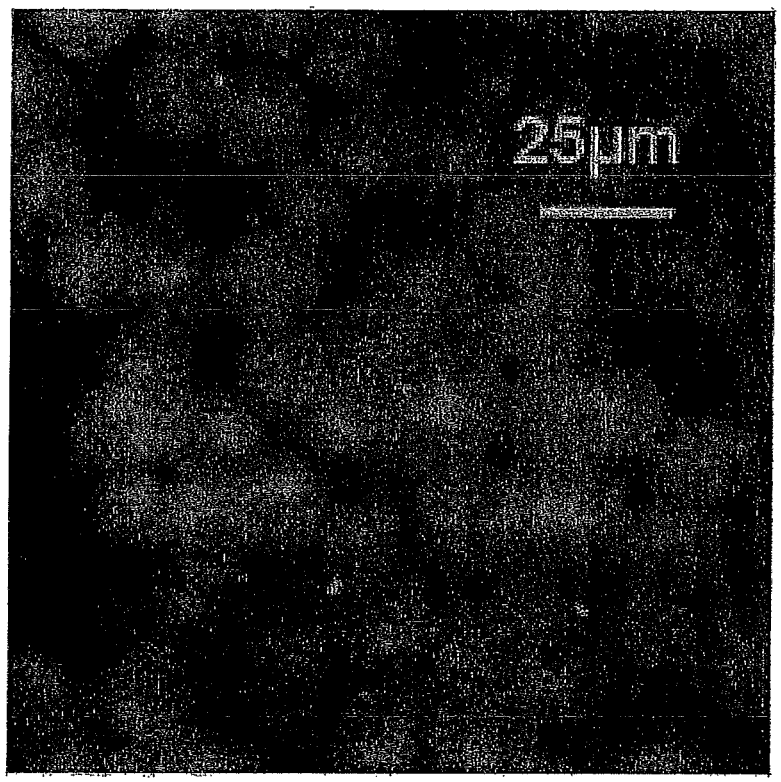
Figure 2D:
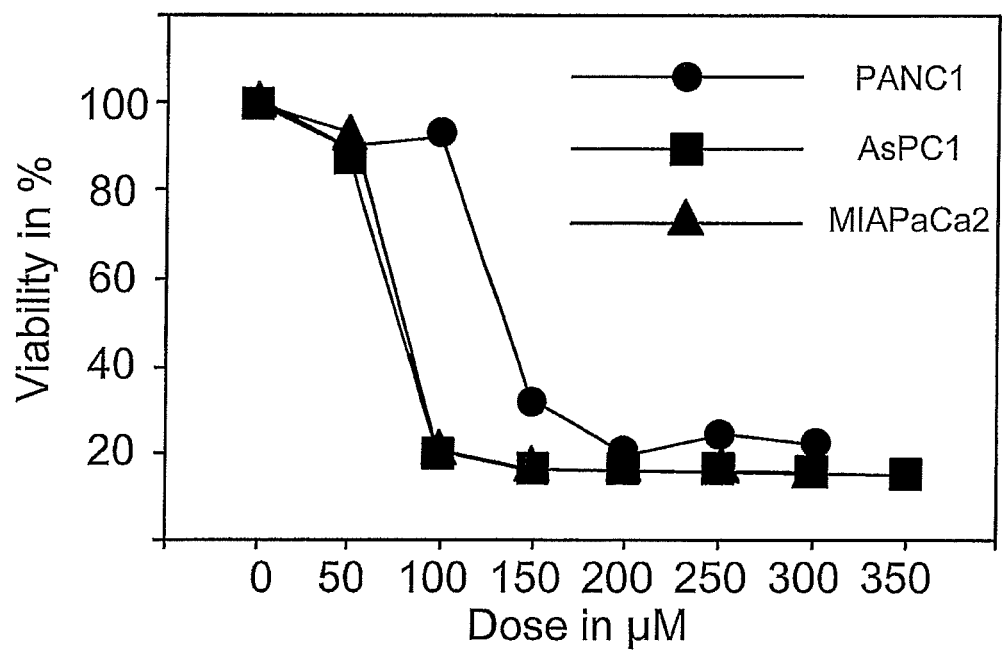
Figure 2E:
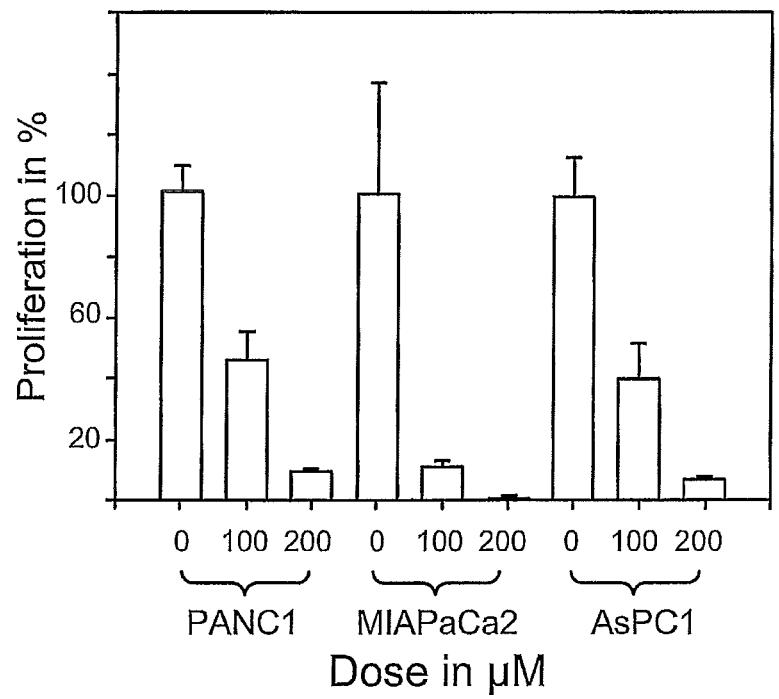
Figure 2F:
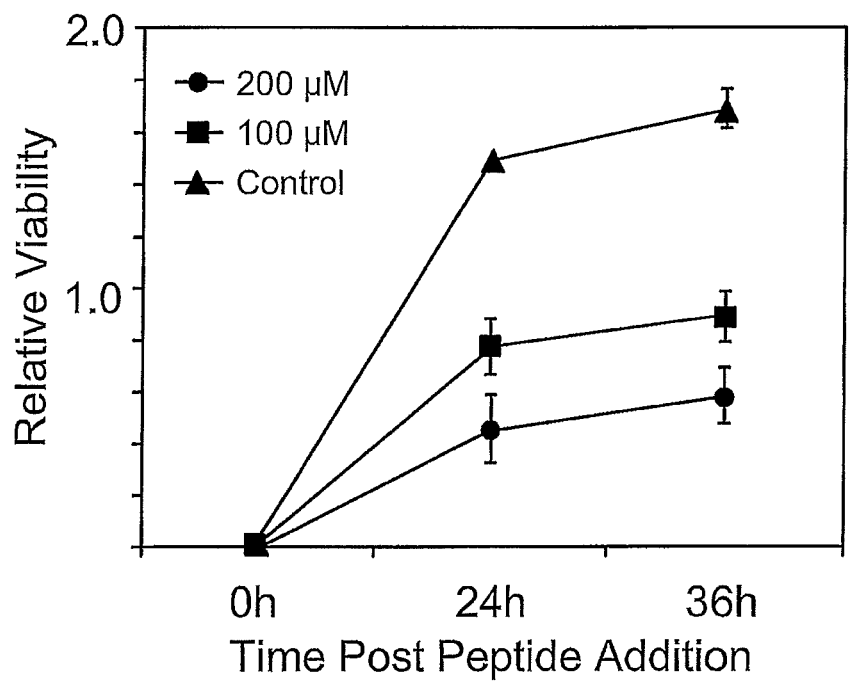

To illustrate the use of GIPC/synectin as a therapeutic target, a peptide that binds to the PDZ domain was developed. This domain is important for GIPCs function in receptor clustering and intracellular protein transportation. To initiate the development of this GIPC-targeting compound, peptide sequences derived from different proteins known to bind the PDZ domain of GIPC/synectin were evaluated. A peptide derived from GAIP, a regulator of G-protein signaling (RGS) was selected. A short stretch of the C terminal sequence has been identified as the specific functional binding site for the PDZ domain of GIPC/Synectin. Because the binding affinity for a given binding partner is often found within the first five or six residues of the domain—although additional residues may contribute—corresponding peptides were prepared, utilizing standard Fmoc-based solid-phase peptide synthesis techniques, with at least eight residues of the GAIP sequence (FIG. 2a). Analysis of this peptide sequence in a phage ELISA showed significantly enhanced binding to the PDZ domain of GIPC/synectin over that of PDZ domain motifs of different other proteins and a negative control (FIG. 2b). The GAIP octapeptide was tagged with FITC to visualize its localization by confocal microscopy and myristoylated to ensure that the peptide entered the cells, as demonstrated in FIG. 2c. In a next step, the influence of the designed peptide on the viability and proliferation of different human pancreatic carcinoma cells was tested. Viability was inhibited in a dose dependent fashion in a concentration range from 0-300 μM as tested with a MTS assay in different pancreatic carcinoma cell lines (FIG. 2d). A thymidine incorporation assay clearly demonstrated that this decrease in viability can be attributed to the reduction in proliferation (FIG. 2e). In FIG. 2f the time dependency of the peptide effect is shown.

Figure 3A:
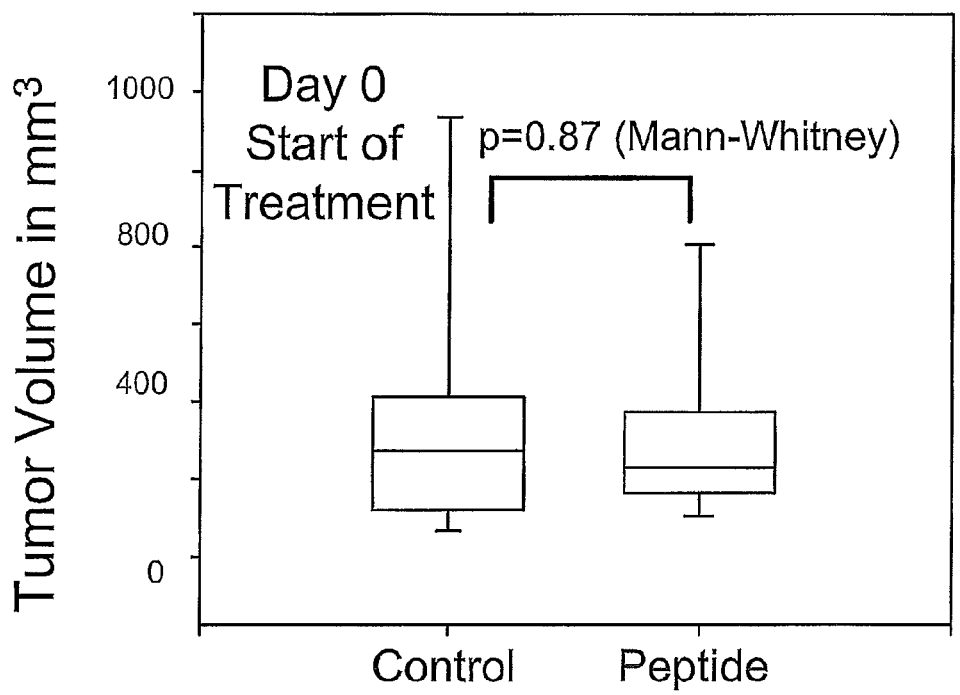
FIGS. 3(A) through 3(D) show GIPC blocking octapeptide leading to a significant reduction of tumor growth in mice. Growth characteristics of MIAPaCa2 pancreatic cancer cells after subcutaneous implantation and intratumoral treatment with the PSQSSSEA (SEQ ID NO: 3) are shown in FIGS. 3(A) and 3(B). The box plots show the tumor volume at day 0 (FIG. 3(A)) and day 27 (FIG. 3(B)) of treatment. 10 nude mice were treated, 10 nude mice serve as a control. The treatment was started when the tumor was established and reached the following volumes: 269 mm3 average tumor size in the control group (95% confidence interval: 112-584 mm3) and 231 mm3 average tumor size in the treatment group (95% confidence interval: 149-462 mm3). Treatment day 27: the peptide-treated mice had a significantly smaller tumor than the control group (p=0.01, Mann-Whitney test, average tumor size in the control group: 4036 mm3, 95% confidence interval: 2275-6239 mm3, average tumor size in the treatment group 661 mm3, 95% confidence interval: 228-2528 mm3).
Figure 3B:
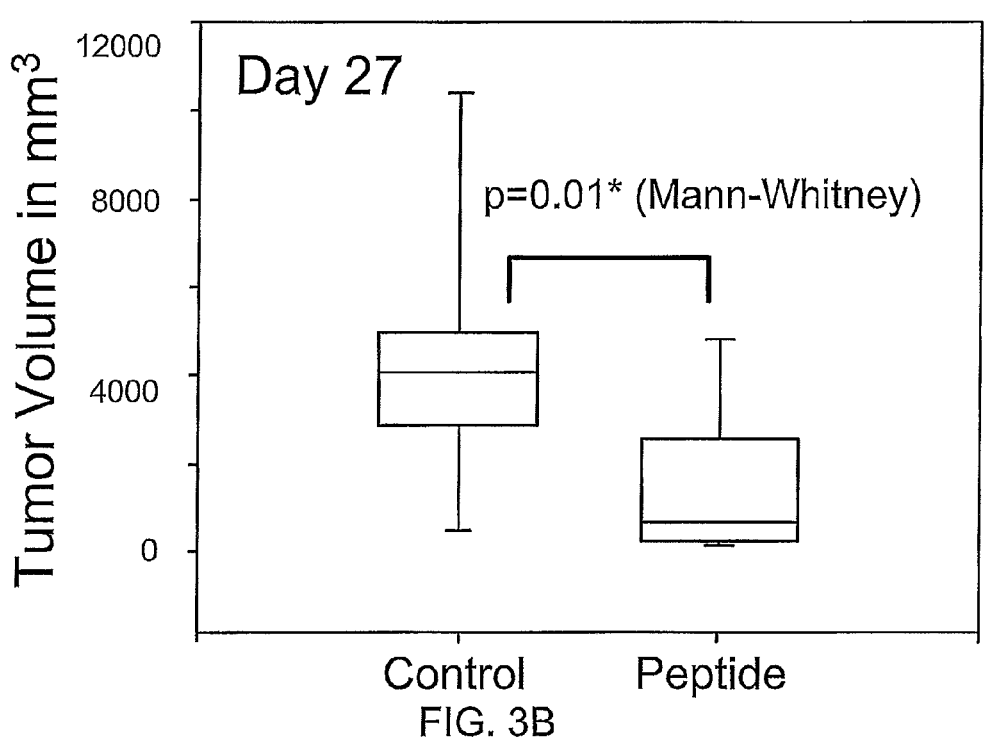
Figure 3C:
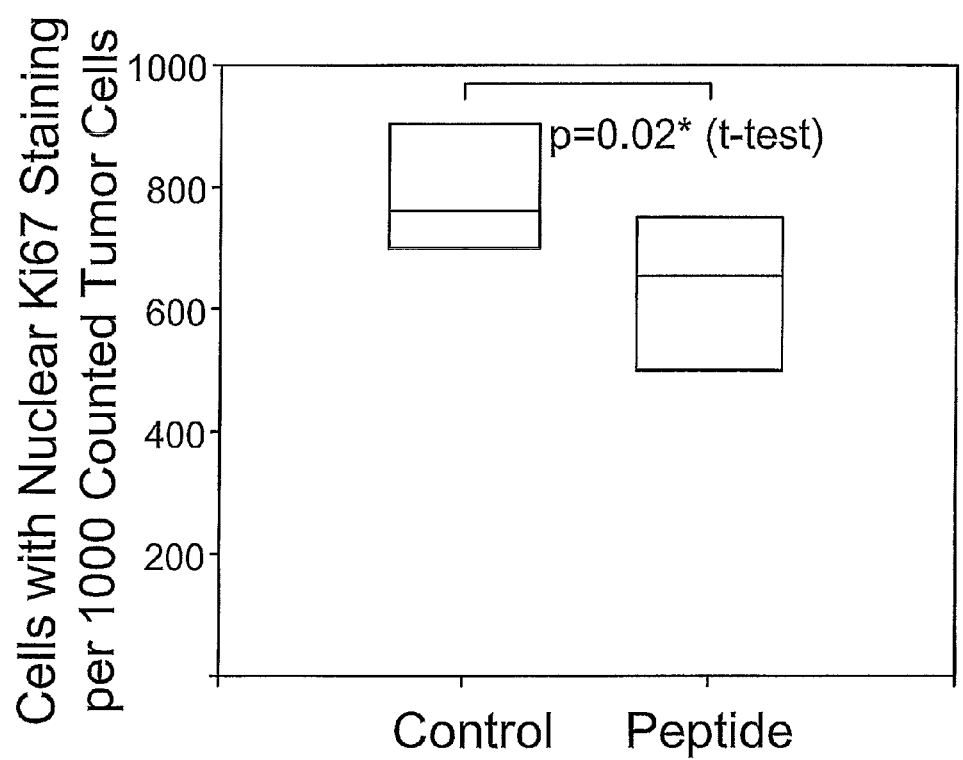
Figure 3D:
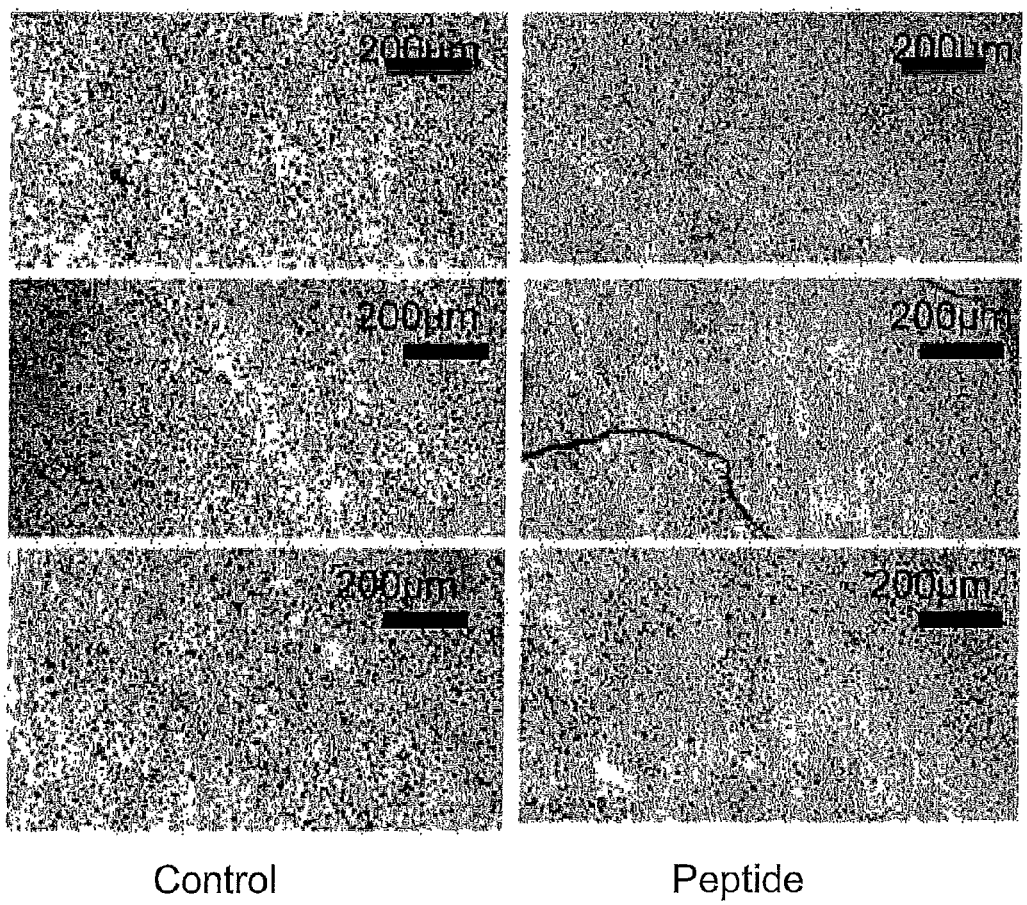

The GIPC Blocking Octapeptide Leads to a Significant Reduction of Tumor Growth in Mice To evaluate the in vivo efficiency of the peptide, $1 \times 10^7$ MIAPaCa2 cells were injected into 20 nude mice and injected a total of 10 mM of the peptide daily into the developing tumor. During the whole course of treatment the PDZ domain inhibitor did not show any toxicity in the rodents. After 27 days of treatment, the mice were sacraficed and compared tumor growth between peptide-treated mice (n=10) and the control group (n=10) that received buffered saline solution alone. The PDZ-inhibitor-treated mice had a significantly smaller tumor than the control group (p=0.01, Mann-Whitney test) (FIGS. 3a, 3b). The evaluation of the proliferation marker Ki67 demonstrates a significantly lower proliferation activity in the treatment group compared to the control group (p=0.013; t-test) (FIG. 3c and FIG. 3d).

Targeting the PDZ Domain of GIPC Alters IGF-1R Levels

Previously, it has been shown that GIPC/synectin is associated with IGF-1R. This interaction has been proven to be important for the IGF-1 receptor stability and to be mediated by the PDZ domain.

Figure 4C:
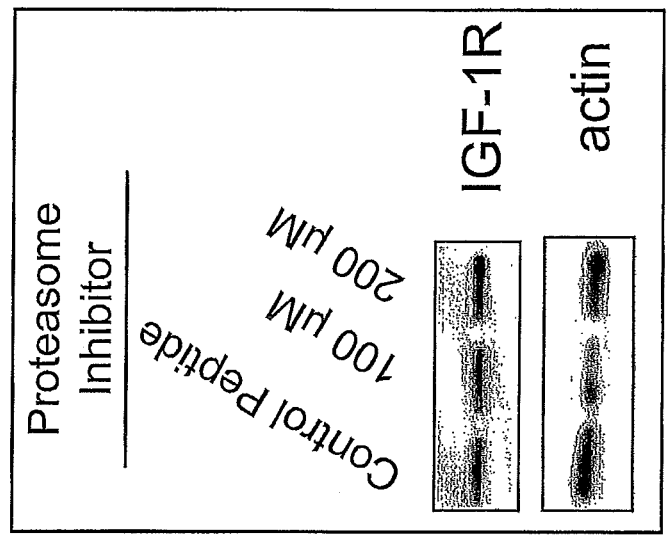
FIGS. 4(A) through 4(C) show targeting the PDZ domain of GIPC alters IGF-1R levels.
Figure 4B:
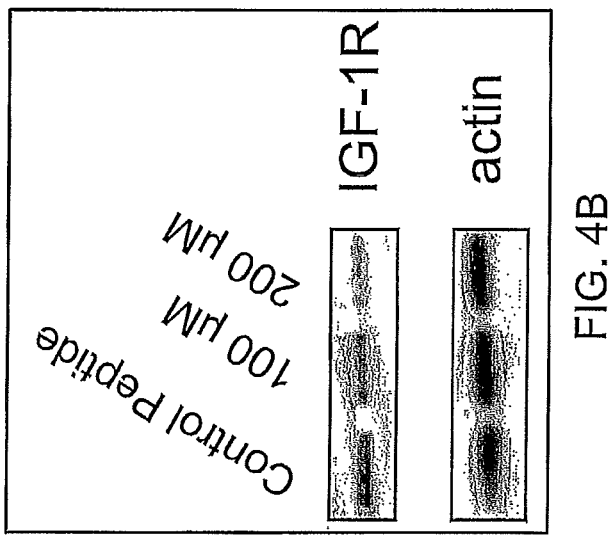
Figure 4A:
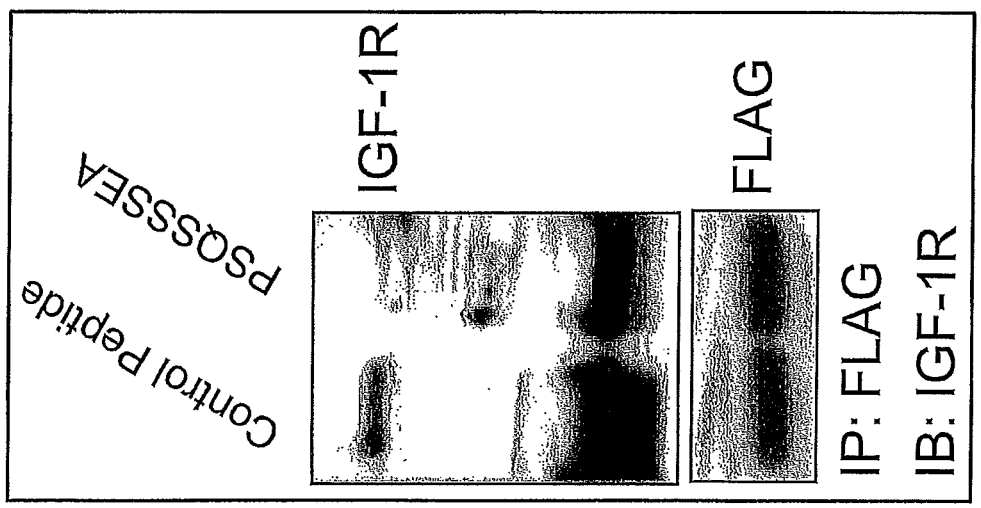
Figure 5A:
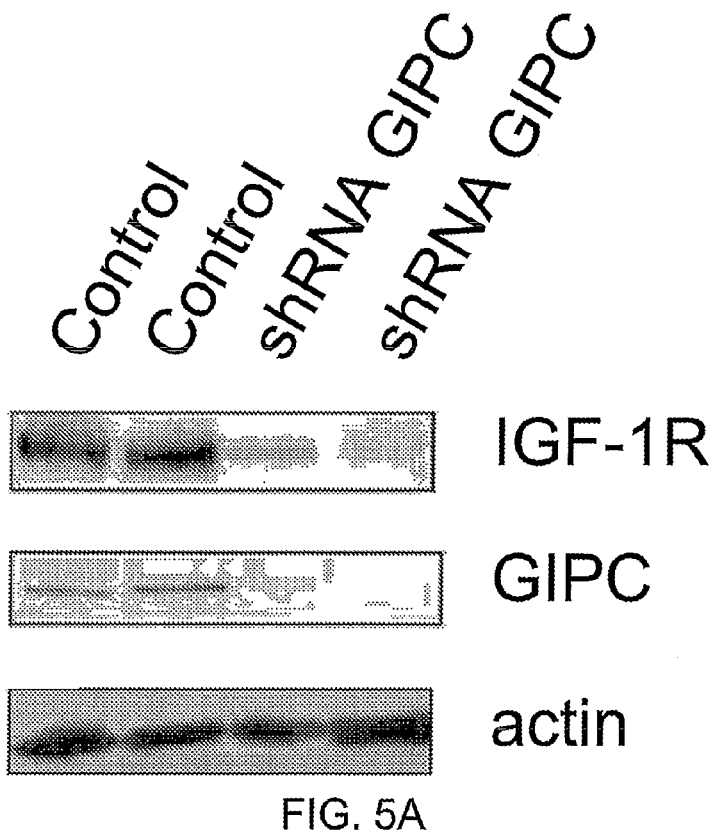
FIGS. 5(A) through 5(C) show additional experiments where targeting the PDZ domain of GIPC alters IGF-1R levels.
Figure 5B:
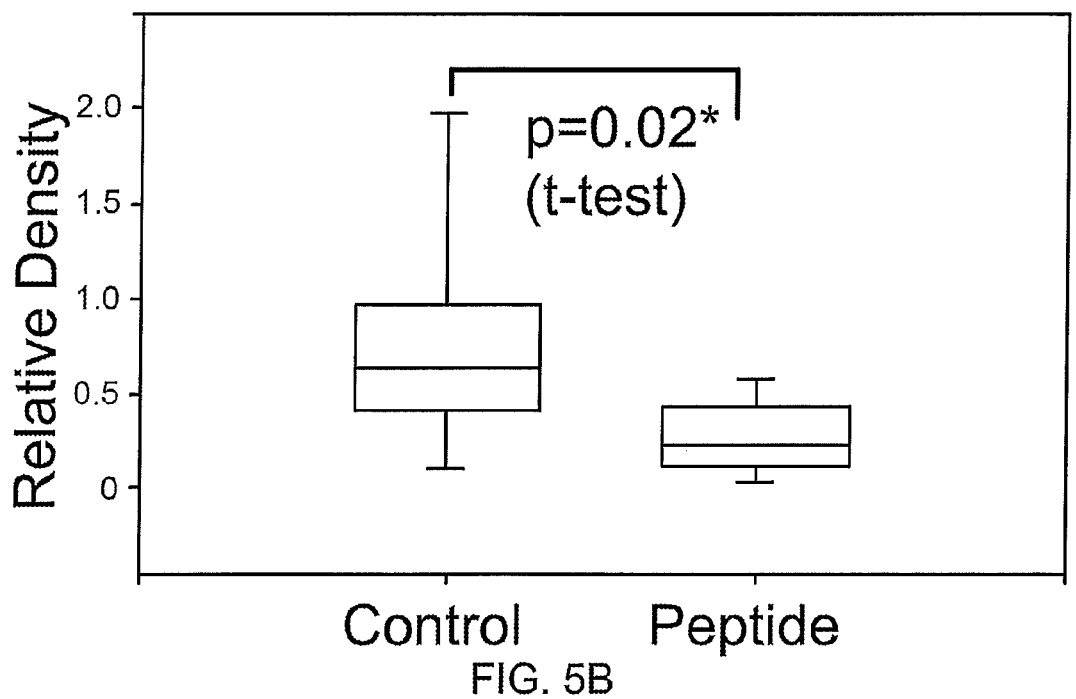
Figure 5C:
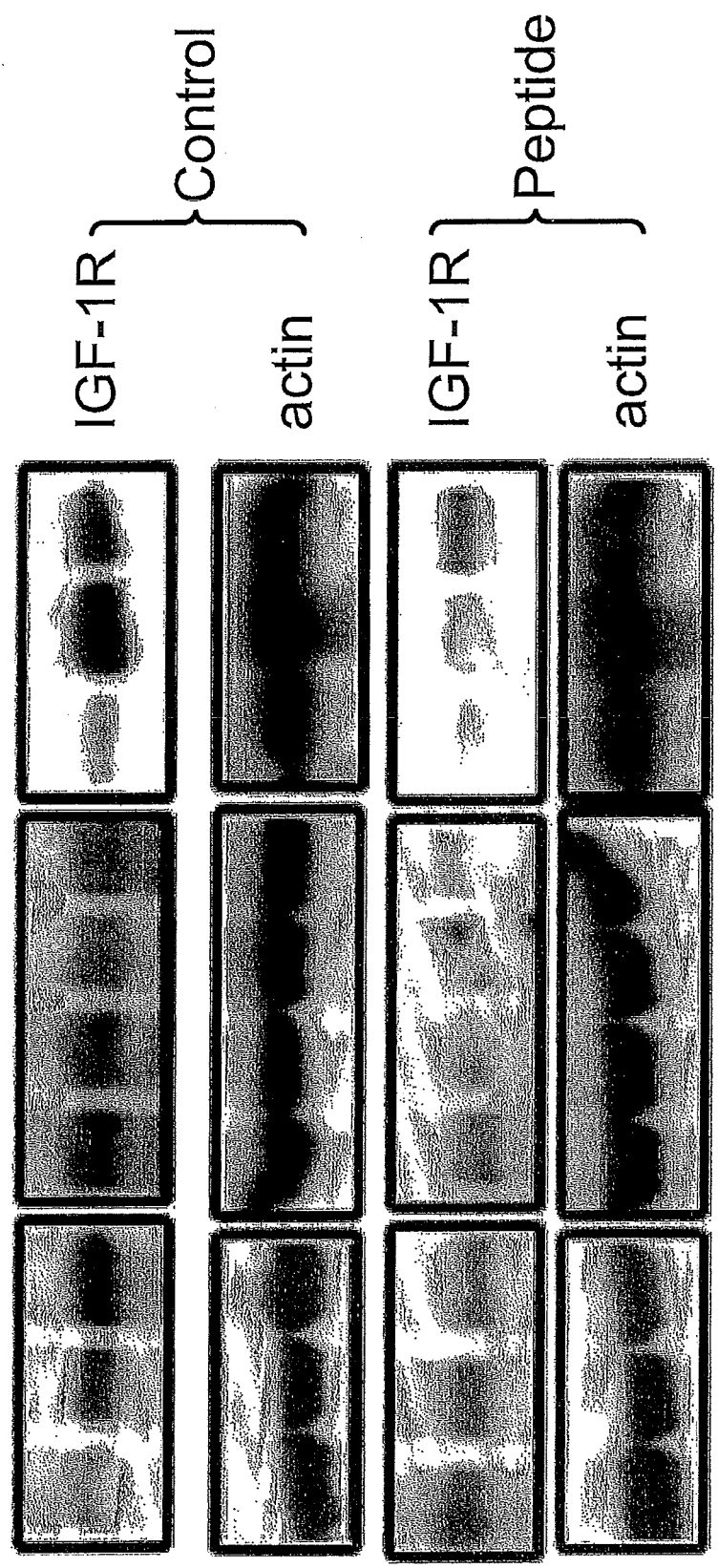
Figure 6:
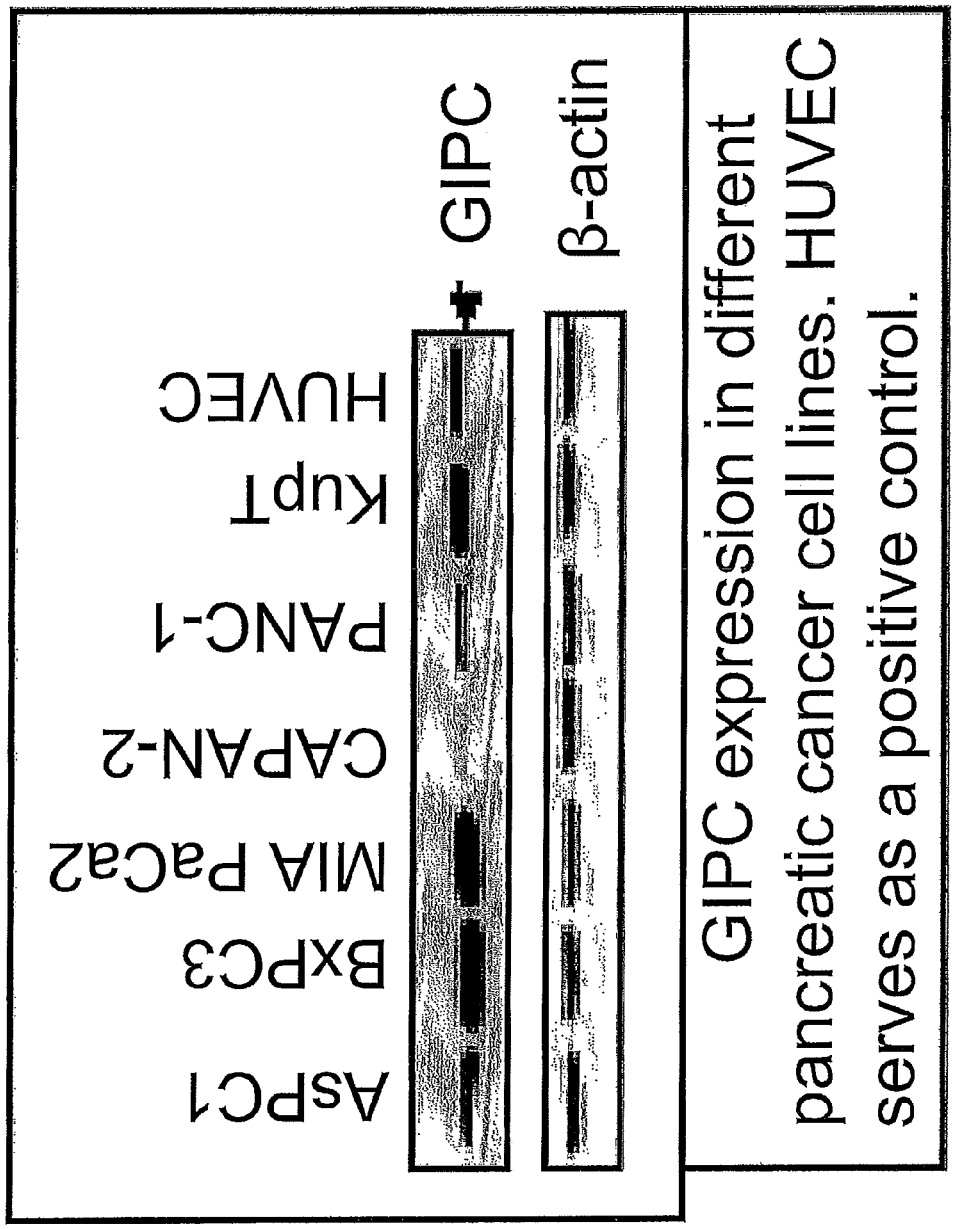
FIG. 6 shows integegrin α5 expression in PCA cancer cell lines.
Figure 7:
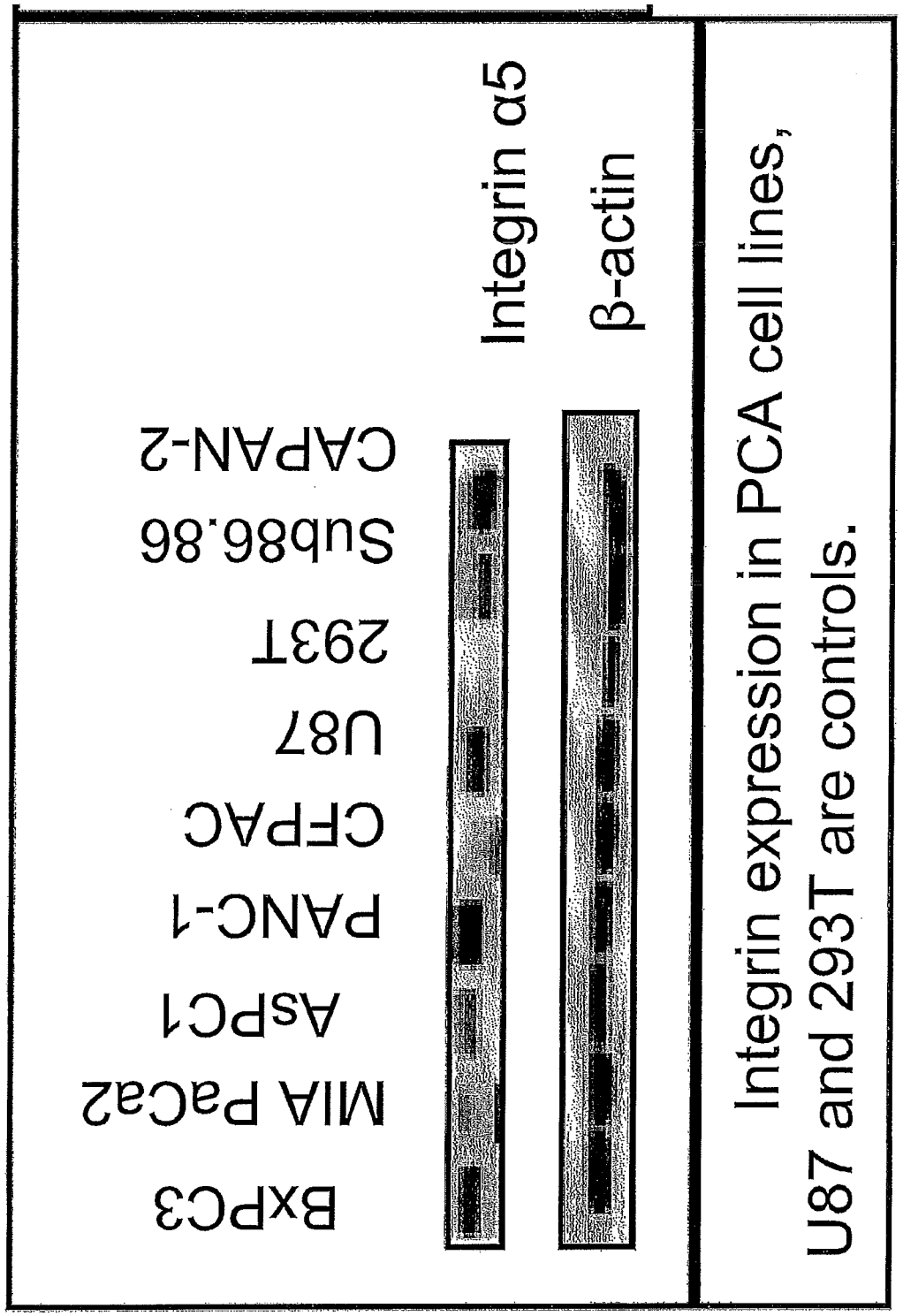
FIG. 7 shows GIPC expression in various pancreatic cancer cell lines.
Figure 8:
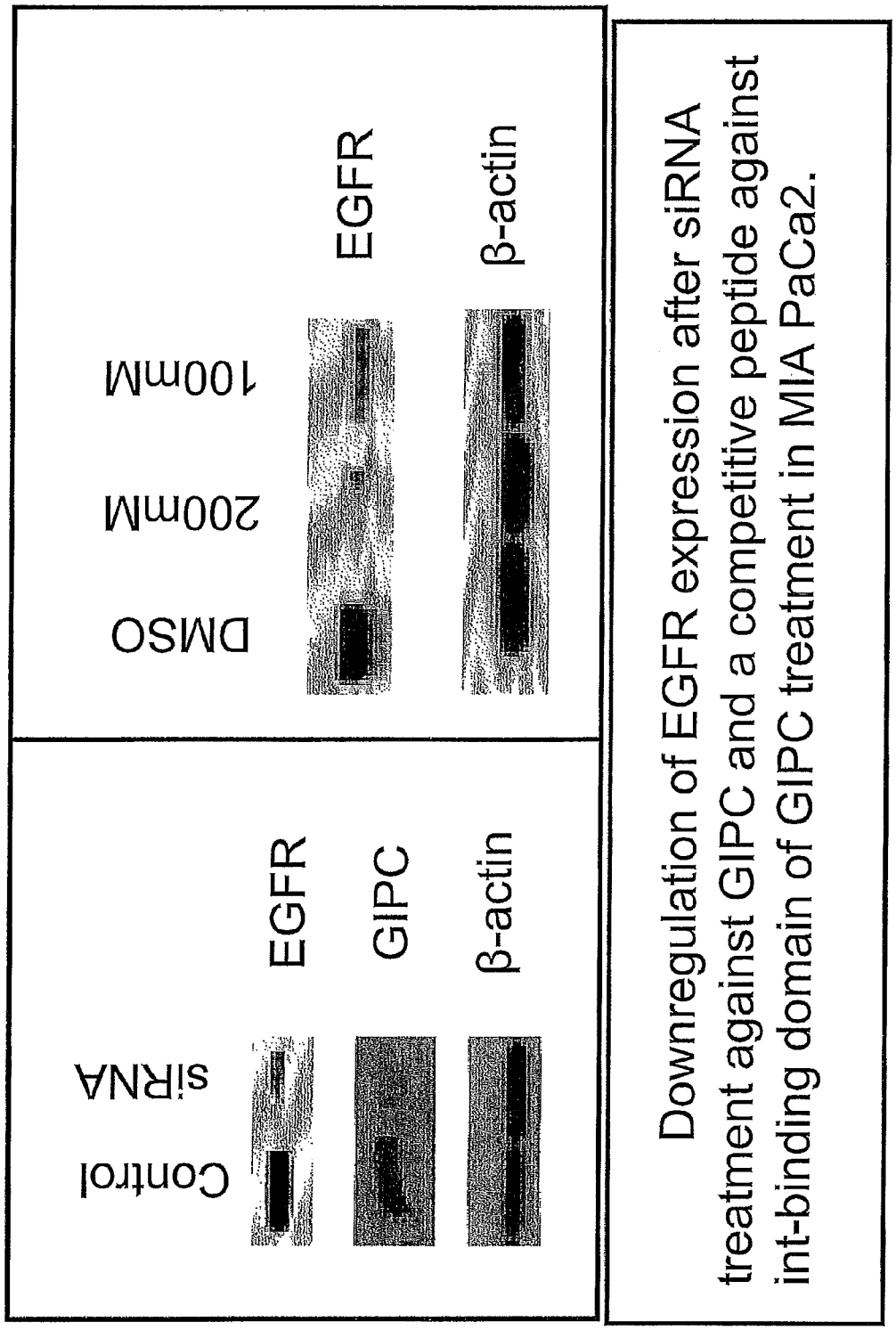
FIG. 8 shows the down regulation of EGFR after treatment with siRNA treatment against GIPC and a competitive peptide.
Figure 9:
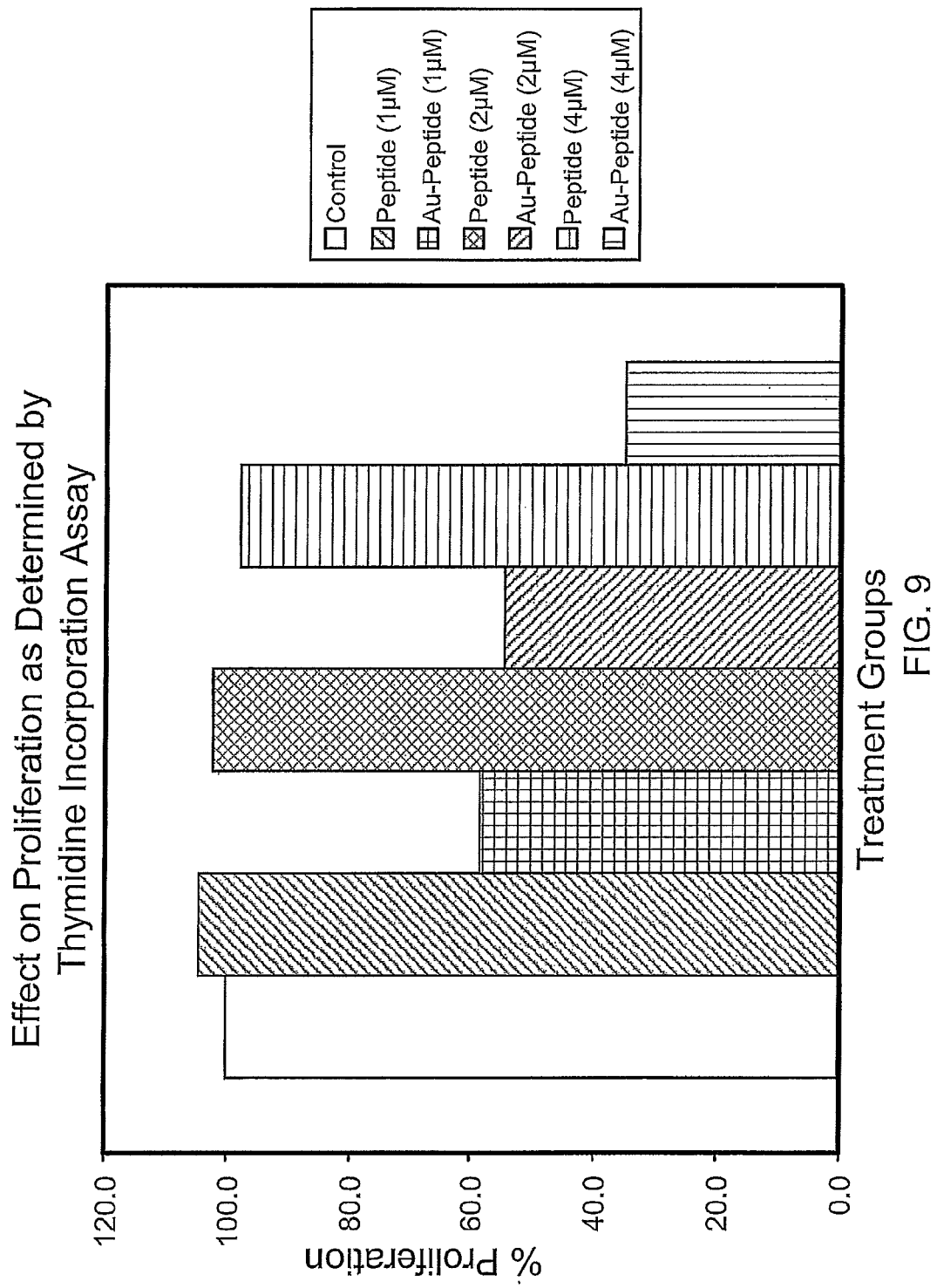
FIG. 9 shows the effect on proliferation of AsPC1 cancer cells after treatment with 1, 2, and 4 µM of an octapeptide (SEQ ID NO.8) and a gold nanoparticle bioconjugate.
Figure 10:
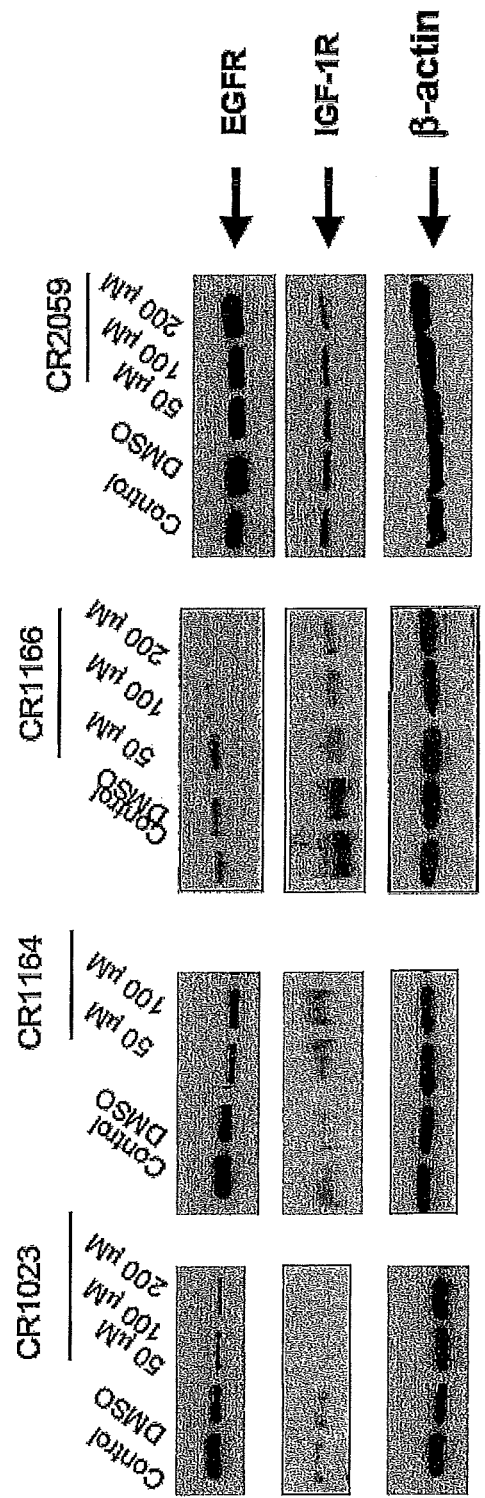
FIG. 10 illustrates the effect of EGFR and IFG-1R expressions in MD231A-WT cells treated with GIPC inhibitor peptides CR1023 (SEQ ID NO: 16), CR1164 (SEQ ID NO: 19), CR1166 (SEQ ID NO: 20), and CR2059 (SEQ ID NO: 24).
Figure 11:
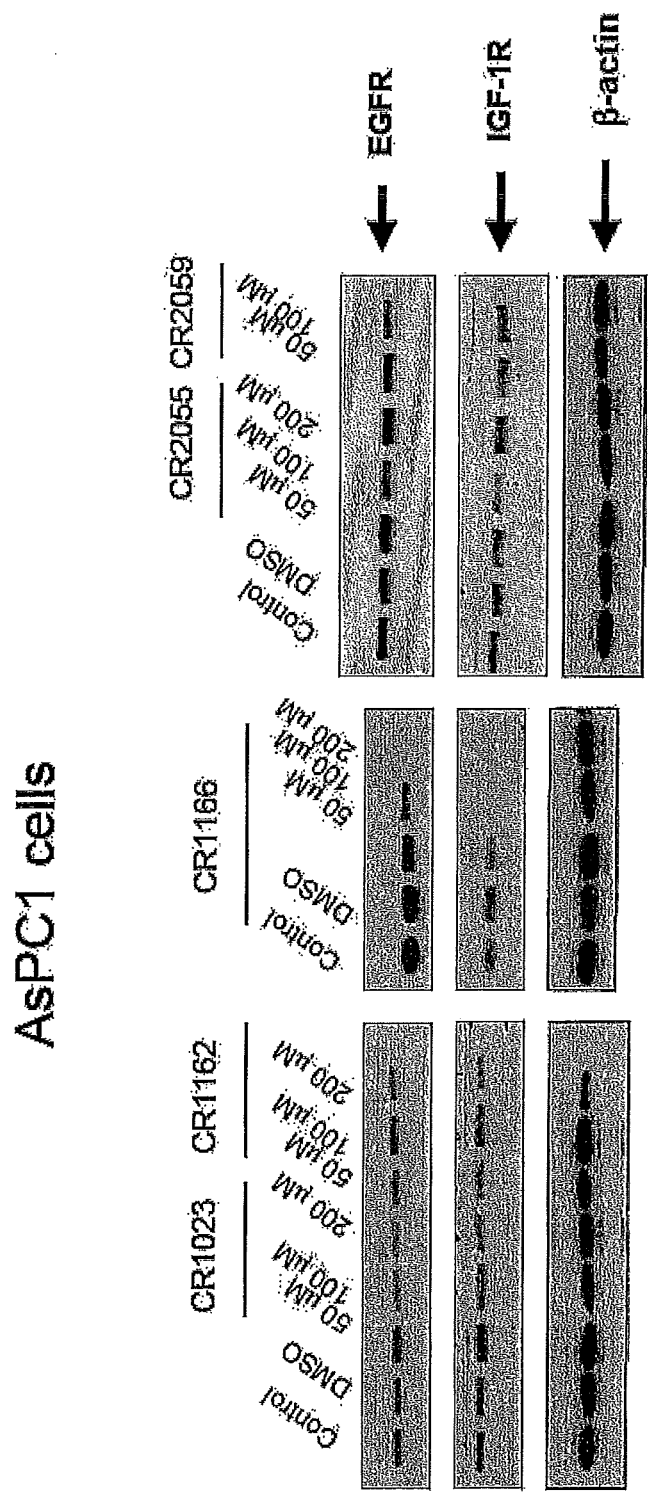
FIG. 11 shows the effect of EGFR and IFG-1R expressions in AsPC1 cells treated with GIPC inhibitor peptides CR1023 (SEQ ID NO: 16), CR1162 (SEQ ID NO: 18), CR1166 (SEQ ID NO: 20), CR2055 (SEQ ID NO: 23), and CR2059 (SEQ ID NO: 24).
Figure 12:
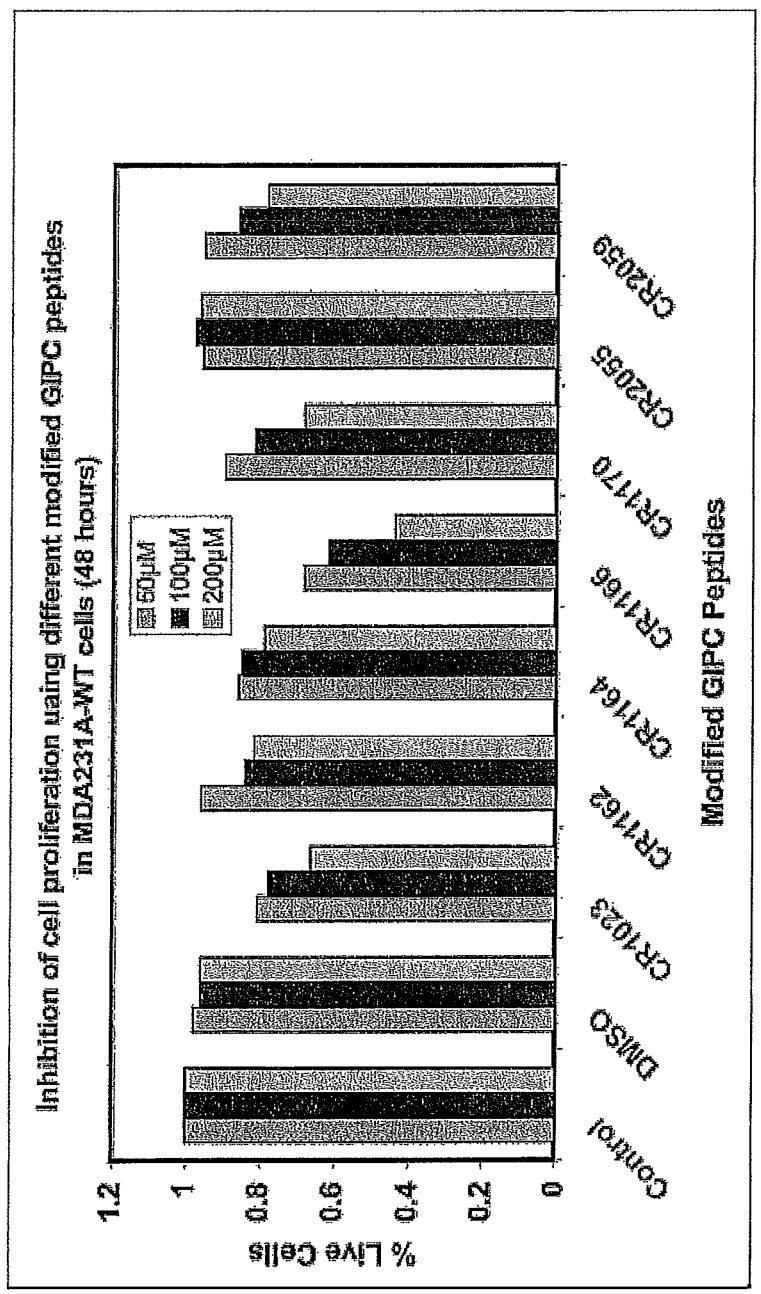
FIG. 12 illustrates the effect of GIPC inhibitor peptides CR1023 (SEQ ID NO: 16), CR1162 (SEQ ID NO: 18), CR1164 (SEQ ID NO: 19), CR1166 (SEQ ID NO: 20), CR1170 (SEQ ID NO: 22), CR2055 (SEQ ID NO: 23), and CR2059 (SEQ ID NO: 24) on MDA231-WT cells in a dose dependent manner.
Figure 13:
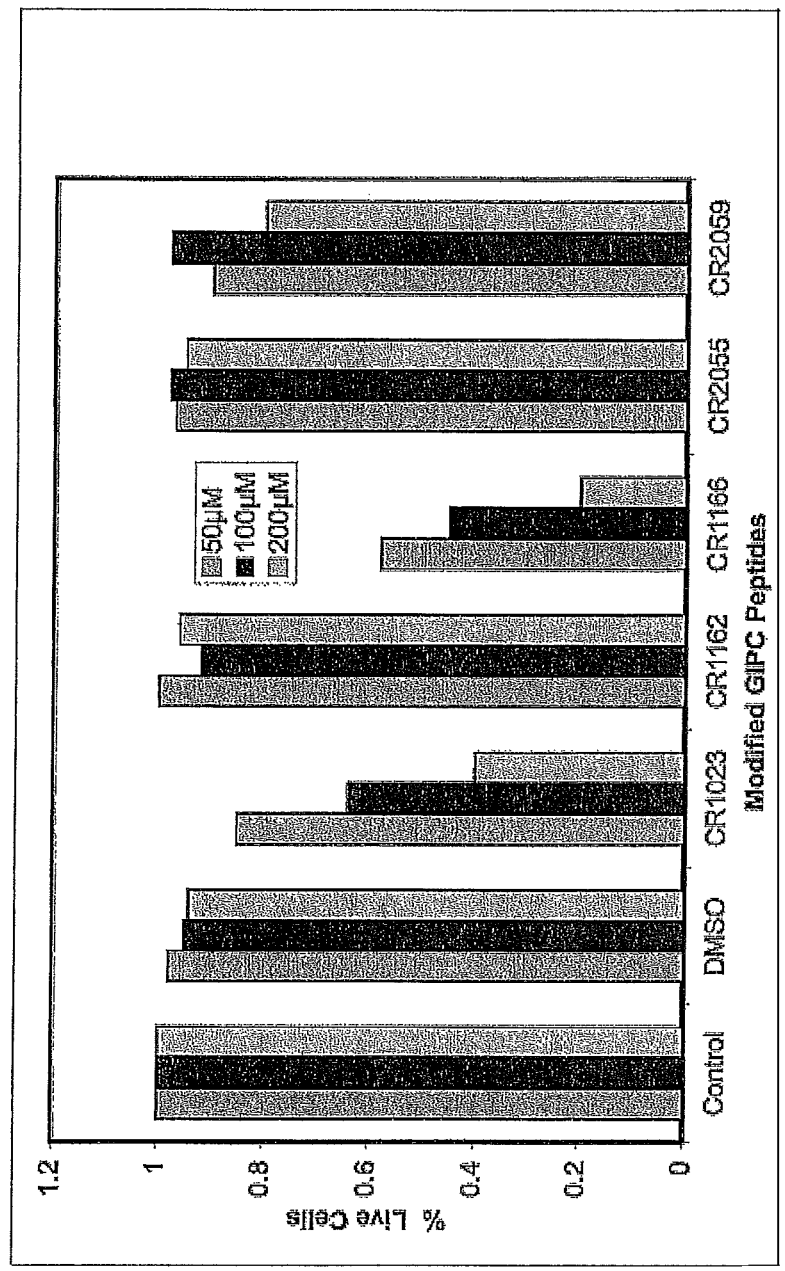
FIG. 13 shows the effect of GIPC inhibitor peptides CR1023 (SEQ ID NO: 16), CR1162 (SEQ ID NO: 18), CR1166 (SEQ ID NO: 20), CR2055 (SEQ ID NO: 23), and CR2059 (SEQ ID NO: 24) on AsPC1 cells in a dose dependent manner
Figure 14:
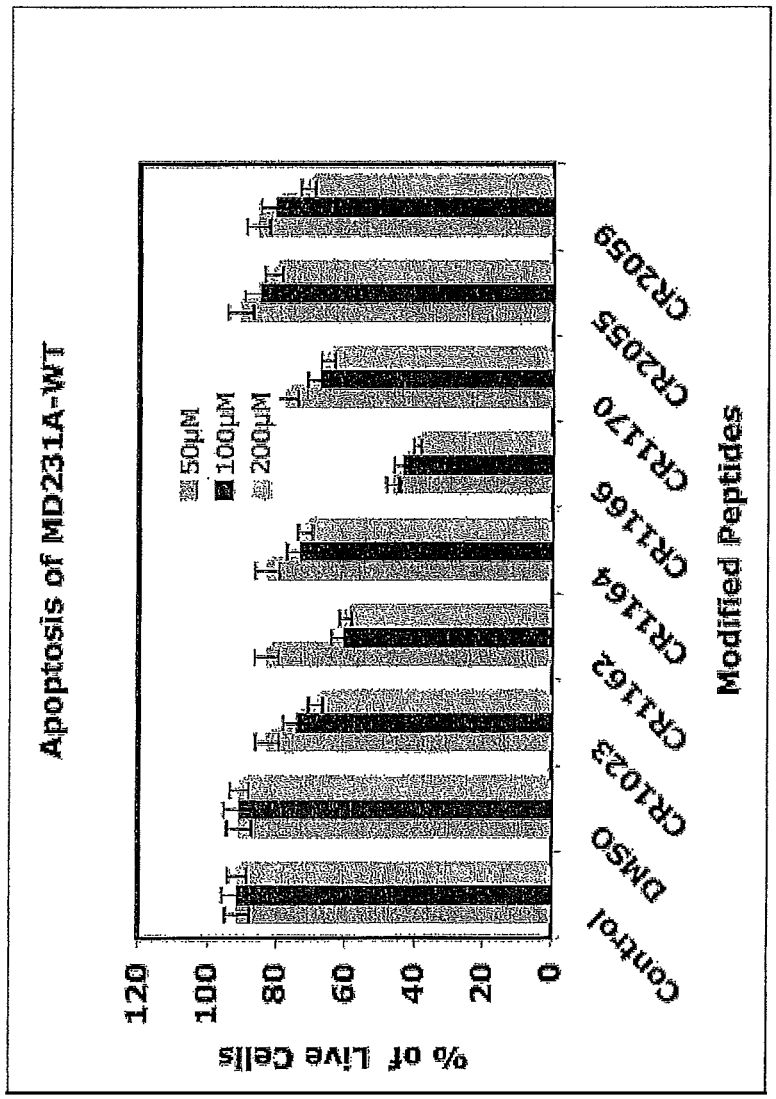
FIG. 14 is a bar graph illustrating the results of an apoptosis assay of AsPC1 cells in the presence of GIPC inhibitor peptides CR1023 (SEQ ID NO: 16), CR1162 (SEQ ID NO: 18), CR1164 (SEQ ID NO: 19), CR1166 (SEQ ID NO: 20), CR1170 (SEQ ID NO: 22), CR2055 (SEQ ID NO: 23), and CR2059 (SEQ ID NO: 24).
Figure 15:
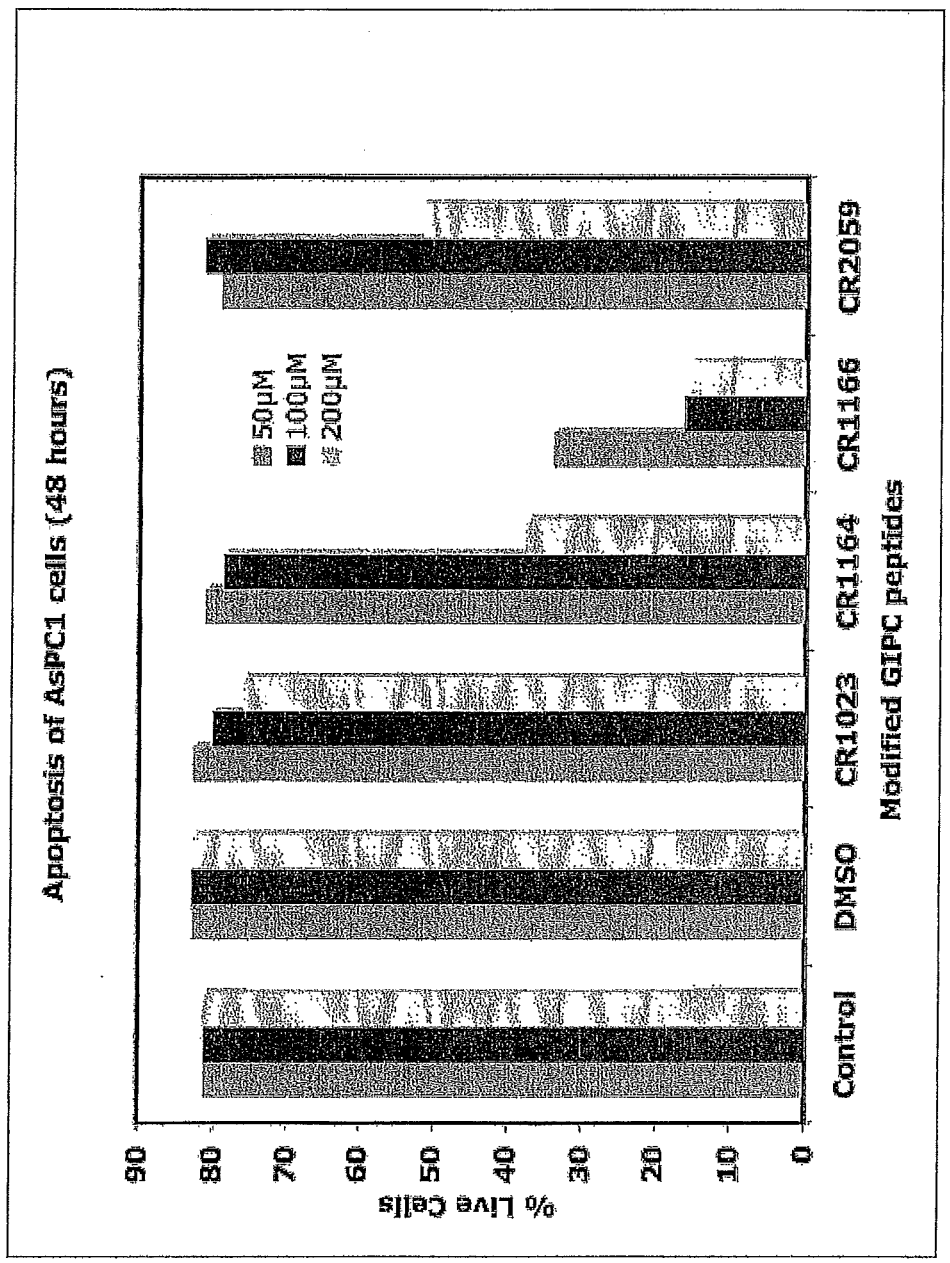
FIG. 15 is a bar graph showing the results of an apoptosis assay of MD231A-WT in the presence of GIPC inhibitor peptides CR1023 (SEQ ID NO: 16), CR1164 (SEQ ID NO: 19), CR1166 (SEQ ID NO: 20), and CR2059 (SEQ ID NO: 24).
Figure 16:
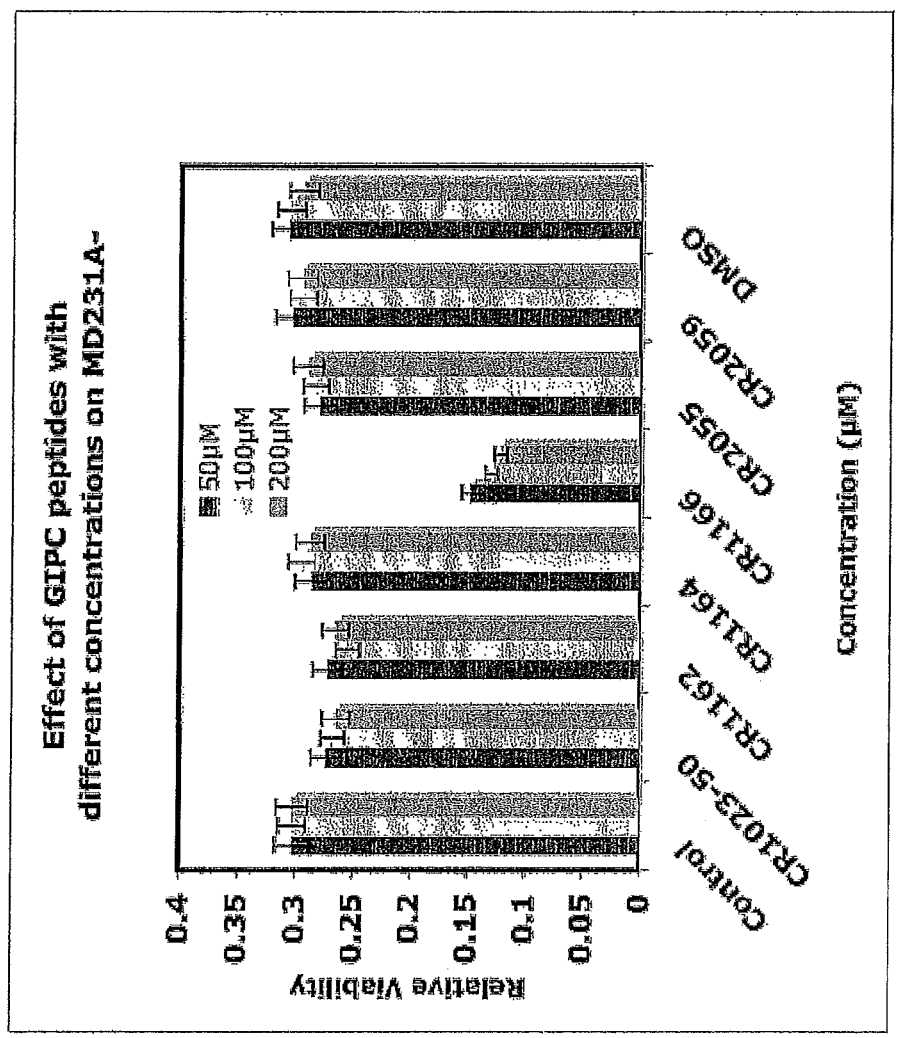
FIG. 16 is a bar graph illustrating the results of cell viability tests in the presence of different GIPC inhibitor peptides CR1023 (SEQ ID NO: 16), CR1162 (SEQ ID NO: 18), CR1164 (SEQ ID NO: 19), CR1166 (SEQ ID NO: 20), CR2055 (SEQ ID NO: 23), and CR2059 (SEQ ID NO: 24).
Figure 17:
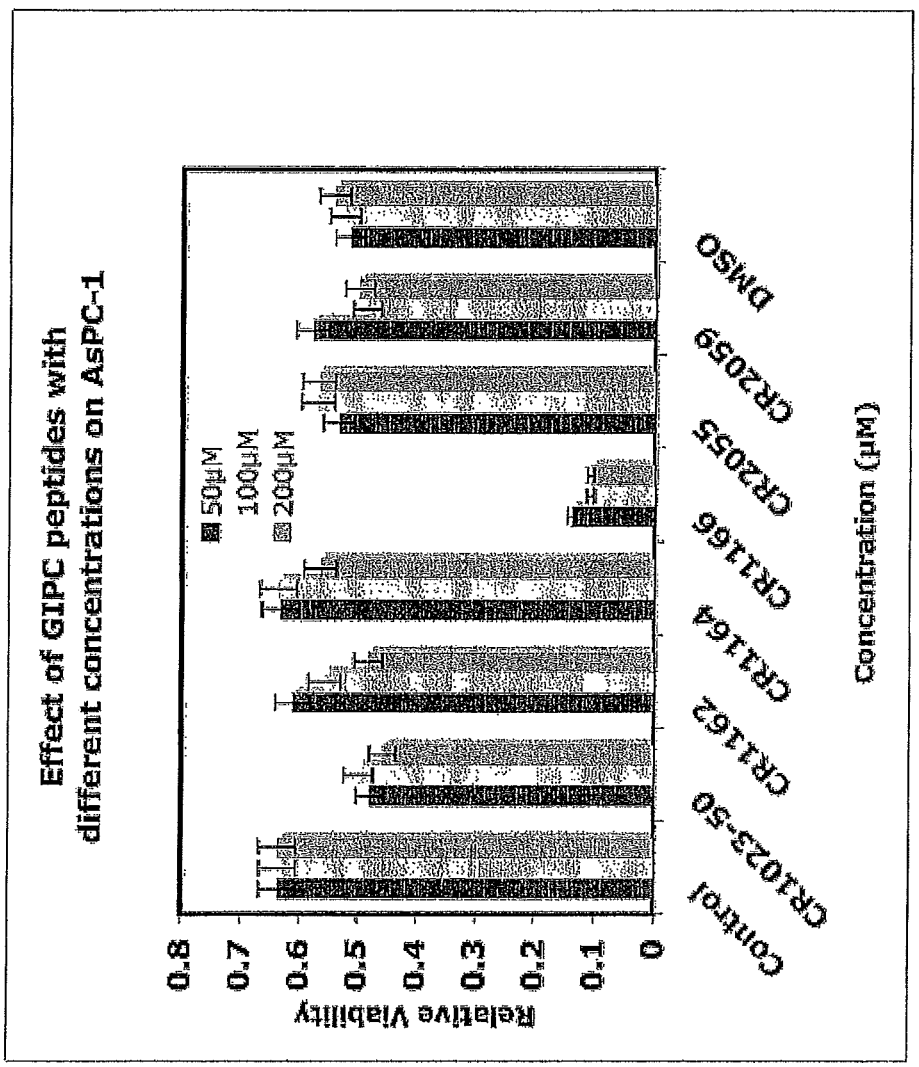
FIG. 17 is a bar graph showing the results of cell viability tests in the presence of different GIPC inhibitor peptides CR1023 (SEQ ID NO: 16), CR1162 (SEQ ID NO: 18), CR1164 (SEQ ID NO: 19), CR1166 (SEQ ID NO: 20), CR2055 (SEQ ID NO: 23), and CR2059 (SEQ ID NO: 24).

To test whether the peptide blocks the association between IGF-1R and GIPC/Synectin, MIA-PaCa2 cells were transfected with a FLAG-tagged wild type GIPC/synectin plasmid, and blotted against IGF-1R after immunoprecipitation for FLAG After treatment with the peptide and blockage of the proteasomal degradation of IGF-1R to ensure similar IGF-1R protein levels, the association between IGF-1R and GIPC/synectin was significantly reduced (FIG. 4a). These results proved that the small peptide was effective in inhibiting the association between IGF-1R and GIPC/Synectin. As a second step, the effects of the inhibitor treatment on IGF-1 receptor expression in was evaluated more detail. It has been demonstrated that RNAi for GIPC/synectin also suppressed protein levels of IGF-1R. This effect could be reversed by proteasomal inhibition suggesting that GIPC/synectin affects protein stability of IGF-1R. Accordingly, IGF-1R expression by Western blot was examined after GIPC-PDZ inhibitor treatment. The immunoblots clearly showed decreased protein levels of IGF-1R (FIG. 4b). Proteasome inhibitor treatment prevents the IGF-1R protein reduction (FIG. 4c). In vivo, Western Blot analysis showed reduced expression of IGF-1R protein in the tissue of the two tumors which developed after transplanting GIPC shRNA expressing MIA-PaCA2 cells subcutaneously in 5 nude mice. The transplantation was done subcutaneously to avoid degradation of proteins by pancreatic proteases (FIG. 5a). To evaluate the treatment effect after application of the GIPC-PDZ blocking peptide in vivo, tumor tissue which has been harvest from treated and untreated mice was. A significant reduction of IGF-1R protein in the cancer tissue after treatment with the GIPC-PDZ targeting octapeptide was observed (FIGS. 5b and 5c).

Discussion

The main focus of this study was to examine the in vivo effect on tumor growth after GIPC/synectin inhibition and its effect on one of the associated growth factor receptors, IGF-1R. Two approaches were used: 1) ex vivo transduction of pancreatic cancer cells with lentiviral shRNA followed by orthotopic transplantation; and 2) blocking GIPC/synectin with a PDZ inhibitor by intratumoral injections into an established tumor.

Here, it was demonstrated that knocking down GIPC/Synectin, a protein highly expressed in pancreatic adenocarcinoma (2), inhibits pancreatic cancer growth in an orthotopic mouse model. This supports the data of our prior study that described a prominent inhibition of pancreatic cancer cell proliferation after GIPC/synectin downregulation in vitro. The high expression of GIPC/synectin in pancreatic adenocarcinoma and the important function for the proliferation of pancreatic cancer cells makes it a target for therapeutic intervention. Accordingly, an octapeptide was developed that can block the function of GIPC/Synectin. This blocking peptide can significantly reduce tumor growth and inhibits proliferation of pancreatic cancer cells. This confirms the importance of GIPC/synectin as a central protein in pancreatic cancer cells.

GIPC/synectin has shown to be important for protein trafficking and receptor stability which gives the blocking peptide PSQSS SEA (SEQ ID NO: 3) a lot of opportunities to disrupt important cell functions: A role of GIPC/synectin in cancer cell invasion and metastasis has been demonstrated already. Also, GIPC/synectin is associated with different integrins and Syndecan-4 demonstrating a role for GIPC/synectin in cancer progression.

GIPC is also recruited by APPL to TrkA endosomes. TrkA phosphorylation plays a role in NGF mediated growth of MIA PaCa2. Moreover, a recent report suggested that APPL is important for the correct localization of Akt/PKB inside the cell. It will be important to evaluate the effect of the GIPC-PDZ blocking peptide on these different pathways in detail. In our previous work it was found that GIPC/Synection is associated with IGF-1R and important for IGF-1R stability. Accordingly, effect of the peptide treatment on IGF-1R, an important growth promoting receptor in cancer cells was focused on.

Previous results proved that GIPC/synectin is important in IGF-1R protein expression. These functions were proven to be PDZ domain dependant. In confirmation with these results it was demonstrated that blocking GIPC/synectin with an cell-permeable GlPC-PDZ inhibitor reduced protein levels of IGF-1R significantly in vitro and in an animal model. To address the mechanism of IGF-1R reduction after peptide treatment, the proteasomal pathway was inhibited. It has already been demonstrated, that the proteasomal pathway plays a role in IGF-1R receptor turnover. Proteasomal inhibition following the application of PSQSSSEA (SEQ ID NO: 3) recovers IGF-1R. This data suggests a protective function of the GIPC/Synectin-IGF-1R-interaction in maintaining IGF-1R levels. Because GIPC is an adaptor molecule for the binding to Myosin VI, it is very probable that knocking out GIPC/synectin disturbs the transportation machineries of IGF-1R after binding its ligand. Alternatively, Varsano et al. have recently shown that SEA, part of the blocking octapeptide, is also a binding motif for APPL. APPL itself is associated with Rab5 (Ras related in brain 5) and is important for the GIPC/synectin transport to the endosome. Therefore, blocking the SEA domain may inhibit binding of APPL to GIPC/Synectin. This, in turn, may inhibit the transport of GIPC/synectin to the endosome and ultimately, to IGF-1R, leading Example 6

Materials and Methods

The last eight amino residues (PSQSSSEA) of the COOH-terminal sequence of GAIP were selected for the preparation of linear ligands. In order to enhance cell permeability, myristolation (a myristoyl group, derived from myristic acid is covalently attached α-amino group of an $NH_2$-terminal amino acid of a polypeptide) was done on the $NH_2$ terminus, where it would not interfere with the critical COOH-terminal binding epitope. The peptide was designated as My-PSQSSSEA for PSQSSSEA. FITC (Fluorescein isothiocyanate) conjugated myristylated peptides [for example My-K(FITC) PSQSSSEA] were designed for localization of peptides in cells. (See Table 1 below)

| SEQ ID NO. | | | | Sequence | | | | | | |
|---|---|---|---|---|---|---|---|---|---|---|
| 16 | | | | My | P | S | Q | S | S | S | E | A |
| 17 | | | | My | P | S | Q | S | S | S | K(ben) | A |
| 18 | | | | My | P | S | Q | S | S | S | K(4-Br-ben) | A |
| 19 | | | | My | P | S | Q | S | K(ben) | S | K(ben) | A |
| 20 | | | | My | P | S | Q | S | K(4-Br-ben) | S | K(4-Br-ben) | A |
| 21 | | | | My | P | S | Q | S | K(ben) | S | E | A |
| 34 | | | | My | P | S | Q | S | K(4-Br-ben) | S | E | A |
| 22 | My | L | L | Q | G | P | S | Q | S | S | E | A |
| 23 | | | | My | S | E | S | P | S | A | S | Q |
| 24 | | | | My | S | P | S | A | S | K(4-Br-ben) | S | Q |
| 25 | | | My | K(FITC) | P | S | Q | S | S | S | E | A |
| 26 | | | My | K(FITC) | P | S | Q | S | K(ben) | S | K(ben) | A |
| 27 | | | My | K(FITC) | P | S | Q | S | K(4-Br-ben) | S | K(4-Br-ben) | A |

K(ben): benzoyllysine
K(4-Br-ben): (4-bromobenzoyl)lysine to less GIPC/synectin available for IGF-1R binding. This mechanism may also reduce the chance of an interaction between IGF-1R and GIPC/Synectin, which synergizes with the direct inhibition of the interaction by blocking the GIPC-PDZ domain.

There seems to be another important role of GIPC in IGF-1R function that is independent of transportation processes. Recently, a study in Xenopus showed that knocking out GIPC/synectin inhibits eye development by disturbing IGF-1R signaling; this study, however, did not report any reduction of IGF-1R protein levels. Therefore, GIPC/synectin may have another important function in connecting the tyrosine kinase receptor IGF-1R to G-protein signaling pathways. At this point, it is not possible to comment on the contribution of the different GIPC-associated proteins for the growth inhibition which results after blocking GIPC. Accordingly, future studies should evaluate the importance of the GIPC associated molecules like IGF-1R, Neuropilin, TrkA and APPL for the function of this octapeptide.

In conclusion, this study has demonstrated that targeting GIPC/synectin with short interfering RNA or an inhibitory PDZ domain-targeting peptide substantially reduced pancreatic adenocarcinoma growth in vivo. In any case, this peptide now represents a lead compound that can be subjected to a variety of peptidomimetic or organic modifications. These may impart improved efficacy and bioavailability properties to the next generation of such PDZ domain-targeting inhibitors in future in vivo investigations.

Cell Culture and Functional Activity Tests

MDA231-W and AsPC1 cells were cultured in RPMI 1640 media supplemented with 10% fetal bovine serum (FBS), 5% L-Glutamine, and 1% antibiotics (penicillin-streptomycin purchased from Invitrogen, Carlsbad, Calif.). Cells were maintained at 37° C. in an atmosphere containing 95% air-5% $CO_2$ (v/v). Cells were then incubated with different doses of GIPC inhibitor peptides (50-200 μM) for different time (48 h to 96 h).

Western Blot

AsPC1, MDA231-WT cells were grown in a 100 mm tissue culture dish in RPMI medium containing serum, L-glutamine and antibiotics. At 60% confluency cells were treated with GIPC inhibitor peptides in a dose dependent and time dependent manner. Untreated and GIPC inhibitor peptide-treated AsPC1 and MDA231-WT cells were washed thrice with 10 ml of cold PBS, lysed with ice-cold RIPA buffer along with halt and PIC incubated on ice for 10 min, and centrifuged at 4° C. for 10 min. The expression of IGF-1R and EGFR protein was determined in untreated and peptides treated AsPC1 and MD231A cells by Western blot analysis according to standard protocols. Briefly, protein concentration in the cell lysates was measured using Bradford assay kit (Bio-rad). The proteins were loaded on a 10% SDS-PAGE gel for separation and transferred to a membrane. The membrane was incubated with EGFR antibody (Santa cruz, sc-03) and IGF-1Rβ(C20) (Santa cruz, sc713). Blot was washed with thrice with TBS-Tween 20 (0.1%) and incubated with secondary antibody conjugated with peroxidase.

Cell Proliferation Assay

MDA-231 WT ($4 \times 10^4$) and AsPC1 cells ($2 \times 10^4$) were seeded in 24-well plates, cultured for 1 d in RPMI 1640 medium supplemented with 10% FBS, 5% L-Glutamine, and 1% antibiotics. Cells were then incubated with GIPC inhibitor peptides in a time dependent (48 h-96 h) and dose dependent manner (50-200 μM). After certain time of incubation, 1 μCi [$^3$H]-thymidine was added and proliferation assay performed as previously described. Experiments were repeated at least thrice and in triplicate.

Apoptosis Assay

MDA231-WT and AsPC1 ells were seeded into 6-well plates at a density of 4×10$^5$/2 ml of RPMI medium per well and grown overnight. Next day cells were treated with GIPC inhibitor peptides in a time dependent (48 h-96 h) and dose dependent manner (50-200 μM). After treatment with definite time, cells were extensively washed with PBS and tested with the Annexin V-FITC Apoptosis Detection Kit (Biovision, Cat. No. #K101-100) per the manufacturer's instructions.

Results and Discussion

The names of all GIPC inhibitor peptides along with their designations and molecular weights are provided in Table 1. Modified peptides were synthesized in our laboratory according to standard methods. All peptides were purified by HPLC method and characterized by several physico-chemical techniques.

Western Blot Analysis

The expression of IGF-1R and EGFR protein was determined in untreated and peptides treated AsPC1 and MD231A cells by Western blot analysis according to our standard protocols.

Cell Proliferation Assay

Before in vivo studies were performed, it was important to demonstrate the functional activity of the GIPC inhibitor peptides that resulted in enhanced inhibition of tumor cell proliferation in vitro. The cell proliferation assay was performed on two different cell lines (MDA231-WT and AsPC1) using radioactive $^3$H-thymidine incorporation assay. According to FIGS. 10-14, significant inhibitions of MD231A-WT and AsPC1 cells proliferation were observed with SEQ ID NO: 22 [My-PSQSK(4-Br-ben)SK(4-Br-ben)A] peptide in comparison to its mother peptide (My-PSQSSSEA) (SEQ ID NO: 16). A dose-dependent inhibition of proliferation in both cell lines was observed by SEQ ID NO: 22 peptide compared to other peptides. It is also important to note that corresponding control peptides SEQ ID NO: 18 (My-PSQSSSK(4-Br-ben)A) SEQ ID NO: 19 (My-PSQSK(ben)SK(ben)A) of SEQ ID NO: 22 has almost no or little effect of inhibition of proliferation in both cell lines. Again, control peptide SEQ ID NO: 23 (My-SESPSASQ) with different amino acid sequence has no effect on the inhibition of cell proliferation. The control bromo derivative peptide SEQ ID NO: 24 (My-SPSASK(4-Br-ben)SQ) has very little effect of inhibition of proliferation on both cell lines.

Apoptosis Assay

The functional activity of several modified peptides in MDA231 was tested and AsPC1 cells using different in vitro assays. To test the functional activity of these peptides, apoptosis assays using annexin/PI method against two different cell lines (MDA231-WT and AsPC1) were performed. All the experiments reported here were repeated in triplicate. FIG. 15-18 describe the dose dependent behavior of several GIPC inhibitor peptides in inducing apoptosis of MDA231-WT and AsPC1 cells. There was a significant induction of apoptosis in MDA231-WT and AsPC1 when they were treated with SEQ ID NO: 22 peptide compared to other GIPC peptides.

Example 7

Effects of GIPC Inhibitor Peptides on Cell Proliferation and Cell Survival

Figure 18:
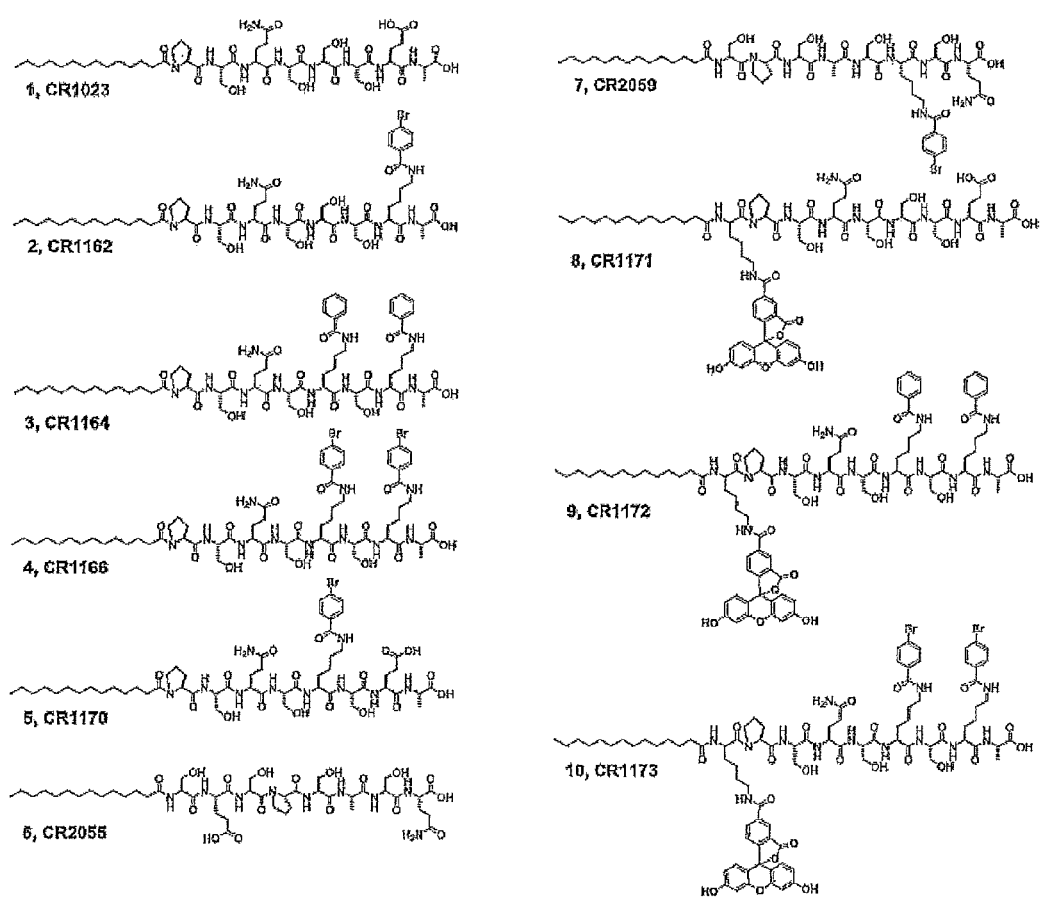
FIG. 18 depicts the chemical structures of GIPC peptide inhibitors CR1023 (SEQ ID NO: 16) and CR1166 (SEQ ID NO: 20), control peptides CR1162 (SEQ ID NO: 18), CR1164 (SEQ ID NO: 19), CR1170 (SEQ ID NO: 34), CR2055 (SEQ ID NO: 23), and CR2059 (SEQ ID NO: 24), as well as fluorescein-tagged analogs CR1171 (SEQ ID NO: 25), CR1172 (SEQ ID NO: 26), and CR1173 (SEQ ID NO: 27).

A series of GIPC inhibitor peptides were designed (FIG. 18), synthesized, purified, and tested for their in vitro and in vivo activity on cancer cells and tumors. Among the modified peptides tested, the halogenated analog CR1166 and CR1023 were the most efficacious (FIG. 18). In addition to CR1023 and CR1166, CR1162, CR1164, CR1170, CR2055, and CR2059 were designed and used as controls, and CR1171, CR1172, and CR1173 were designed as fluorescein-tagged analogs of CR1023, CR1164, and CR1166, respectively.

Figure 19:
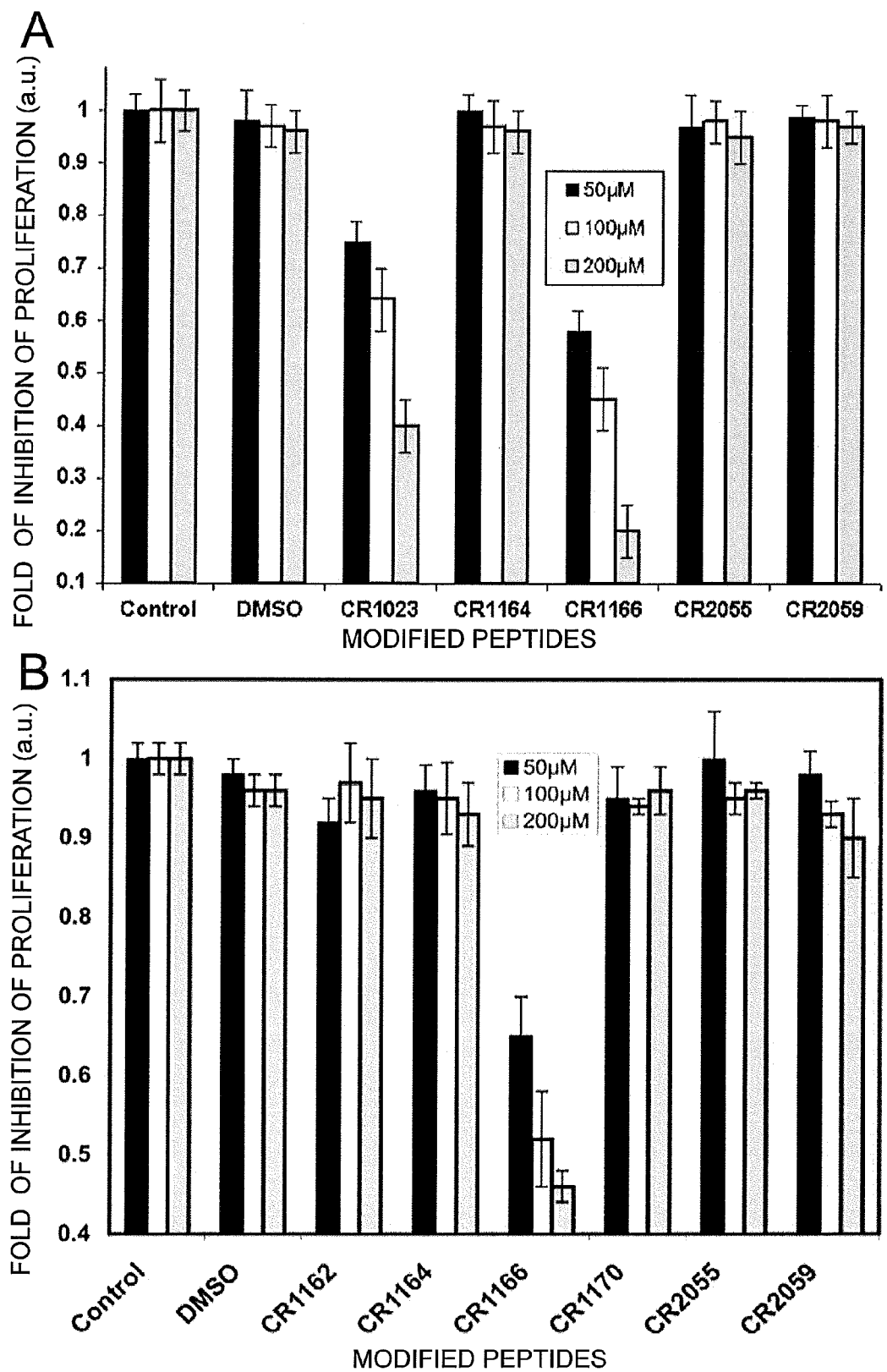
FIGS. 19(A) and 19(B) are a pair of bar graphs illustrating the dose-dependent effects of GIPC inhibitor peptides CR1023 (SEQ ID NO: 16) and CR1166 (SEQ ID NO: 20) and control peptides CR1162 (SEQ ID NO: 18), CR1164 (SEQ ID NO: 19), CR1170 (SEQ ID NO: 34), CR2055 (SEQ ID NO: 23), and CR2059 (SEQ ID NO: 24) on cell proliferation in AsPC1 pancreatic cancer cells (FIG. 19(A)) as well as MDA-MB-231-WT breast cancer cells (FIG. 19(B)).

CR1023 and CR1166 inhibited the proliferation of breast cancer cells (MDA-MB-231-WT) and pancreatic cancer cells (AsPC1) in vitro and tumor growth in vivo. Using a [$^3$H]-thymidine incorporation assay, a significant dose-dependent inhibition of cell proliferation was observed in both cell lines when cells were treated with inhibitor peptides 1023 and 1166, compared to controls peptides and DMSO (FIG. 19). AsPC1 and MDA-MB-231-WT cells were incubated with different peptides for 48 hours at different three concentrations (50 μM, 100 μM and 200 μM). Increasing the concentration of CR1166 from 50-100 μM increased the inhibition of proliferation from ~42% to ~80% in AsPC1 cells. Increasing the concentration of CR1023 from 50-100 μM increased the inhibition of proliferation from ~25% to ~60% in AsPC1 cells. Similarly, increasing the concentration of peptide CR1166 from 50-100 μM increased the inhibition of proliferation from ~32% to ~56% in MDA-MB-231-WT cells, while increasing the concentration of peptide CR1023 from 50-100 μM increased the inhibition of proliferation from ~19 to ~33% in MDA-MB-231-WT cells (FIG. 19).

Reduced cell viability of AsPC1 and MDA-MB-231-WT cells was also observed when treating with CR1023 and CR1166, but not when treated with control peptides CR1164, CR1170, CR2055, and CR2059. To assess the cytotoxic and cell viability effects of GIPC inhibitor peptides, an MTS assay was conducted in pancreatic cancer cells (AsPC1) and breast cancer cells (MDA-MB-231-WT) using CR1023 and CR1166, as well as control peptides (CR1162, CR1164, CR2055 and CR2059) in a dose dependent manner (50-200 μM). Both CR1023 and CR1166 induced a significant reduction in cell viability compared to control peptides. CR1166 reduced cell viability ~50%, ~45%, ~35% more compared to CR1023 at 50 μM, 100 μM, and 200 μM, respectively, in AsPC1 cells. Similarly, CR1166 reduced cell viability ~30-33% more at 50 μM, 100 μM, and 200 μM compared to CR1023 in MDA-MB-231-WT cells.

Figure 20:
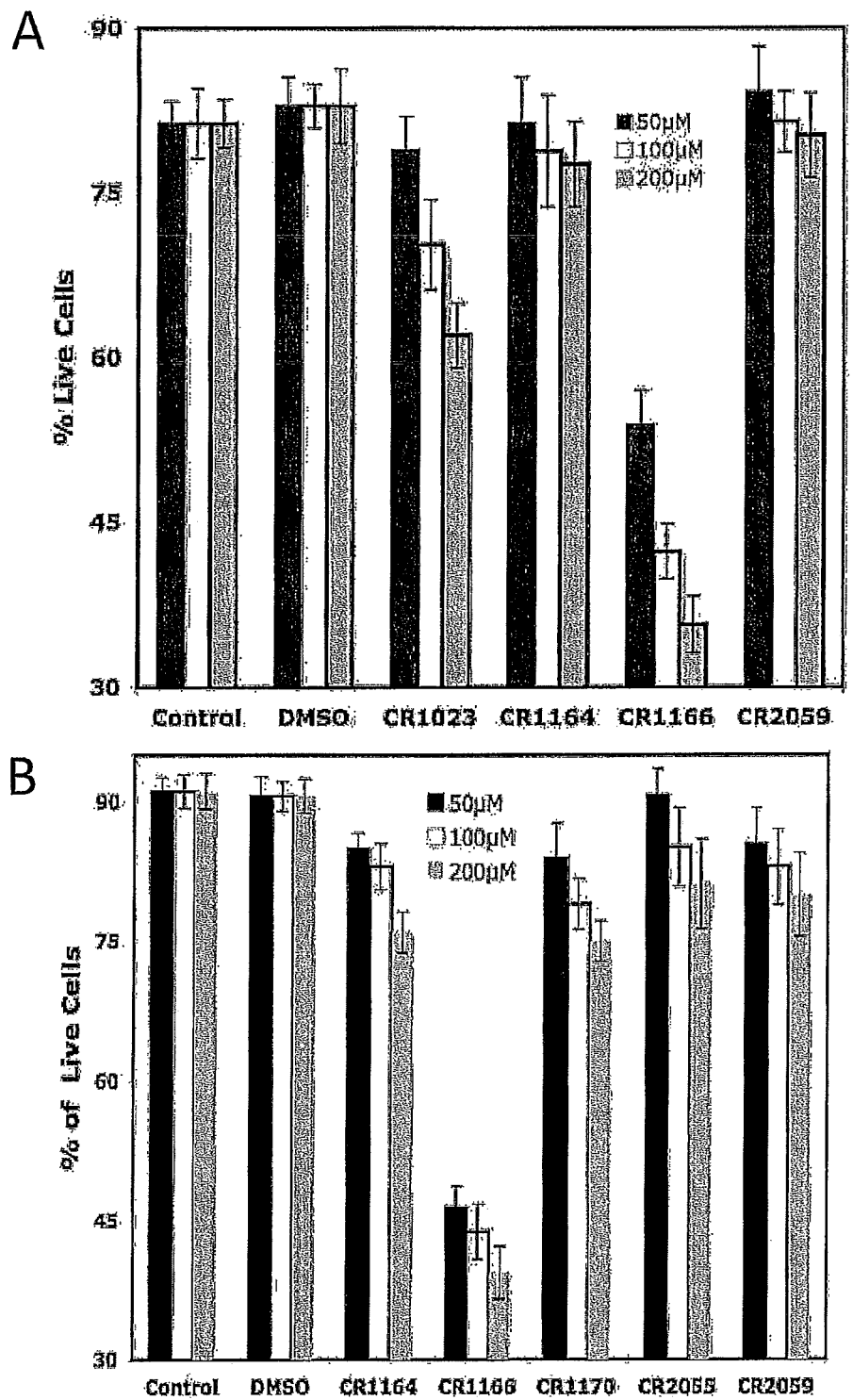
FIGS. 20(a) and 20(B) are a pair of bar graphs illustrating the dose-dependent effects of GIPC inhibitor peptides CR1023 (SEQ ID NO: 16) and CR1166 (SEQ ID NO: 20) and control peptides CR1164 (SEQ ID NO: 19), CR1170 (SEQ ID NO: 34), CR2055 (SEQ ID NO: 23), and CR2059 (SEQ ID NO: 24) on cell survival in AsPC1 pancreatic cancer cells (FIG. 20(A)) as well as MDA-MB-231-WT breast cancer cells (FIG. 20(B)).

To assess the ability of CR1023 and CR1166 to induce apoptosis, dose dependent (50-200 μM) apoptotic assays (using annexin/PI method) were performed against two different cell lines (AsPC1 and MDA-MB-231-WT) (FIG. 20). A significant induction of apoptosis was observed for CR1023 and CR1166, whereas the controls (CR1164, CR1170, CR2055 and CR2059) had no effect. Increasing the concentration of CR1166 from 50 to 200 μM induced apoptosis (from ~47% to ~65%), and caused a ~53% to ~35% reduction in live AsPC1 cells within 48 h of treatment. CR1023 caused a ~78% to ~62% reduction in live AsPC1 cells at the same time point (FIG. 20). Increasing concentrations of CR1166 from 50 to 200 μM induced apoptosis from ~54% to ~61% in MDA-MB-231-WT cells within 48 h of treatment, whereas CR1023 induced apoptosis from ~30% to ~35% over the same time course.

Example 8

Effects of GIPC Inhibitor Peptides on EGFR and IGF-1R

Figure 21A:
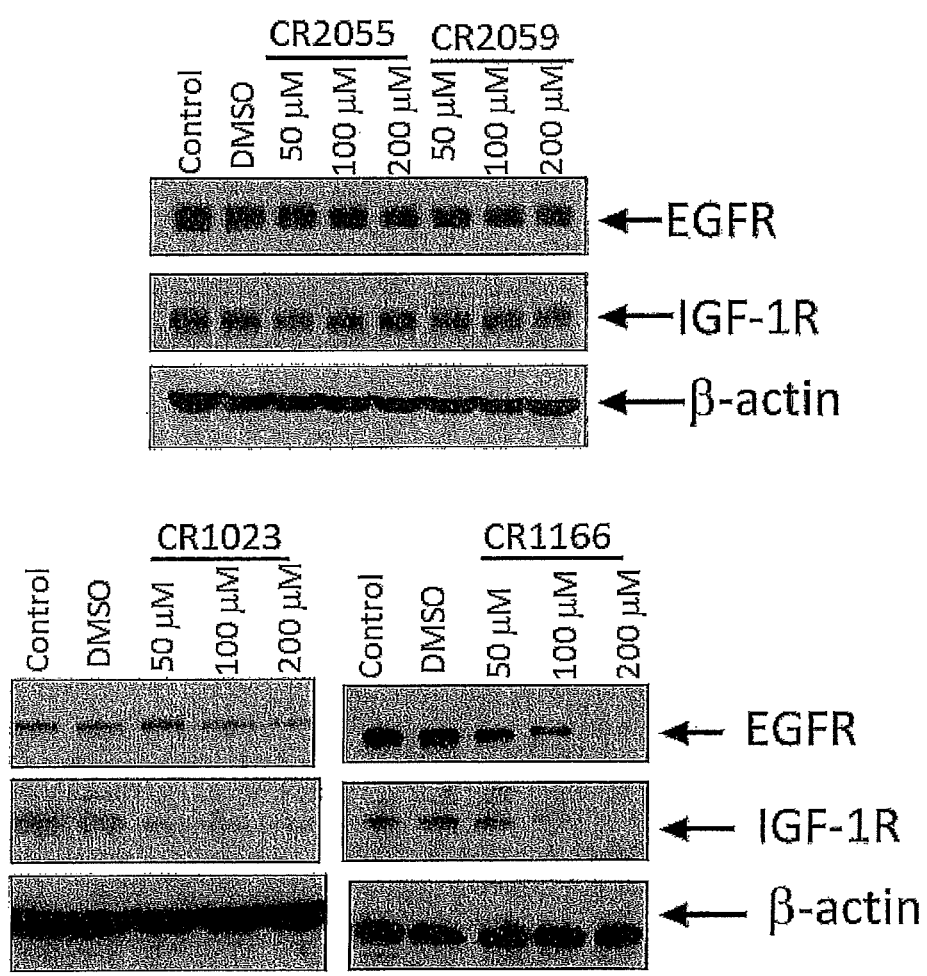
FIGS. 21(A) and 21(B) illustrate the effects of GIPC inhibitor peptides CR1023 (SEQ ID NO: 16) and CR1166 (SEQ ID NO: 20) and control peptides CR2055 (SEQ ID NO: 23) and CR2059 (SEQ ID NO: 24) on the expression of IGF-1R and EGFR in AsPC1 pancreatic cancer cells (FIG. 21(A)) as well as MDA-MB-231-WT breast cancer cells (FIG. 21(B)).
Figure 21B:
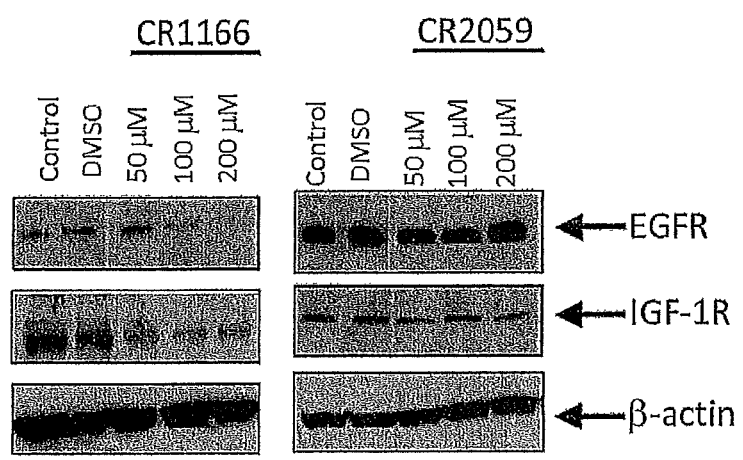

Since GIPC association with IGF-1R is important for IGF-1R stability, the effects of CR1023 and CR1166 on the expression of both IGF-1R and EGFR were investigated. The levels of EGFR and IGF-1R in pancreatic cancer cells (AsPC1) and breast cancer cells (MDA-MB-231A-WT) were analyzed using Western blot analysis after treatment with GIPC inhibitor peptides or control peptides for 48 hours at different concentrations (50 µM, 100 µM and 200 µM) (FIG. 21, A and B). In AsPC1 and MDA-MB-231A-WT cells, EGFR and IGF-1R expression was reduced by treatment with CR1023 and CR1166 compared to the control peptides CR2055 and CR2059 (FIG. 21, A and B).

Figure 22:
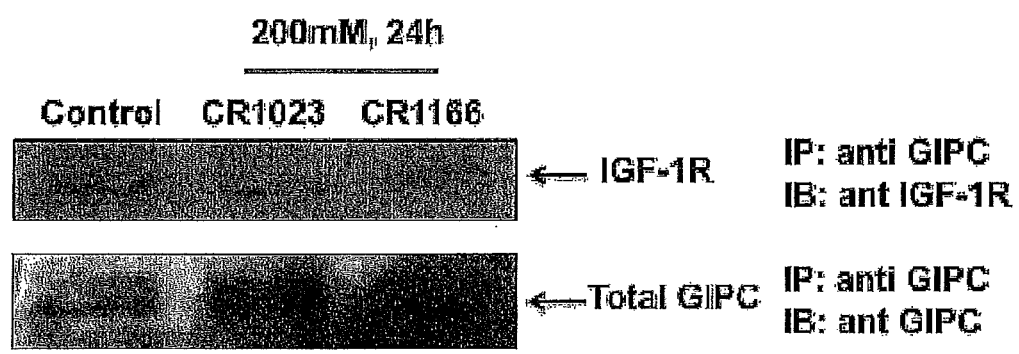
FIG. 22 illustrates the effects of GIPC inhibitor peptides CR1023 (SEQ ID NO: 16) and CR1166 (SEQ ID NO: 20) on the binding of GIPC and IGF-1R in AsPC1 cells.

Immunoprecipitations performed for GIPC, followed by immunobloting against IGF-IR indicated that CR1023 and CR 1166 interfere with the interaction between IGF-1R and GIPC in vivo (FIG. 22). AsPC1 cells were treated and lysate was collected in RIPA buffer. After immunoprecipitation with a GIPC antibody (N-19), western blot analysis was performed. These results indicated that blocking GIPC with a cell-permeable GIPC-PDZ inhibitor (CR1166 or CR1023) reduced protein levels of IGF-IR significantly in the in vitro model.

Example 9

Effects of GIPC Inhibitor Peptides on GIPC and IGF-1R Co-localization

Figure 23:
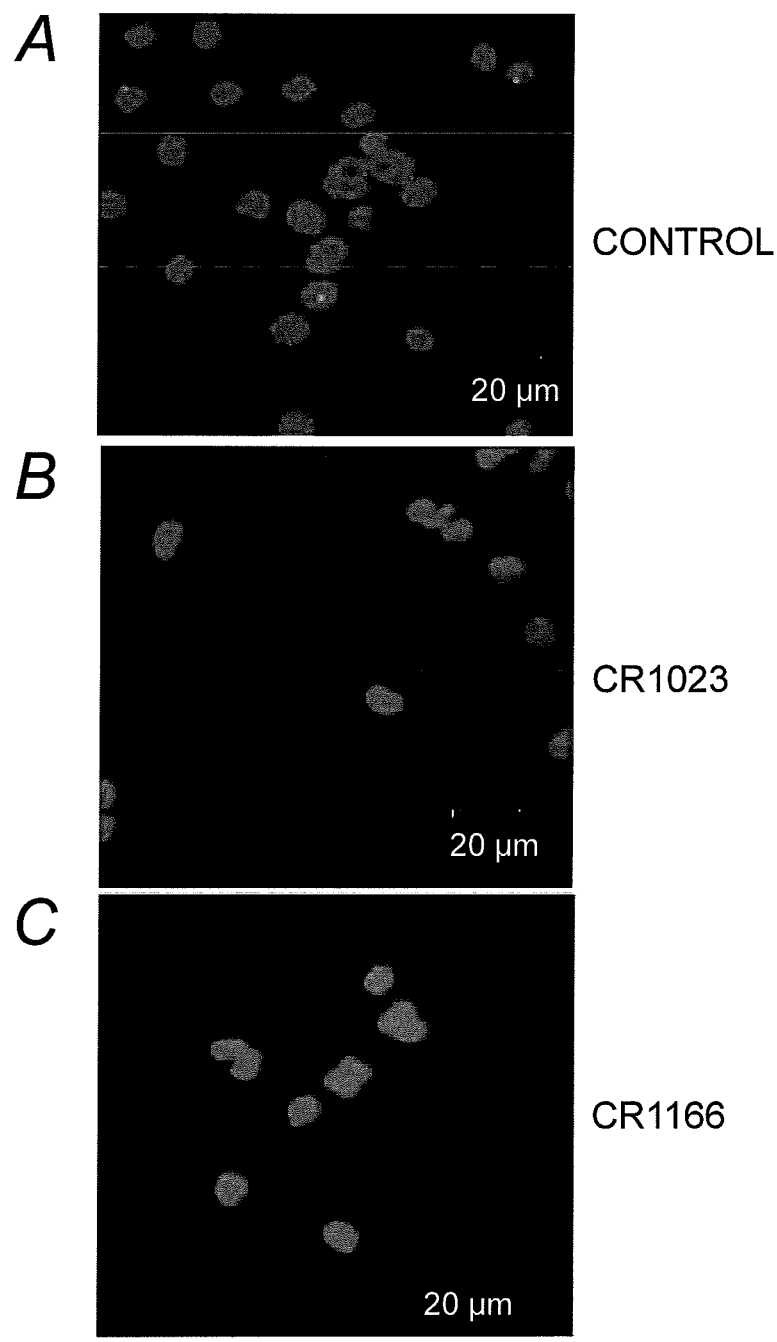
FIGS. 23(A) through 23(C) compare the effects of GIPC inhibitor peptides CR1023 (SEQ ID NO: 16) (FIG. 23(B)) and CR1166 (SEQ ID NO: 20) (FIG. 23(C)) on the co-localization of GIPC and IGF-1R in AsPC1 cells to a control (FIG. 23(A)).

Co-localization experiments were performed using a Duolink II Fluorescence kit to visualize the co-localization of GIPC and IGF-1R in control untreated AsPC1 cells (FIG. 23). Red fluorescence indicated the co-localization of GIPC and IGF-1R in AsPC1 cells. Cells treated with either CR1023 or CR1166 showed reduced red fluorescence compared to the control, indicated reduced binding between GIPC and IGF-1R in the presence of these GIPC inhibitor peptides.

Figure 24:
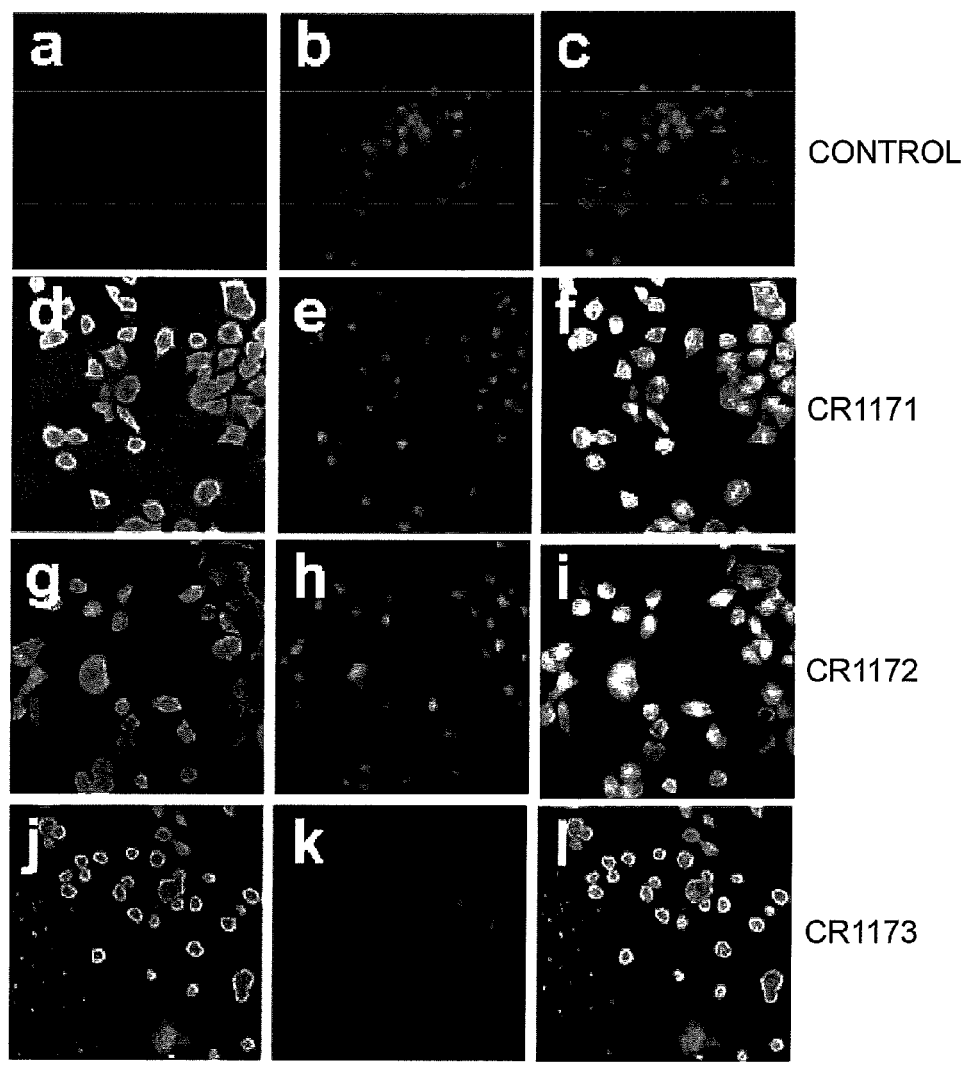
FIGS. 24(a) through 24(l) illustrate the cellular localization of GIPC inhibitor peptides compared to a control (a-c) in AsPC1 cells using fluorescein-tagged analogs. CR1171 (SEQ ID NO: 25) is the fluorescein-tagged analog of CR1023 (SEQ ID NO: 16) (d-f); CR1172 (SEQ ID NO: 26) is the fluorescein-tagged analog of CR1064 (SEQ ID NO: 19) (g-i); CR1173 (SEQ ID NO: 27) is the fluorescein-tagged analog of CR1166 (SEQ ID NO: 20) (j-l).

Furthermore, the cellular localization of both CR1023 and CR1166 was investigated in AsPC1 cells using their fluorescein-tagged analogs CR1171 and CR1173 (FIG. 24). CR1172, the fluorescein-tagged analog of CR1164 was used as a control. The green (for fluorescein) and blue (for DAPI) fluorescent microscopy images were collected for AsPC1 cells treated with peptides CR1171, CR1172 and CR1173 using a LSM 510 confocal laser scan microscope. The presence of green fluorescence in FIGS. 24d, -g, -j indicated the internalization of CR1171, CR1172 and CR1173. Untreated AsPC1 cells were devoid of the green fluorescent signal. CR1173 was localized on the membrane of AsPC1 cells, while CR1171 and CR1172 were more dispersely localized.

Example 10

In vivo Effect of Intratumoral Injections of GIPC Inhibitor Peptides

Figure 25:
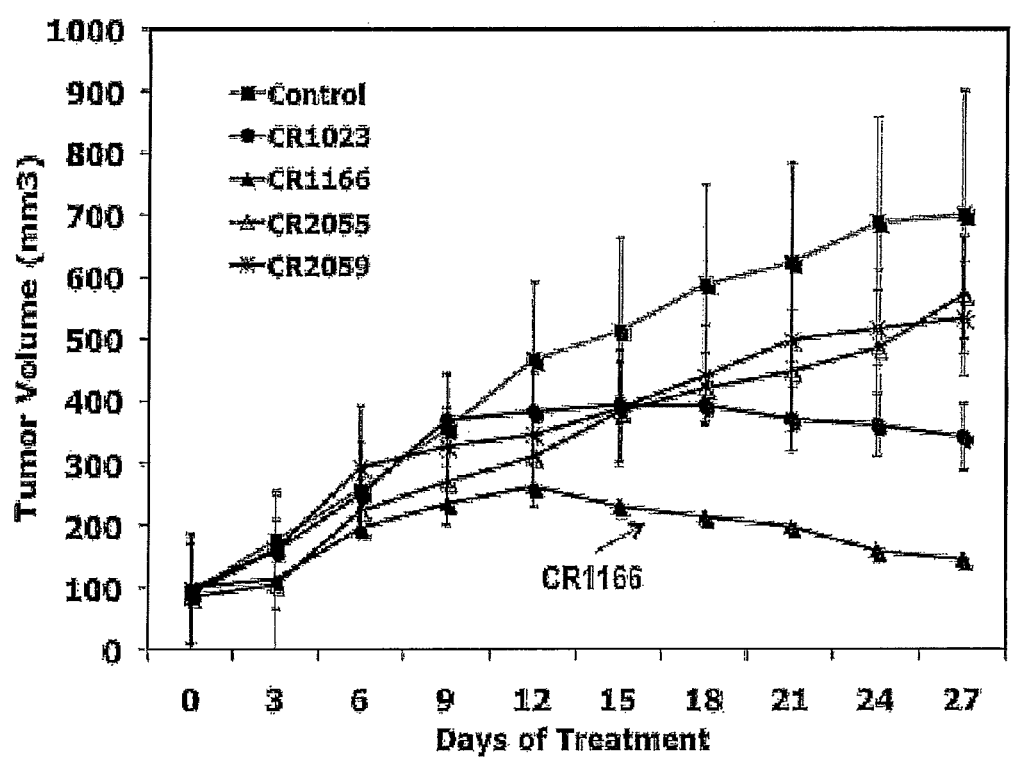
FIG. 25 illustrates the effects of the administration of GIPC inhibitor peptides CR1023 (SEQ ID NO: 16) and CR1166 (SEQ ID NO: 20) and control peptides CR2055 (SEQ ID NO: 23) and CR2059 (SEQ ID NO: 24) on the volume of pancreatic tumors collected from SCID mice over a 27 day period.
Figure 26:
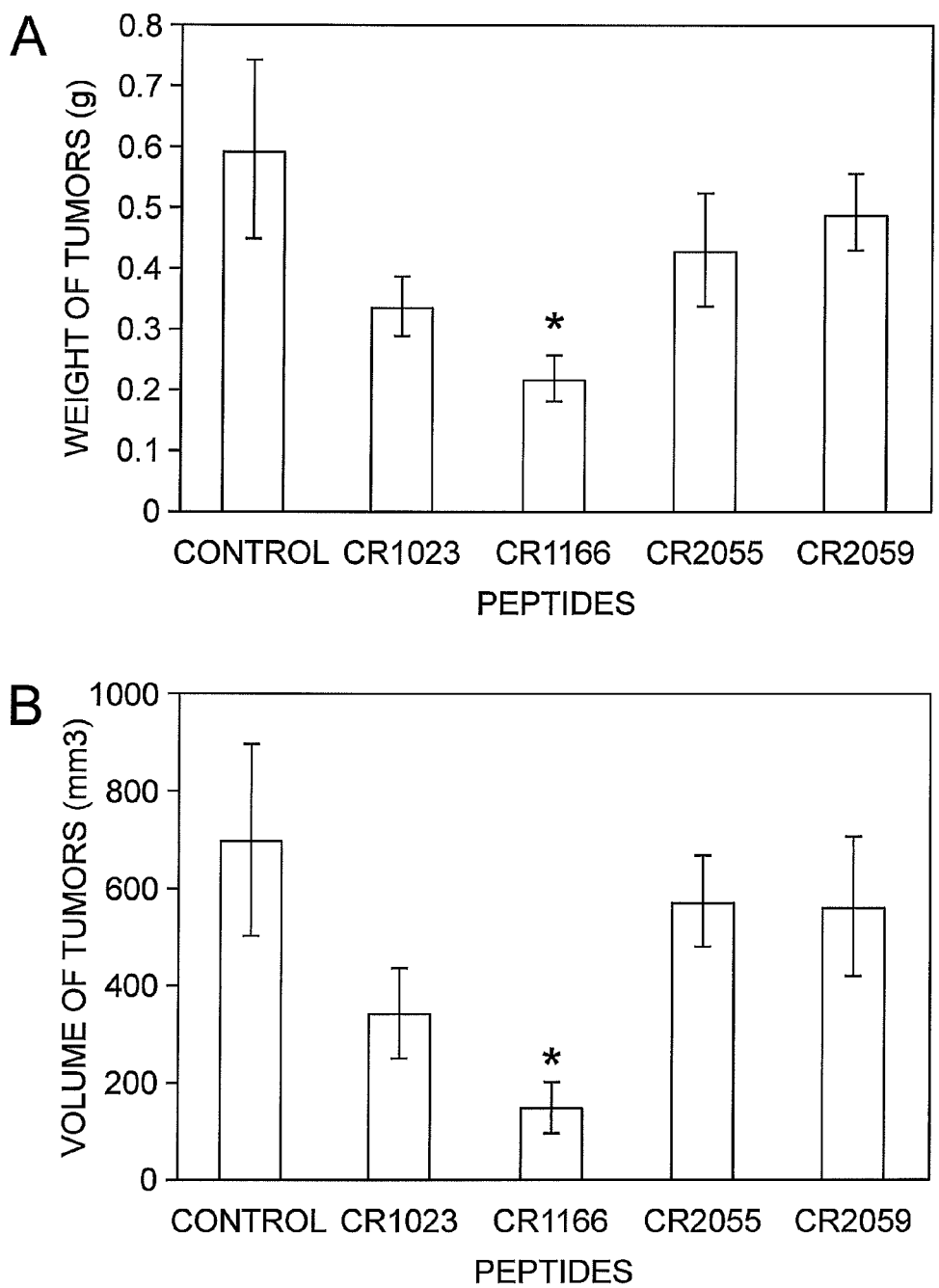
FIGS. 26(A) and 26(B) illustrate the effects of the administration of GIPC inhibitor peptides CR1023 (SEQ ID NO: 16) and CR1166 (SEQ ID NO: 20) and control peptides CR2055 (SEQ ID NO: 23) and CR2059 (SEQ ID NO: 24) on the weight (FIG. 26(A)) and volume (FIG. 26(B)) of pancreatic tumors collected from SCID mice.
Figure 27:
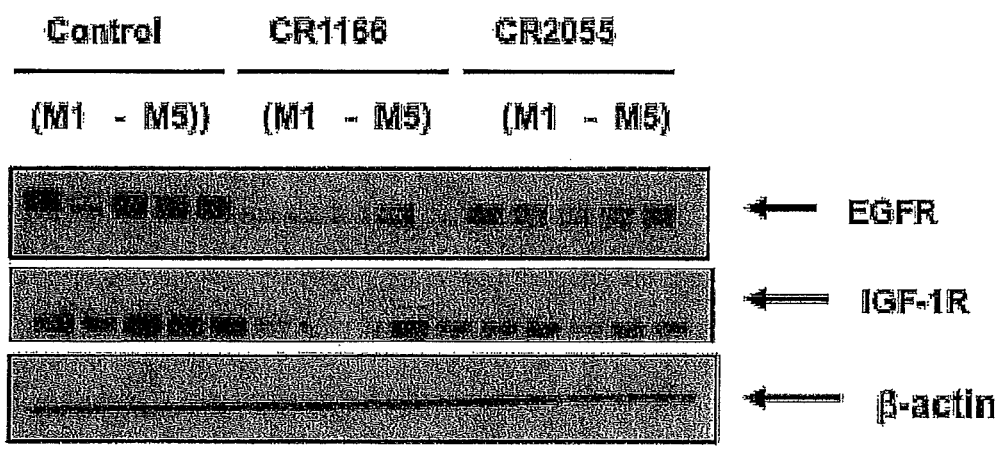
FIG. 27 illustrates the effects of the administration of GIPC inhibitor peptide CR1166 (SEQ ID NO: 20) and control peptide CR2055 (SEQ ID NO: 23) on the expression of EGFR and IGF-1R in pancreatic tumors collected from SCID mice.

In vivo tumor model experiments using female SCID mice were performed to test the effectiveness of GIPC inhibitor peptides. The pancreatic tumor model was established by injecting $5 \times 10^6$ AsPC1 cells expressing GFP/luciferase resuspended in 50 µL of sterile PBS into the mouse right flank. Similarly, the breast tumor growth model was established in mice by injecting $2 \times 10^6$ MD-MBA-231-WT cells resuspended in 50 µL of sterile PBS into the mammary fat pad of the female SCID mice. When tumors volumes reached 50-100 mm$^3$, the GIPC inhibitor peptides and controls were intratumorally injected on alternate days over a period of one month. In order to monitor the pancreatic tumor burden, the mice were non-invasively imaged using the IVIS 200 Bioluminescence Imaging system (Xenon Corp.) before sacrificing. After bioluminescence imaging, the effect of the peptides on tumor growth (weight and volume) and EGFR and IGF-1R expression from tumors collected from different groups were examined. Tumors collected after sacrificing the SCID mice were measured by digital slide calipers using the ($\frac{1}{2}ab^2$) formula. CR1023 and CR1166 significantly suppressed the pancreatic tumor growth over time compared to control peptides, CR2055 and CR2059 (FIG. 25). Mice treated with CR1166 demonstrated significant tumor regression (i.e., ~4.8 times, ~2.3 times, ~3.8 times, and ~3.9 times) as compared to control DMSO-PBS-treated mice and mice treated with CR1023, CR2055 and CR2059, respectively (FIG. 26). A portion of each tumor was evaluated for IGF-1R and EGFR expression, and a significant reduction of both IGF-1R and EGFR expression was observed in mice treated with CR1166, compared to the control CR2055 (FIG. 27).

Figure 28:
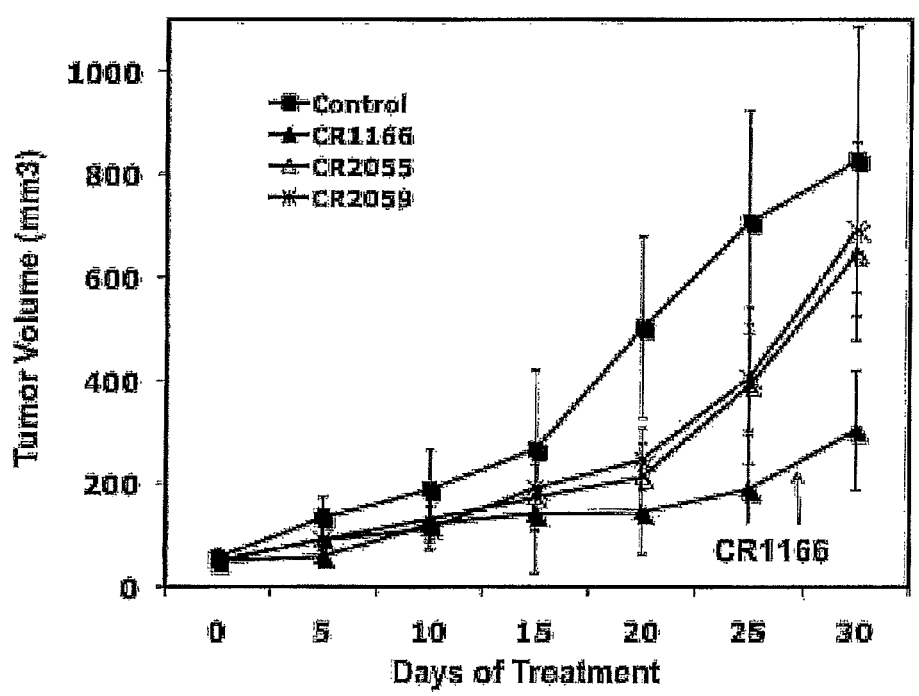
FIG. 28 illustrates the effects of intratomoral injections of GIPC inhibitor peptide CR1166 (SEQ ID NO: 20) and control peptides CR2055 (SEQ ID NO: 23) and CR2059 (SEQ ID NO: 24) on the volume of breast tumors collected from SCID mice over a 30 day period.
Figure 29:
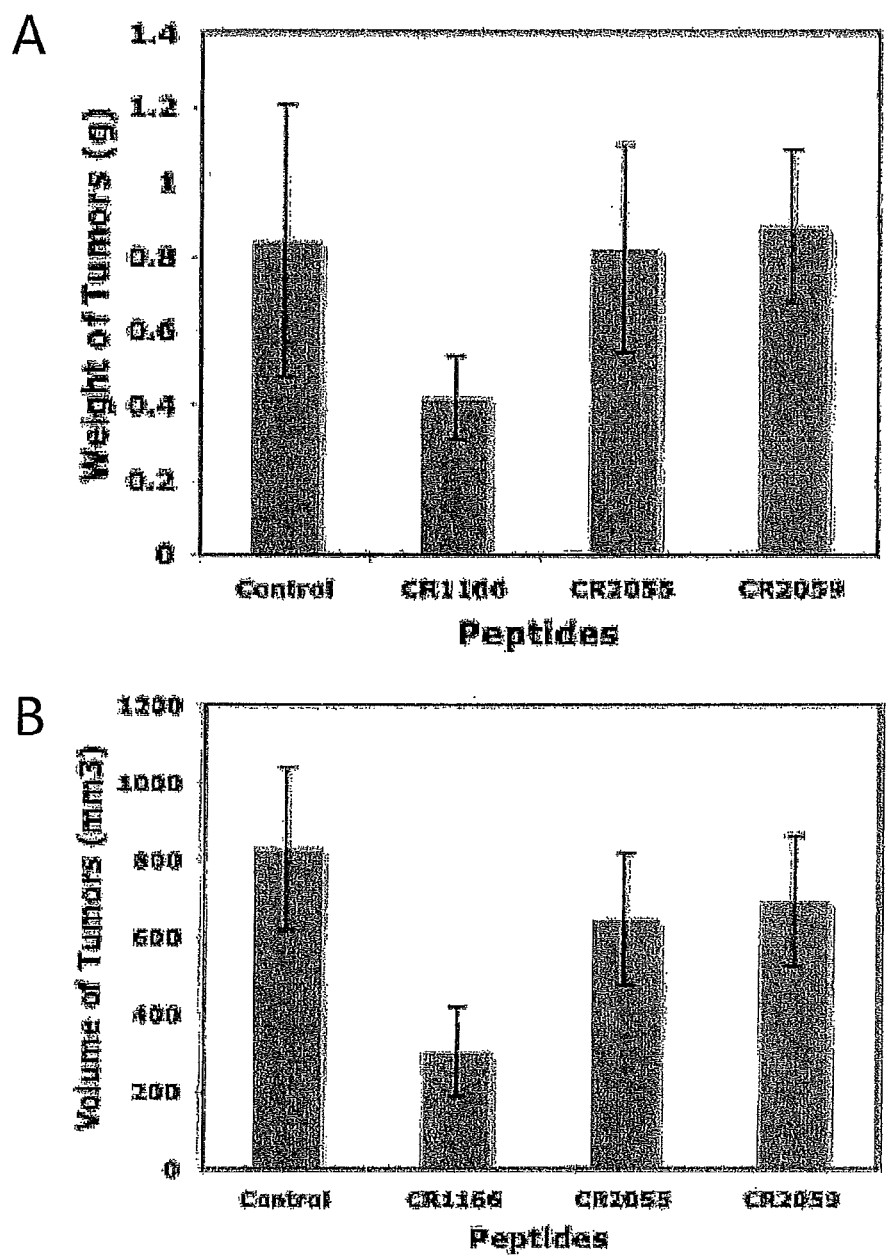
FIGS. 29(A) and 29(B) illustrate the effects of intratomoral injections of GIPC inhibitor peptide CR1166 (SEQ ID NO: 20) and control peptides CR2055 (SEQ ID NO: 23) and CR2059 (SEQ ID NO: 24) on the weight (FIG. 29(A)) and volume (FIG. 29(B)) of breast tumors collected from SCID mice.
Figure 30:
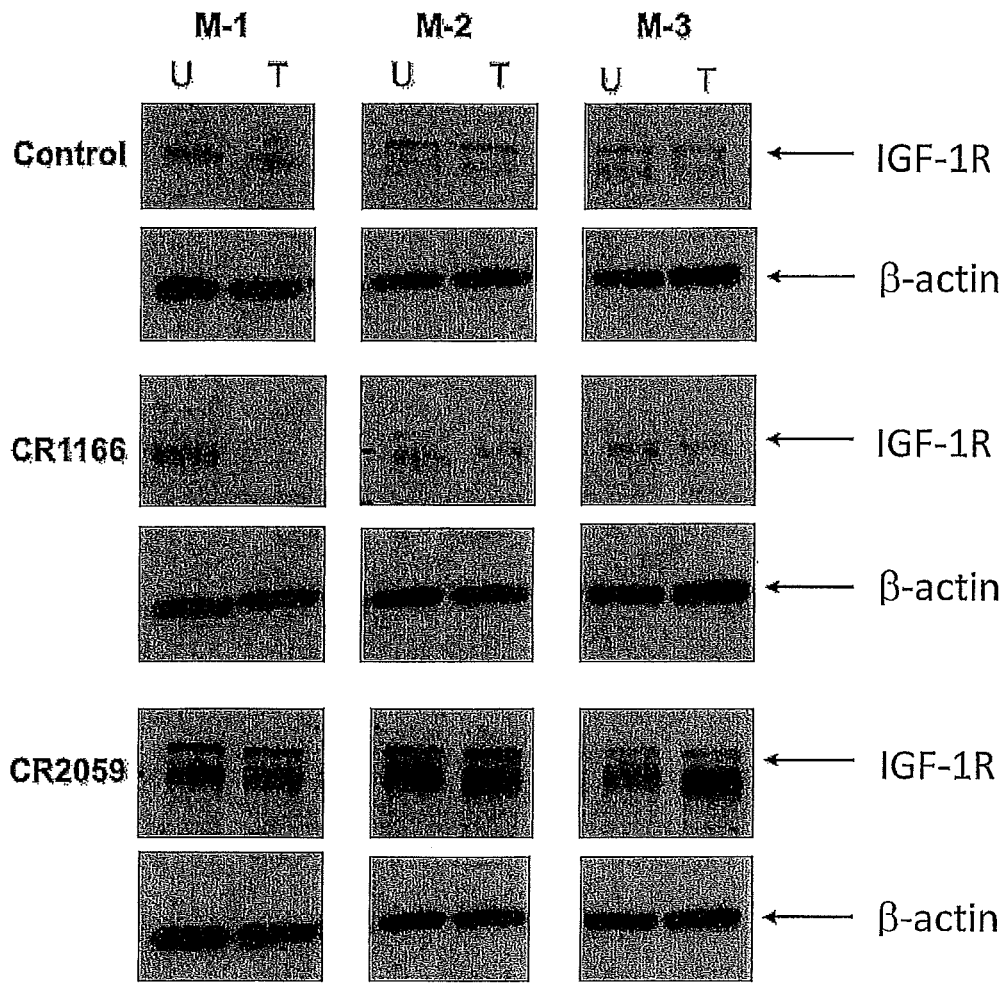
FIG. 30 illustrates the effects of intratomoral injections of GIPC inhibitor peptide CR1166 (SEQ ID NO: 20) and control peptide CR2059 (SEQ ID NO: 24) on the expression of IGF-1R in breast tumors collected from SCID mice.

Similarly, CR1166 significantly suppressed breast tumor growth over time compared to controls (FIG. 28). Tumors were harvested, and their average mass and volume were calculated (FIG. 29). Mice treated with CR1166 demonstrated significant breast tumor regression (i.e., ~2.7 times, ~1.4 times, ~2.1 times, and ~2.2 times) as compared to the control DMSO-PBS-treated mice and mice treated with CR1023 (data not shown), CR2055 and CR2059, respectively (FIG. 29). A portion of each tumor was evaluated for IGF-1R expression, and a significant reduction of IGF-1R expression was observed in mice treated CR1166 compared to CR2059 (FIG. 30).

What is claimed is:

1. A bioconjugate comprising a metal nanoparticle bound to at least one peptide, wherein said peptide comprises the amino acid sequence of SEQ ID NO:8, SEQ ID NO:9, SEQ ID NO:10 or SEQ ID NO:11, or a pharmaceutically acceptable salt thereof.

2. A peptide comprising the amino acid sequence of SEQ ID NO:9, SEQ ID NO:10 or SEQ ID NO:11, or a pharmaceutically acceptable salt thereof.

3. A pharmaceutical composition comprising the bioconjugate of claim 1, or a pharmaceutically acceptable salt thereof, and at least one pharmaceutically acceptable excipient.

4. A pharmaceutical composition comprising the peptide of claim 2, or a pharmaceutically acceptable salt thereof, and at least one pharmaceutically acceptable excipient.

5. A method for treating pancreatic cancer, wherein said cancer overexpresses GAIP interacting protein (GIPC), comprising administering to a patient in need thereof a therapeutically effective amount of a bioconjugate of claim 1, or a pharmaceutically acceptable salt thereof.

6. A method for treating pancreatic cancer, wherein said cancer overexpresses GAIP interacting protein (GIPC), comprising administering to a patient in need thereof a therapeutically effective amount of a peptide of claim 2, or a pharmaceutically acceptable salt thereof.

7. A bioconjugate comprising a metal nanoparticle bound to at least one peptide, wherein said peptide is My-SESP-SASQ (SEQ ID NO:23), or a pharmaceutically acceptable salt thereof.

8. A peptide comprising the amino acid sequence of My-SESPSASQ (SEQ ID NO:23), or a pharmaceutically acceptable salt thereof.

9. A pharmaceutical composition comprising the bioconjugate of claim 7, or a pharmaceutically acceptable salt thereof, and at least one pharmaceutically acceptable excipient.

10. A pharmaceutical composition comprising the peptide of claim 8, or a pharmaceutically acceptable salt thereof, and at least one pharmaceutically acceptable excipient.

11. A method for treating breast or pancreatic cancer, wherein said cancer overexpresses GAIP interacting protein (GIPC), comprising administering to a patient in need thereof a therapeutically effective amount of a bioconjugate of claim 7, or a pharmaceutically acceptable salt thereof.

12. A method for treating breast or pancreatic cancer, wherein said cancer overexpresses GAIP interacting protein (GIPC), comprising administering to a patient in need thereof a therapeutically effective amount of a peptide of claim 8, or a pharmaceutically acceptable salt thereof.

\* \* \* \* \*